(12) United States Patent
Kawai et al.

(10) Patent No.: US 9,920,060 B2
(45) Date of Patent: Mar. 20, 2018

(54) PYRAZOLO[3,4-D]PYRIMIDINE COMPOUND OR SALT THEREOF

(71) Applicant: TAIHO PHARMACEUTICAL CO., LTD., Chiyoda-ku (JP)

(72) Inventors: Yuichi Kawai, Tsukuba (JP); Hiroki Irie, Tsukuba (JP); Takeshi Sagara, Tsukuba (JP); Kazutaka Miyadera, Chiyoda-ku (JP)

(73) Assignee: TAIHO PHARMACEUTICAL CO., LTD., Chiyoda-ku (JP)

( * ) Notice: Subject to any disclaimer, the term of this patent is extended or adjusted under 35 U.S.C. 154(b) by 0 days.

(21) Appl. No.: 15/492,442

(22) Filed: Apr. 20, 2017

(65) Prior Publication Data

US 2017/0217970 A1    Aug. 3, 2017

Related U.S. Application Data

(63) Continuation of application No. PCT/JP2016/075380, filed on Aug. 31, 2016.

(30) Foreign Application Priority Data

Sep. 1, 2015    (JP) .................. 2015-172354

(51) Int. Cl.
*A61K 31/519* (2006.01)
*A01N 43/90* (2006.01)
*C07D 487/04* (2006.01)

(52) U.S. Cl.
CPC .......... *C07D 487/04* (2013.01); *A61K 31/519* (2013.01)

(58) Field of Classification Search
CPC ........................ A61K 31/519; C07D 487/04
USPC ........................ 514/262.1; 544/262
See application file for complete search history.

(56) References Cited

U.S. PATENT DOCUMENTS

| 2007/0135387 A1 | 6/2007 | Michaelides et al. |
| 2014/0343035 A1 | 11/2014 | Sagara et al. |
| 2016/0115168 A1 | 4/2016 | Iguchi et al. |

FOREIGN PATENT DOCUMENTS

| JP | 2009-518434 A | 5/2009 |
| WO | 2013/108809 A1 | 7/2013 |
| WO | 2015/022926 A1 | 2/2015 |

OTHER PUBLICATIONS

International Search Report dated Nov. 22, 2016 issued in PCT/JP2016/075380.

Moasser—"The oncogene HER2; Its signaling and transforming functions and its role in human cancer pathogenesis", Oncogene, Oct. 4, 2007, 26(45), pp. 6469-6487.
Yan et al.—"HER2 aberrations in cancer: Implication for therapy", Cancer Treatment Reviews 40, 2014, pp. 770-780.
Fink et al.—"Survival of HER2-Positive Breast Cancer Cells: Receptor Signaling to Apoptotic Control Centers", Genes & Cancer 4(5-6), 2013, pp. 187-195.
Neve et al.—"Effects of oncogenic ErbB2 on G1 cell cycle regulators in breast tumour cells", Oncogene, 2000, 19, pp. 1647-1656.
Rusnak et al.—"The Effects of the Novel, Reversible Epidermal Growth Factor Receptor/ErbB-2 Tyrosine Kinase Inhibitor, GW2016, on the Growth of Human Normal and Tumor-derived Cell Lines In Vitro and in Vivo", Molecular Cancer Therapeutics, Dec. 2001, vol. 1, pp. 85-94.
Li et al.—"BIBW2992, an irreversible EGFR/HER2 inhibitor highly effective in preclinical lung cancer models", Oncogene, 2008, 27, pp. 4702-4711.
Rabindran et al.—"Antitumor Activity of HKI-272, an Orally Active, Irreversible Inhibitor of the HER-2 Tyrosine Kinase", Cancer Research 64, pp. 3958-3968, Jun. 1, 2004.
Lacouture—"Mechanisms of cutaneous toxicities to EGFR inhibitors", Nature Reviews Cancer, vol. 6, Oct. 2006, pp. 803-812.

(Continued)

*Primary Examiner* — Jeffrey H Murray
(74) *Attorney, Agent, or Firm* — Oblon, McClelland, Maier & Neustadt, L.L.P.

(57) ABSTRACT

To provide a novel compound having a HER2 inhibitory effect and having a cytostatic effect. It is also intended to provide a medicament useful in the prevention and/or treatment of a disease involving HER2, particularly, cancer, on the basis of the HER2 inhibitory effect.
The present invention provides a compound of formula (I) wherein X, Y, $Z_1$, $Z_2$, $Z_3$, $Z_4$, W, n, $R_1$, $R_2$, and $R_3$ have meanings as defined in the present specification, or a salt thereof.

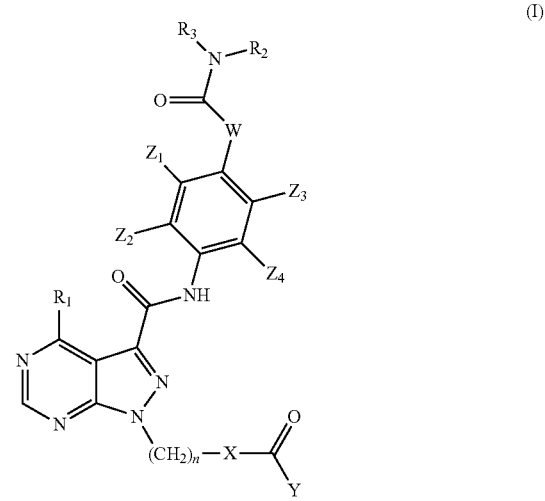

8 Claims, No Drawings

(56) References Cited

OTHER PUBLICATIONS

Yang et al.—"Diarrhea associated with afatinib: an oral ErbB family blocker", Expert Rev. Anticancer Ther. 13(6), 2013 pp. 729-736.
Zhang et al.—"Design, Synthesis, and Structure-Activity Relationship Studies of 3-(Phenylethynyl)-1 H-pyrazolo[3,4-d]pyrimidin-4-amine Derivatives as a New Class of Src Inhibitors with Potent Activities in Models of Triple Negative Breast Cancer" Journal of Medicinal Chemistry, Apr. 4, 2015, vol. 58, pp. 3957-3974.
Keefe et al.—"Tumor control versus adverse events with targeted anticancer therapies", Nature Reviews Clinical Oncology, Feb. 2012, vol. 9, pp. 98-109.

PYRAZOLO[3,4-D]PYRIMIDINE COMPOUND OR SALT THEREOF

TECHNICAL FIELD

The present invention relates to a novel pyrazolo[3,4-d]pyrimidine compound or a salt thereof which has an HER2 inhibitory effect, and a pharmaceutical composition comprising the same as an active ingredient.

BACKGROUND ART

HER2 (also called ErbB2) is a receptor-type tyrosine kinase belonging to the ErbB family.

HER2 is considered as a gene responsible for cancer (Non Patent Literature 1), and HER2 gene amplification, mutation, overexpression, and the like have been reported on various cancers (Non Patent Literature 2). It has been reported that the survival, growth signals, etc. of the cancer cells are increased by the activation of the signal transmission of HER2 and its downstream pathway in cancer cells having such HER2 gene abnormality or overexpression (Non Patent Literatures 3 and 4).

Thus, an inhibitor capable of controlling the kinase activity of HER2 presumably exerts antitumor effect by inhibiting the signal transduction of HER2 and its downstream pathway in cancer cells, and is therefore considered to be useful as a therapeutic drug for cancer.

Lapatinib (Non Patent Literature 5), afatinib (Non Patent Literature 6), and neratinib (Non Patent Literature 7) are known as compounds having HER2 inhibitory activity. These three compounds are known to exhibit high inhibitory activity against EGFR (epidermal growth factor receptor), in addition to HER2. However, such compounds might cause adverse effects due to the inhibition of the signaling pathway of EGFR. For example, inhibitors targeting EGFR are known to commonly cause adverse effects such as skin problems and gastrointestinal tract disturbances, and these adverse effects seem to be associated with the inhibition of the wild-type EGFR signaling pathway (Non Patent Literatures 8, 9, and 10).

Therefore, from the viewpoint of reducing adverse effects, there has been a demand for a highly selective HER2 inhibitor which has high inhibitory activity against HER2, but has low inhibitory activity against other kinases such as EGFR.

CITATION LIST

Patent Literature

[Patent Literature 1] International Publication No. WO 2015/022926

Non Patent Literature

[Non Patent Literature 1] Oncogene, 26, p. 6469-6487 (2007)
[Non Patent Literature 2] Cancer Treatment Reviews, 40, p. 770-780 (2014)
[Non Patent Literature 3] Gene & Cancer, 4, p. 187-195 (2013)
[Non Patent Literature 4] Oncogene, 19, p. 1647-1656 (2000)
[Non Patent Literature 5] Mol. Cancer Ther., 1, p. 85-94 (2001)
[Non Patent Literature 6] Oncogene, 27, p. 4702-4711 (2008)
[Non Patent Literature 7] Cancer Res., 64, p. 3958-3965 (2004)
[Non Patent Literature 8] Nature Reviews Cancer, 6, p. 803-812 (2006)
[Non Patent Literature 9] Expert Rev. Anticancer Ther., 13, p. 729-736 (2013)
[Non Patent Literature 10] Nature Reviews Clinical Oncology, 9, p. 98-109 (2012)

SUMMARY OF INVENTION

Technical Problem

An object of the present invention is to provide a novel compound or a salt thereof which selectively and strongly inhibits HER2 as compared with EGFR, and a pharmaceutical composition comprising the same.

Solution to Problem

The present inventors have conducted diligent studies to attain the object and consequently completed the present invention by finding that a compound group of formula (I) below having pyrazolo[3,4-d]pyrimidine as a basic structure exhibits excellent inhibitory activity against HER2 and kinase selectivity for HER2 and is useful as a medicament for the treatment of cancer.

The present invention provides the following [1] to [18]:
[1] A compound of the following formula (I) or a salt thereof:

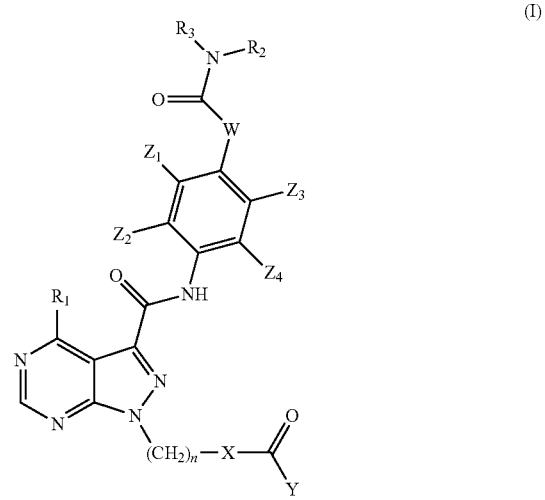

wherein X represents an optionally substituted 4- to 10-membered nitrogen-containing saturated heterocyclic group;
Y represents —C($R_4$)=C($R_5$)($R_6$);
$Z_1$, $Z_2$, $Z_3$, and $Z_4$ are the same as or different from each other and each represent a hydrogen atom, a halogen atom, a cyano group, a C2-C6 alkenyl group, an optionally substituted C1-C6 alkoxy group, an optionally substituted C1-C6 alkyl group, an optionally substituted amino group, an optionally substituted C3-C7 cycloalkyl group, a C6-C14 aromatic hydrocarbon group, or a 4- to 14-membered unsaturated heterocyclic group, or $Z_1$ and $Z_2$, or $Z_3$ and $Z_4$ optionally form, together with the respective carbon atoms bonded thereto, a benzene ring or a 5- to 7-membered saturated or unsaturated heterocyclic ring;
W represents —$CH_2$—, an oxygen atom, or —NH—;
n represents an integer of from 0 to 2;
$R_1$ represents an optionally substituted amino group;
$R_2$ and $R_3$ are the same as or different from each other and each represent a hydrogen atom, an optionally substituted C1-C6 alkoxy group, an optionally substituted C1-C6 alkyl group, or an optionally substituted C6-C14 aromatic hydrocarbon group, or $R_2$ and $R_3$ optionally form, together with the nitrogen atom bonded thereto, an optionally substituted 4- to 8-membered nitrogen-containing saturated heterocyclic group; and $R_4$, $R_5$, and $R_6$ are the same as or different from each other and each represent a hydrogen atom or an optionally substituted C1-C6 alkyl group.

[2] The compound according to [1] or a salt thereof, wherein
in the formula (I),
X is a 4- to 10-membered nitrogen-containing saturated heterocyclic group optionally having a halogen atom, a hydroxyl group, a cyano group, a C1-C6 alkyl group, or an amino group as a substituent;
$Z_1$, $Z_2$, $Z_3$, and $Z_4$ are the same as or different from each other and each are a hydrogen atom, a halogen atom, a cyano group, a C2-C6 alkenyl group, an optionally substituted C1-C6 alkoxy group, an optionally substituted C1-C6 alkyl group, an optionally substituted amino group, an optionally substituted C3-C7 cycloalkyl group, or a 4- to 14-membered unsaturated heterocyclic group, or $Z_1$ and $Z_2$, or $Z_3$ and $Z_4$ optionally form, together with the respective carbon atoms bonded thereto, a benzene ring or a 5- to 7-membered saturated or unsaturated heterocyclic ring;
n is 0; and
$R_1$ is an amino group.

[3] The compound according to [1] or [2] or a salt thereof, wherein
in the formula (I),
X is a 4- to 8-membered nitrogen-containing saturated heterocyclic group optionally having a halogen atom or a C1-C6 alkyl group as a substituent;
Y is —$C(R_4)=C(R_5)(R_6)$;
$Z_1$, $Z_2$, $Z_3$, and $Z_4$ are the same as or different from each other and each are a hydrogen atom, a halogen atom, a cyano group, a C2-C6 alkenyl group, an optionally halogen atom-substituted C1-C6 alkoxy group, a C1-C6 alkyl group, an optionally C1-C6 alkyl group-substituted amino group, a C3-C7 cycloalkyl group, or a monocyclic 4- to 6-membered unsaturated heterocyclic group having one oxygen atom, or $Z_1$ and $Z_2$, or $Z_3$ and $Z_4$ optionally form, together with the respective carbon atoms bonded thereto, a benzene ring or a 5- to 7-membered saturated or unsaturated heterocyclic ring;
W is —$CH_2$—, an oxygen atom, or —NH—;
n is 0;
$R_1$ is an amino group;
$R_2$ and $R_3$ are the same as or different from each other and each are a hydrogen atom, a C1-C6 alkoxy group, a C1-C6 alkyl group, or a C6-C14 aromatic hydrocarbon group, or $R_2$ and $R_3$ optionally form, together with the nitrogen atom bonded thereto, an optionally hydroxyl group-substituted 4- to 8-membered nitrogen-containing saturated heterocyclic group; and
$R_4$, $R_5$, and $R_6$ are the same as or different from each other and each are a hydrogen atom or an optionally di(C1-C6 alkyl)amino group-substituted C1-C6 alkyl group.

[4] The compound according to any of [1] to [3] or a salt thereof, wherein
in the formula (I),
X is a pyrrolidinyl group optionally having a C1-C6 alkyl group as a substituent, or a piperidinyl group optionally having a halogen atom as a substituent;
Y is —$C(R_4)=C(R_5)(R_6)$; and
$R_4$, $R_5$, and $R_6$ are the same as or different from each other and each are a hydrogen atom or a dimethylaminomethyl group.

[5] The compound according to any of [1] to [4] or a salt thereof, wherein
in the formula (I),
X is a pyrrolidinyl group, a methylpyrrolidinyl group, a piperidinyl group, or a fluoropiperidinyl group;
Y is

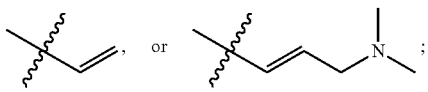

and
$R_2$ and $R_3$ are the same as or different from each other and each are a hydrogen atom, a methoxy group, a methyl group, or a phenyl group, or $R_2$ and $R_3$ optionally form, together with the nitrogen atom bonded thereto, an azetidinyl group optionally having a hydroxyl group as a substituent, a pyrrolidinyl group, or a piperidinyl group.

[6] The compound according to any of [1] to [5] or a salt thereof, wherein
in the formula (I),
X is a pyrrolidinyl group, a methylpyrrolidinyl group, a piperidinyl group, or a fluoropiperidinyl group;
Y is

$Z_1$, $Z_2$, $Z_3$, and $Z_4$ are the same as or different from each other and each are a hydrogen atom, a fluorine atom, a chlorine atom, a bromine atom, a cyano group, a vinyl group, a methoxy group, a fluoromethoxy group, a difluoromethoxy group, a methyl group, an ethyl group, a dimethylamino group, a cyclopropyl group, or a furyl group, or $Z_1$ and $Z_2$, or $Z_3$ and $Z_4$ optionally form, together with the respective carbon atoms bonded thereto, a benzene ring, a pyridine ring, or a dioxolane ring;
W is —$CH_2$—, an oxygen atom, or —NH—;
n is 0;
$R_1$ is an amino group; and
$R_2$ and $R_3$ are the same as or different from each other and each are a methoxy group, a methyl group, or a phenyl group, or $R_2$ and $R_3$ optionally form, together with the nitrogen atom bonded thereto, a hydroxyazetidinyl group, a pyrrolidinyl group, or a piperidinyl group.

[7] The compound according to any of [1] to [6] or a salt thereof, wherein the compound is selected from the group consisting of the following (1) to (20):
(1) (R)-1-(1-acryloylpiperidin-3-yl)-4-amino-N-(5-bromo-4-(2-(dimethylamino)-2-oxoethyl)-2-methylphenyl)-1H-pyrazolo[3,4-d]pyrimidine-3-carboxamide,
(2) (R)-1-(1-acryloylpiperidin-3-yl)-4-amino-N-(2-chloro-4-(2-(dimethylamino)-2-oxoethyl)-5-methylphenyl)-1H-pyrazolo[3,4-d]pyrimidine-3-carboxamide, (3) (R)-1-(1-acryloylpiperidin-3-yl)-4-amino-N-(2-chloro-4-(2-(dimethylamino)-2-oxoethyl)-3-methylphenyl)-1H-pyrazolo[3,4-d]pyrimidine-3-carboxamide,
(4) (R)-1-(1-acryloylpiperidin-3-yl)-4-amino-N-(4-(2-(dimethylamino)-2-oxoethyl)-2-methylphenyl)-1H-pyrazolo[3,4-d]pyrimidine-3-carboxamide,
(5) (R)-1-(1-acryloylpiperidin-3-yl)-4-amino-N-(4-(2-(dimethylamino)-2-oxoethyl)naphthalen-1-yl)-1H-pyrazolo[3,4-d]pyrimidine-3-carboxamide,
(6) (R)-1-(1-acryloylpiperidin-3-yl)-4-amino-N-(2-chloro-4-(2-(dimethylamino)-2-oxoethyl)phenyl)-1H-pyrazolo[3,4-d]pyrimidine-3-carboxamide,
(7) (R)-1-(1-acryloylpiperidin-3-yl)-4-amino-N-(4-(2-(dimethylamino)-2-oxoethyl)-2-methoxyphenyl)-1H-pyrazolo[3,4-d]pyrimidine-3-carboxamide,
(8) (R)-1-(1-acryloylpiperidin-3-yl)-4-amino-N-(3-chloro-4-(2-(dimethylamino)-2-oxoethyl)phenyl)-1H-pyrazolo[3,4-d]pyrimidine-3-carboxamide,
(9) (R)-1-(1-acryloylpiperidin-3-yl)-4-amino-N-(5-chloro-4-(2-(dimethylamino)-2-oxoethyl)-2-methoxyphenyl)-1H-pyrazolo[3,4-d]pyrimidine-3-carboxamide,
(10) (R)-1-(1-acryloylpiperidin-3-yl)-4-amino-N-(4-(2-(dimethylamino)-2-oxoethyl)-5-fluoro-2-methylphenyl)-1H-pyrazolo[3,4-d]pyrimidine-3-carboxamide,
(11) (R)-1-(1-acryloylpiperidin-3-yl)-4-amino-N-(3-chloro-4-(2-(dimethylamino)-2-oxoethyl)-2-methoxyphenyl)-1H-pyrazolo[3,4-d]pyrimidine-3-carboxamide,
(12) (R)-1-(1-acryloylpiperidin-3-yl)-4-amino-N-(4-(2-(dimethylamino)-2-oxoethyl)-3-fluoro-2-methylphenyl)-1H-pyrazolo[3,4-d]pyrimidine-3-carboxamide,
(13) (R)-1-(1-acryloylpiperidin-3-yl)-4-amino-N-(4-(2-(dimethylamino)-2-oxoethyl)-2,3-dimethylphenyl)-1H-pyrazolo[3,4-d]pyrimidine-3-carboxamide,
(14) (R)-1-(1-acryloylpiperidin-3-yl)-4-amino-N-(4-(2-(dimethylamino)-2-oxoethyl)-3-fluoro-2-methoxyphenyl)-1H-pyrazolo[3,4-d]pyrimidine-3-carboxamide,
(15) (R)-1-(1-acryloylpiperidin-3-yl)-4-amino-N-(2-(difluoromethoxy)-4-(2-(dimethylamino)-2-oxoethyl)phenyl)-1H-pyrazolo[3,4-d]pyrimidine-3-carboxamide,
(16) (R)-1-(1-acryloylpiperidin-3-yl)-4-amino-N-(4-(2-(dimethylamino)-2-oxoethyl)-2-(fluoromethoxy)phenyl)-1H-pyrazolo[3,4-d]pyrimidine-3-carboxamide,
(17) (R)-1-(1-acryloylpiperidin-3-yl)-4-amino-N-(2-bromo-4-(2-(dimethylamino)-2-oxoethyl)phenyl)-1H-pyrazolo[3,4-d]pyrimidine-3-carboxamide,
(18) (R)-1-(1-acryloylpiperidin-3-yl)-4-amino-N-(2-chloro-4-(2-(dimethylamino)-2-oxoethyl)-5-fluorophenyl)-1H-pyrazolo[3,4-d]pyrimidine-3-carboxamide,
(19) (R)-1-(1-acryloylpiperidin-3-yl)-4-amino-N-(5-chloro-4-(2-(dimethylamino)-2-oxoethyl)-2-methylphenyl)-1H-pyrazolo[3,4-d]pyrimidine-3-carboxamide, and
(20) (R)-1-(1-acryloylpiperidin-3-yl)-4-amino-N-(2,5-dichloro-4-(2-(dimethylamino)-2-oxoethyl)phenyl)-1H-pyrazolo[3,4-d]pyrimidine-3-carboxamide.

[8] A HER2 inhibitor comprising a compound according to any of [1] to [7] or a salt thereof as an active ingredient.
[9] A pharmaceutical composition comprising a compound according to any of [1] to [7] or a salt thereof.
[10] An antitumor agent comprising a compound according to any of [1] to [7] or a salt thereof as an active ingredient.
[11] Use of a compound according to any of [1] to [7] or a salt thereof for producing a HER2 inhibitor.
[12] Use of a compound according to any of [1] to [7] or a salt thereof for producing a pharmaceutical composition.
[13] Use of a compound according to any of [1] to [7] or a salt thereof for producing an antitumor agent.
[14] The compound according to any of [1] to [7] or a salt thereof for use in the inhibition of HER2.
[15] The compound according to any of [1] to [7] or a salt thereof for use as a medicament.
[16] The compound according to any of [1] to [7] or a salt thereof for use as an antitumor agent.
[17] A method for inhibiting HER2, comprising administering an effective amount of a compound according to any of [1] to [7] or a salt thereof to a subject in need thereof.
[18] A method for preventing and/or treating tumor, comprising administering an effective amount of a compound according to any of [1] to [7] or a salt thereof to a subject in need thereof.

Lapatinib (Non Patent Literature 5), afatinib (Non Patent Literature 6), and neratinib (Non Patent Literature 7) mentioned above are known as compounds related to the present invention. These three compounds have a 4-phenylaminoquinazoline or 4-phenylaminoquinoline structure and differ largely in that the compounds lack a pyrazolo[3,4-d]pyrimidine structure, which is a feature of the compound of the present invention. Also, a feature of the compound of the present invention is that the compound has high HER2 selectivity.

In contrast, the compound described in Patent Literature 1 is a pyrazolo[3,4-d]pyrimidine compound which however has a benzoxazole group or an oxazolopyridine group on the substituent at position 3 thereof and structurally differs largely in that the compound lacks a 2-(4-aminophenyl) acetamide group, a 4-aminophenylcarbamate group, or 1-(4-aminophenyl) urea, which is a feature of the compound of the present invention. The compound described in this patent literature is a compound inhibiting Bruton's tyrosine kinase (BTK). As mentioned later, the compound described in this patent literature (Comparative Example compound 1) has a very low cytostatic effect in evaluation using HER2-overexpressing cell lines.

Advantageous Effects of Invention

The present invention provides a novel compound of formula (I) or a salt thereof which is useful as a HER2 inhibitor.

The compound of the present invention or the salt thereof has been found to have excellent HER2-selective inhibitory activity and to exhibit a cytostatic effect on cancer cell lines. Furthermore, the compound of the present invention or the salt thereof selectively and strongly inhibits HER2 as compared with EGFR and can therefore be expected to be able to alleviate adverse effects and to improve safety. The compound of the present invention or the salt thereof is useful as a prophylactic and/or therapeutic agent for cancer.

DESCRIPTION OF EMBODIMENTS

The compound of formula (I) of the present invention is a compound having pyrazolo[3,4-d]pyrimidine as a basic structure and is a novel compound which has not been described in any of the literatures in the citation list, etc.

In the present specification, examples of the "substituent" include a halogen atom, a hydroxyl group, a cyano group, a nitro group, an alkyl group, a halogenoalkyl group, a cycloalkyl group, a cycloalkyl-alkyl group, an aralkyl group, an alkenyl group, an alkynyl group, an alkoxy group, a halogenoalkoxy group, a cycloalkoxy group, a cycloalkyl-alkoxy group, an aralkyloxy group, an alkylthio group, a cycloalkyl-alkylthio group, an amino group, a mono- or di-alkylamino group, a cycloalkyl-alkylamino group, an acyl group, an acyloxy group, an oxo group, a carboxyl group, an alkoxycarbonyl group, an aralkyloxycarbonyl group, a carbamoyl group, a saturated or unsaturated heterocyclic group, an aromatic hydrocarbon group, and a saturated heterocyclyloxy group. When the substituent is present, the number thereof is typically 1, 2, or 3.

In the present specification, examples of the "halogen atom" include a fluorine atom, a chlorine atom, a bromine atom, and an iodine atom.

In the present specification, the "alkyl group" may be linear or branched. Examples thereof include C1-C6 alkyl groups such as a methyl group, an ethyl group, a n-propyl group, an isopropyl group, a n-butyl group, an isobutyl group, a sec-butyl group, a tert-butyl group, a n-pentyl group, an isopentyl group, and a hexyl group.

In the present specification, the "halogenoalkyl group" is a linear or branched alkyl group having 1 to 6 carbon atoms and having 1 to 13 halogen atoms (halogeno-C1-C6 alkyl group). Examples thereof include halogeno-C1-C6 alkyl groups such as a fluoromethyl group, a difluoromethyl group, a trifluoromethyl group, a trichloromethyl group, a fluoroethyl group, a 1,1,1-trifluoroethyl group, a monofluoro-n-propyl group, a perfluoro-n-propyl group, and a perfluoroisopropyl group and preferably include halogeno-C1-C4 alkyl groups.

In the present specification, specific examples of the "cycloalkyl group" include C3-C7 cycloalkyl groups such as a cyclopropyl group, a cyclobutyl group, a cyclopentyl group, a cyclohexyl group, and a cycloheptyl group.

In the present specification, examples of the "cycloalkyl-alkyl group" include C3-C7 cycloalkyl-substituted C1-C4 alkyl groups such as a cyclopropylmethyl group, a cyclobutylmethyl group, a cyclopentylmethyl group, a cyclohexylmethyl group, and a cycloheptylmethyl group.

In the present specification, examples of the "aralkyl group" include C7-C13 aralkyl groups such as a benzyl group, a phenethyl group, a naphthylmethyl group, and a fluorenylmethyl group.

In the present specification, the "alkenyl group" may be linear, branched, or cyclic and means an unsaturated hydrocarbon group having at least one double bond. Examples thereof include C2-C6 alkenyl groups such as a vinyl group, an allyl group, a 1-propenyl group, a 2-methyl-2-propenyl group, an isopropenyl group, a 1-, 2-, or 3-butenyl group, a 2-, 3-, or 4-pentenyl group, a 2-methyl-2-butenyl group, a 3-methyl-2-butenyl group, a 5-hexenyl group, a 1-cyclopentenyl group, a 1-cyclohexenyl group, and a 3-methyl-3-butenyl group.

In the present specification, the "alkynyl group" may be linear, branched, or cyclic and means an unsaturated hydrocarbon group having at least one triple bond. Examples thereof include C2-C6 alkynyl groups such as an ethynyl group, a 1- or 2-propynyl group, a 1-, 2-, or 3-butynyl group, and a 1-methyl-2-propynyl group.

In the present specification, the "alkoxy group" may be linear or branched. Examples thereof include C1-C6 alkoxy groups such as a methoxy group, an ethoxy group, a n-propoxy group, an isopropoxy group, a n-butoxy group, an isobutoxy group, a sec-butoxy group, a tert-butoxy group, a pentyloxy group, an isopentyloxy group, and a hexyloxy group.

In the present specification, the "halogenoalkoxy group" is a linear or branched alkoxy group having 1 to 6 carbon atoms and having 1 to 13 halogen atoms (halogeno-C1-C6 alkoxy group). Examples thereof include halogeno-C1-C6 alkoxy groups such as a fluoromethoxy group, a difluoromethoxy group, a trifluoromethoxy group, a trichloromethoxy group, a fluoroethoxy group, a 1,1,1-trifluoroethoxy group, a monofluoro-n-propoxy group, a perfluoro-n-propoxy group, and a perfluoro-isopropoxy group and preferably include halogeno-C1-C4 alkoxy groups.

In the present specification, examples of the "cycloalkoxy group" include C3-C7 cycloalkoxy groups such as a cyclopropoxy group, a cyclobutoxy group, a cyclopentyloxy group, a cyclohexyloxy group, and a cycloheptyloxy group.

In the present specification, examples of the "cycloalkyl-alkoxy group" include C3-C7 cycloalkyl-substituted C1-C4 alkoxy groups such as a cyclopropylmethoxy group, a cyclobutylmethoxy group, a cyclopentylmethoxy group, a cyclohexylmethoxy group, and a cycloheptylmethoxy group.

In the present specification, examples of the "aralkyloxy group" include C7-C13 aralkyloxy groups such as a benzyloxy group, a phenethyloxy group, a naphthylmethyloxy group, and a fluorenylmethyloxy group.

In the present specification, the "alkylthio group" may be linear or branched. Examples thereof include C1-C6 alkylthio groups such as a methylthio group, an ethylthio group, a n-propylthio group, an isopropylthio group, a n-butylthio group, an isobutylthio group, a tert-butylthio group, a n-pentylthio group, an isopentylthio group, and a hexylthio group.

In the present specification, examples of the "cycloalkyl-alkylthio group" include C3-C7 cycloalkyl-substituted C1-C4 alkylthio groups such as a cyclopropylmethylthio group, a cyclobutylmethylthio group, a cyclopentylmethylthio group, a cyclohexylmethylthio group, and a cycloheptylmethylthio group.

In the present specification, examples of the "monoalkylamino group" include linear or branched C1-C6 alkyl group-monosubstituted amino groups such as a methylamino group, an ethylamino group, a n-propylamino group, an isopropylamino group, a n-butylamino group, an isobutylamino group, a tert-butylamino group, a n-pentylamino group, an isopentylamino group, and a hexylamino group.

In the present specification, examples of the "dialkylamino group" include linear or branched C1-C6 alkyl group-disubstituted amino groups such as a dimethylamino group, a diethylamino group, a di(n-propyl)amino group, a diisopropylamino group, a di(n-butyl)amino group, a diisobutylamino group, a di(tert-butyl)amino group, a di(n-pentyl)amino group, a diisopentylamino group, a dihexylamino group, a methylethylamino group, and a methylisopropylamino group.

In the present specification, examples of the "cycloalkyl-alkylamino group" include C3-C7 cycloalkyl-substituted C1-C4 alkylamino groups such as a cyclopropylmethyl-amino group, a cyclobutylmethylamino group, a cyclopentylmethylamino group, a cyclohexylmethylamino group, and a cycloheptylmethylamino group.

In the present specification, the "acyl group" means an alkylcarbonyl group or an arylcarbonyl group.

In the present specification, examples of the "alkylcarbonyl group" include linear or branched (C1-C6 alkyl)carbonyl groups such as a methylcarbonyl group, an ethylcarbonyl group, a n-propylcarbonyl group, an isopropylcarbonyl group, a n-butylcarbonyl group, an isobutylcarbonyl group, a tert-butylcarbonyl group, a n-pentylcarbonyl group, an isopentylcarbonyl group, and a hexylcarbonyl group.

In the present specification, examples of the "arylcarbonyl group" include (C6-C13 aryl)carbonyl groups such as a phenylcarbonyl group, a naphthylcarbonyl group, a fluorenylcarbonyl group, an anthrylcarbonyl group, a biphenylyl-carbonyl group, a tetrahydronaphthylcarbonyl group, a chromanylcarbonyl group, a 2,3-dihydro-1,4- dioxanaphthalenylcarbonyl group, an indanylcarbonyl group, and a phenanthrylcarbonyl group.

In the present specification, the "acyloxy group" means an alkylcarbonyloxy group or an arylcarbonyloxy group.

In the present specification, examples of the "alkylcarbonyloxy group" include linear or branched (C1-C6 alkyl)carbonyloxy groups such as a methylcarbonyloxy group, an ethylcarbonyloxy group, a n-propylcarbonyloxy group, an isopropylcarbonyloxy group, a n-butylcarbonyloxy group, an isobutylcarbonyloxy group, a tert-butylcarbonyloxy group, a n-pentylcarbonyloxy group, an isopentylcarbonyloxy group, and a hexylcarbonyloxy group.

In the present specification, examples of the "arylcarbonyloxy group" include (C6-C13 aryl)carbonyloxy groups such as a phenylcarbonyloxy group, a naphthylcarbonyloxy group, a fluorenylcarbonyloxy group, an anthrylcarbonyloxy group, a biphenylylcarbonyloxy group, a tetrahydronaphthylcarbonyloxy group, a chromanylcarbonyloxy group, a 2,3-dihydro-1,4-dioxanaphthalenylcarbonyloxy group, an indanylcarbonyloxy group, and a phenanthrylcarbonyloxy group.

In the present specification, the "alkoxycarbonyl group" may be linear or branched. Examples thereof include (C1-C6 alkoxy)carbonyl groups such as a methoxycarbonyl group, an ethoxycarbonyl group, a propoxycarbonyl group, an isopropoxycarbonyl group, a butoxycarbonyl group, an isobutoxycarbonyl group, a tert-butoxycarbonyl group, a pentyloxycarbonyl group, an isopentyloxycarbonyl group, and a hexyloxycarbonyl group.

In the present specification, examples of the "aralkyloxycarbonyl group" include (C7-C13 aralkyl)oxycarbonyl groups such as a benzyloxycarbonyl group, a phenethyloxycarbonyl group, a naphthylmethyloxycarbonyl group, and a fluorenylmethyloxycarbonyl group.

In the present specification, the "saturated heterocyclic group" is a saturated heterocyclic group having a heteroatom selected from the group consisting of a nitrogen atom, an oxygen atom, and a sulfur atom. Specific examples thereof include a morpholino group, a pyrrolidinyl group, a piperidinyl group, a piperazinyl group, a 4-methyl-1-piperazinyl group, a tetrahydrofuranyl group, a tetrahydropyranyl group, a tetrahydrothiophenyl group, a thiazolidinyl group, and an oxazolidinyl group.

In the present specification, the "unsaturated heterocyclic group" is a monocyclic or polycyclic fully unsaturated or partially unsaturated heterocyclic group having a heteroatom selected from the group consisting of a nitrogen atom, an oxygen atom, and a sulfur atom. Specific examples thereof include an imidazolyl group, a thienyl group, a furyl group, a pyrrolyl group, an oxazolyl group, an isoxazolyl group, a thiazolyl group, an isothiazolyl group, a thiadiazolyl group, a pyrazolyl group, a triazolyl group, a tetrazolyl group, a pyridyl group, a pyrazyl group, a pyrimidinyl group, a pyridazinyl group, an indolyl group, an isoindolyl group, an indazolyl group, a triazolopyridyl group, a benzimidazolyl group, a benzoxazolyl group, a benzothiazolyl group, a benzothienyl group, a benzofuranyl group, a purinyl group, a quinolyl group, an isoquinolyl group, a quinazolinyl group, a quinoxalinyl group, a methylenedioxyphenyl group, an ethylenedioxyphenyl group, and a dihydrobenzofuranyl group.

In the present specification, examples of the "aromatic hydrocarbon group" include C6-C14 aromatic hydrocarbon groups such as a phenyl group, a toluyl group, a xylyl group, a naphthyl group, an anthracenyl group, a phenanthryl group, a fluorenyl group, and a tetrahydronaphthyl group.

In the present specification, the "saturated heterocyclyloxy group" is a saturated heterocylyloxy group having a heteroatom selected from the group consisting of a nitrogen atom, an oxygen atom, and a sulfur atom. Specific examples thereof include a morpholinyloxy group, a 1-pyrrolidinyloxy group, a piperidinoxy group, a piperazinyloxy group, a 4-methyl-1-piperazinyloxy group, a tetrahydrofuranyloxy group, a tetrahydropyranyloxy group, a tetrahydrothiophenyloxy group, a thiazolidinyloxy group, and an oxazolidinyloxy group.

The term "CA-CB" in the description of a group in the present specification refers to a group having A to B carbon atoms. For example, the "C1-C6 alkyl group" refers to an alkyl group having 1 to 6 carbon atoms, and the "C6-C14 aromatic hydrocarbon oxy group" refers to an oxy group bonded to an aromatic hydrocarbon group having 6 to 14 carbon atoms. The term "A- to B-membered" means that the number of atoms constituting a ring (the number of ring members) is A to B. For example, the "4- to 10-membered saturated heterocyclic group" means a saturated heterocyclic group in which the number of ring members is 4 to 10.

In the compound of formula (I) of the present invention, X represents an optionally substituted 4- to 10-membered nitrogen-containing saturated heterocyclic group. In this context, the "4- to 10-membered nitrogen-containing saturated heterocyclic group" is a 4- to 10-membered saturated heterocyclic group containing at least one nitrogen atom in the ring and further containing 0 to 2 identical or different heteroatoms selected from the group consisting of an oxygen atom and a sulfur atom in the ring. Examples thereof include an azetidinyl group, a pyrrolidinyl group, a piperidinyl group, a piperazinyl group, a morpholinyl group, an octahydroquinolinylene group, and an octahydroindolylene group.

The 4- to 10-membered nitrogen-containing saturated heterocyclic group is preferably a 4- to 8-membered saturated heterocyclic group containing one nitrogen atom in the ring, more preferably a pyrrolidinyl group or a piperidinyl group, even more preferably a 1,3-pyrrolidinyl group or a 1,3-piperidinyl group, further preferably a 1,3-piperidinyl group.

Examples of the "substituent" which may be added to the 4- to 10-membered nitrogen-containing saturated heterocyclic group include the substituent as described above. The substituent is preferably a halogen atom, a hydroxyl group, a cyano group, a C1-C6 alkyl group, or an amino group, more preferably a halogen atom or a C1-C6 alkyl group, even more preferably a fluorine atom or a methyl group, further preferably a fluorine atom.

The optionally halogen atom- or C1-C6 alkyl group-substituted 4- to 10-membered nitrogen-containing saturated heterocyclic group is preferably an optionally halogen atom- or C1-C6 alkyl group-substituted pyrrolidinyl group, or an optionally halogen atom- or C1-C6 alkyl group-substituted piperidinyl group, more preferably an optionally C1-C6 alkyl group-substituted pyrrolidinyl group, or an optionally fluorine atom-substituted piperidinyl group, even more preferably a pyrrolidinyl group, a methylpyrrolidinyl group, a piperidinyl group, or a fluoropiperidinyl group, further preferably a piperidinyl group or a fluoropiperidinyl group.

In the compound of formula (I), X is preferably an optionally substituted 4- to 10-membered nitrogen-containing saturated heterocyclic group, more preferably a 4- to 10-membered nitrogen-containing saturated heterocyclic group optionally having a halogen atom, a hydroxyl group, a cyano group, a C1-C6 alkyl group, or an amino group as a substituent, even more preferably a 4- to 8-membered nitrogen-containing saturated heterocyclic group optionally having a halogen atom or a C1-C6 alkyl group as a substituent, further preferably a pyrrolidinyl group optionally having a halogen atom or a C1-C6 alkyl group as a substituent, or a piperidinyl group optionally having a halogen atom or a C1-C6 alkyl group as a substituent, still further preferably a pyrrolidinyl group optionally having a C1-C6 alkyl group as a substituent, or a piperidinyl group optionally having a halogen atom as a substituent, still further preferably a pyrrolidinyl group optionally having a methyl group as a substituent, or a piperidinyl group optionally having a fluorine atom as a substituent, still further preferably a piperidinyl group optionally having a fluorine atom as a substituent, still further preferably a piperidinyl group.

The nitrogen atom in the 4- to 10-membered nitrogen-containing saturated heterocyclic group represented by X is preferably bonded to the carbonyl group of —COY in the formula (I).

In the compound of formula (I) of the present invention, Y represents —C($R_4$)=C($R_5$)($R_6$). $R_4$, $R_5$, and $R_6$ will be mentioned later.

In the compound of formula (I) of the present invention, $Z_1$, $Z_2$, $Z_3$, and $Z_4$ are the same as or different from each other and each represent a hydrogen atom, a halogen atom, a cyano group, a C2-C6 alkenyl group, an optionally substituted C1-C6 alkoxy group, an optionally substituted C1-C6 alkyl group, an optionally substituted amino group, an optionally substituted C3-C7 cycloalkyl group, a C6-C14 aromatic hydrocarbon group, or a 4- to 14-membered unsaturated heterocyclic group, or $Z_1$ and $Z_2$, or $Z_3$ and $Z_4$ optionally form, together with the respective carbon atoms bonded thereto, a benzene ring or a 5- to 7-membered saturated or unsaturated heterocyclic ring.

The "C2-C6 alkenyl group" represented by $Z_1$, $Z_2$, $Z_3$, or $Z_4$ is preferably a vinyl group, a propenyl group, a butenyl group, a pentenyl group, a hexenyl group, a cyclopropenyl group, a cyclobutenyl group, a cyclopentenyl group, or a cyclohexenyl group, more preferably a vinyl group, a propenyl group, a butenyl group, a cyclopropenyl group, or a cyclobutenyl group, even more preferably a vinyl group, a 1-propenyl group, a 2-propenyl group, or an isopropenyl group, further preferably a vinyl group.

The "C1-C6 alkoxy group" in the "optionally substituted C1-C6 alkoxy group" represented by $Z_1$, $Z_2$, $Z_3$, or $Z_4$ is preferably a methoxy group, an ethoxy group, a propoxy group, a butoxy group, a pentyloxy group, or a hexyloxy group, more preferably a methoxy group, an ethoxy group, a propoxy group, or a butoxy group, even more preferably a methoxy group, an ethoxy group, a n-propoxy group, an isopropoxy group, a n-butoxy group, a sec-butoxy group, or a tert-butoxy group, further preferably a methoxy group.

Examples of the "substituent" for the "optionally substituted C1-C6 alkoxy group" represented by $Z_1$, $Z_2$, $Z_3$, or $Z_4$ include the substituent as described above. The substituent is preferably a halogen atom, more preferably a fluorine atom.

The "optionally substituted C1-C6 alkoxy group" represented by $Z_1$, $Z_2$, $Z_3$, or $Z_4$ is preferably an optionally halogen atom-substituted C1-C6 alkoxy group, more preferably an optionally fluorine atom-substituted C1-C6 alkoxy group, even more preferably an optionally fluorine atom-substituted methoxy group, an optionally fluorine atom-substituted ethoxy group, an optionally fluorine atom-substituted propoxy group, an optionally fluorine atom-substituted butoxy group, an optionally fluorine atom-substituted pentyloxy group, or an optionally fluorine atom-substituted hexyloxy group, further preferably an optionally fluorine atom-substituted methoxy group, an optionally fluorine atom-substituted ethoxy group, an optionally fluorine atom-substituted propoxy group, or an optionally fluorine atom-substituted butoxy group, still further preferably an optionally fluorine atom-substituted methoxy group, an optionally fluorine atom-substituted ethoxy group, an optionally fluorine atom-substituted n-propoxy group, an optionally fluorine atom-substituted isopropoxy group, an optionally fluorine atom-substituted n-butoxy group, an optionally fluorine atom-substituted sec-butoxy group, or an optionally fluorine atom-substituted tert-butoxy group, still further preferably a methoxy group optionally substituted by 1 or 2 fluorine atoms, an ethoxy group optionally substituted by 1 or 2 fluorine atoms, a n-propoxy group optionally substituted by 1 or 2 fluorine atoms, an isopropoxy group optionally substituted by 1 or 2 fluorine atoms, a n-butoxy group optionally substituted by 1 or 2 fluorine atoms, a sec-butoxy group optionally substituted by 1 or 2 fluorine atoms, or a tert-butoxy group optionally substituted by 1 or 2 fluorine atoms, particularly preferably a methoxy group, a fluoromethoxy group, or a difluoromethoxy group.

The "C1-C6 alkyl group" in the "optionally substituted C1-C6 alkyl group" represented by $Z_1$, $Z_2$, $Z_3$, or $Z_4$ is preferably a methyl group, an ethyl group, a propyl group, a butyl group, a pentyl group, or a hexyl group, more preferably a methyl group, an ethyl group, a n-propyl group, an isopropyl group, a n-butyl group, an isobutyl group, a sec-butyl group, or a tert-butyl group, further preferably a methyl group or an ethyl group.

Examples of the "substituent" for the "optionally substituted C1-C6 alkyl group" represented by $Z_1$, $Z_2$, $Z_3$, or $Z_4$ include the substituent as described above.

The "optionally substituted C1-C6 alkyl group" represented by $Z_1$, $Z_2$, $Z_3$, or $Z_4$ is preferably an unsubstituted C1-C6 alkyl group, more preferably a methyl group, an ethyl group, a propyl group, a butyl group, a pentyl group, or a hexyl group, further preferably a methyl group, an ethyl group, a n-propyl group, an isopropyl group, a n-butyl group, an isobutyl group, a sec-butyl group, or a tert-butyl group, particularly preferably a methyl group or an ethyl group.

Examples of the "substituent" for the "optionally substituted amino group" represented by $Z_1$, $Z_2$, $Z_3$, or $Z_4$ include the substituent as described above. The substituent is preferably an alkyl group, more preferably a C1-C6 alkyl group, even more preferably a methyl group, an ethyl group, a propyl group, a butyl group, a pentyl group, or a hexyl group, further preferably a methyl group, an ethyl group, a n-propyl group, an isopropyl group, a n-butyl group, an isobutyl group, a sec-butyl group, or a tert-butyl group, particularly preferably a methyl group.

The optionally substituted amino group represented by $Z_1$, $Z_2$, $Z_3$, or $Z_4$ is preferably a mono- or di-alkylamino group, more preferably a mono- or di(C1-C6 alkyl)amino group, even more preferably a di(C1-C6 alkyl)amino group, further preferably a di(C1-C4 alkyl)amino group, still further preferably a dimethylamino group.

The "C3-C7 cycloalkyl group" in the "optionally substituted C3-C7 cycloalkyl group" represented by $Z_1$, $Z_2$, $Z_3$, or $Z_4$ is preferably a cyclopropyl group, a cyclobutyl group, a cyclopentyl group, a cyclohexyl group, or a cycloheptyl group, more preferably a cyclopropyl group, a cyclobutyl group, a cyclopentyl group, or a cyclohexyl group, further preferably a cyclopropyl group.

Examples of the "substituent" for the "optionally substituted C3-C7 cycloalkyl group" represented by $Z_1$, $Z_2$, $Z_3$, or $Z_4$ include the substituent as described above.

The "optionally substituted C3-C7 cycloalkyl group" represented by $Z_1$, $Z_2$, $Z_3$, or $Z_4$ is preferably an unsubstituted C3-C7 cycloalkyl group, more preferably a cyclopropyl group, a cyclobutyl group, a cyclopentyl group, a cyclohexyl group, or a cycloheptyl group, further preferably a cyclopropyl group, a cyclobutyl group, a cyclopentyl group, or a cyclohexyl group, particularly preferably a cyclopropyl group.

The "C6-C14 aromatic hydrocarbon group" represented by $Z_1$, $Z_2$, $Z_3$, or $Z_4$ is preferably a phenyl group or a naphthyl group, more preferably a phenyl group.

The "unsaturated heterocyclic group" represented by $Z_1$, $Z_2$, $Z_3$, or $Z_4$ is a monocyclic or polycyclic fully unsaturated or partially unsaturated heterocyclic group having a heteroatom selected from the group consisting of a nitrogen atom, an oxygen atom, and a sulfur atom. Examples thereof include an imidazolyl group, a thienyl group, a furyl group, a pyrrolyl group, an oxazolyl group, an isoxazolyl group, a thiazolyl group, an isothiazolyl group, a thiadiazolyl group, a pyrazolyl group, a triazolyl group, a tetrazolyl group, a pyridyl group, a pyrazyl group, a pyrimidinyl group, a pyridazinyl group, an indolyl group, an isoindolyl group, an indazolyl group, a triazolopyridyl group, a benzimidazolyl group, a benzoxazolyl group, a benzothiazolyl group, a benzothienyl group, a benzofuranyl group, a purinyl group, a quinolyl group, an isoquinolyl group, a quinazolinyl group, a quinoxalinyl group, a methylenedioxyphenyl group, an ethylenedioxyphenyl group, and a dihydrobenzofuranyl group. The unsaturated heterocyclic group is preferably a monocyclic or bicyclic 4- to 14-membered unsaturated heterocyclic group having one heteroatom selected from the group consisting of a nitrogen atom, an oxygen atom, and a sulfur atom, more preferably a monocyclic 4- to 6-membered fully unsaturated heterocyclic group having one heteroatom selected from the group consisting of a nitrogen atom, an oxygen atom, and a sulfur atom, even more preferably a monocyclic 4- to 6-membered fully unsaturated heterocyclic group having one oxygen atom, further preferably a furyl group.

The "5- to 7-membered saturated or unsaturated heterocyclic ring" formed by $Z_1$ and $Z_2$, or $Z_3$ and $Z_4$, together with the carbon atoms bonded thereto, is a 5- to 7-membered saturated, fully unsaturated, or partially unsaturated heterocyclic ring having a heteroatom selected from the group consisting of a nitrogen atom, an oxygen atom, and a sulfur atom.

The number of the heteroatom in the ring is preferably from 0 to 2, more preferably from 1 or 2. The heteroatom is preferably a nitrogen atom and/or an oxygen atom.

The 5- to 7-membered saturated heterocyclic ring or unsaturated heterocyclic ring is preferably a pyrrole ring, a pyrazole ring, an imidazole ring, a pyridine ring, a pyrazine ring, a pyrimidine ring, or a dioxolane ring, more preferably a pyridine ring or a dioxolane ring.

The ring formed by $Z_1$ and $Z_2$, or $Z_3$ and $Z_4$, together with the respective carbon atoms bonded thereto, is also preferably a benzene ring.

In the compound of formula (I), $Z_1$, $Z_2$, $Z_3$, and $Z_4$ are preferably the same as or different from each other and each represent a hydrogen atom, a halogen atom, a cyano group, a C2-C6 alkenyl group, an optionally substituted C1-C6 alkoxy group, an optionally substituted C1-C6 alkyl group, an optionally substituted amino group, an optionally substituted C3-C7 cycloalkyl group, a C6-C14 aromatic hydrocarbon group, or a monocyclic or bicyclic 4- to 14-membered unsaturated heterocyclic group, or $Z_1$ and $Z_2$, or $Z_3$ and $Z_4$ optionally form, together with the respective carbon atoms bonded thereto, a benzene ring or a 5- to 7-membered saturated or unsaturated heterocyclic ring, more preferably are the same as or different from each other and each represent a hydrogen atom, a halogen atom, a cyano group, a C2-C6 alkenyl group, an optionally substituted C1-C6 alkoxy group, an optionally substituted C1-C6 alkyl group, an optionally substituted amino group, an optionally substituted C3-C7 cycloalkyl group, or a monocyclic or bicyclic 4- to 14-membered unsaturated heterocyclic group, or $Z_1$ and $Z_2$, or $Z_3$ and $Z_4$ optionally form, together with the respective carbon atoms bonded thereto, a benzene ring or a 5- to 7-membered saturated or unsaturated heterocyclic ring, even more preferably are the same as or different from each other and each represent a hydrogen atom, a halogen atom, a cyano group, a C2-C6 alkenyl group, an optionally substituted C1-C6 alkoxy group, a C1-C6 alkyl group, an optionally substituted amino group, a C3-C7 cycloalkyl group, or a monocyclic 4- to 6-membered unsaturated heterocyclic group having one heteroatom selected from the group consisting of a nitrogen atom, an oxygen atom, and a sulfur atom, or $Z_1$ and $Z_2$, or $Z_3$ and $Z_4$ optionally form, together with the respective carbon atoms bonded thereto, a benzene ring or a 5- to 7-membered saturated or unsaturated heterocyclic ring, further preferably are the same as or different from each other and each represent a hydrogen atom, a halogen atom, a cyano group, a C2-C6 alkenyl group, an optionally halogen atom-substituted C1-C6 alkoxy group, a C1-C6 alkyl group, an optionally C1-C6 alkyl group-substituted amino group, a C3-C7 cycloalkyl group, or a monocyclic 4- to 6-membered unsaturated heterocyclic group having one heteroatom selected from the group consisting of a nitrogen atom, an oxygen atom, and a sulfur atom, or $Z_1$ and $Z_2$, or $Z_3$ and $Z_4$ optionally form, together with the respective carbon atoms bonded thereto, a benzene ring or a 5- to 7-membered saturated or unsaturated heterocyclic ring, still further preferably are the same as or different from each other and each represent a hydrogen atom, a fluorine atom, a chlorine atom, a bromine atom, a cyano group, a C2-C6 alkenyl group, an optionally fluorine atom-substituted C1-C6 alkoxy group, a C1-C6 alkyl group, a mono- or di(C1-C6 alkyl)amino group, a C3-C7 cycloalkyl group, or a monocyclic 4- to 6-membered unsaturated heterocyclic group having one oxygen atom, or $Z_1$ and $Z_3$, or $Z_3$ and $Z_4$ optionally form, together with the respective carbon atoms bonded thereto, a benzene ring or a 5- to 7-membered saturated or unsaturated heterocyclic ring, still further preferably are the same as or different from each other and each represent a hydrogen atom, a fluorine atom, a chlorine atom, a bromine atom, a cyano group, a C2-C6 alkenyl group, a C1-C6 alkoxy group optionally substituted by 1 or 2 fluorine atoms, a C1-C6 alkyl group, a di(C1-C6 alkyl)amino group, a C3-C7 cycloalkyl group, or a monocyclic 4- to 6-membered unsaturated heterocyclic group having one oxygen atom, or $Z_1$ and $Z_2$, or $Z_3$ and $Z_4$ optionally form, together with the respective carbon atoms bonded thereto, a benzene ring or a 5- to 7-membered saturated or unsaturated heterocyclic ring, still further preferably are the same as or different from each other and each represent a hydrogen atom, a fluorine atom, a chlorine atom, a bromine atom, a cyano group, a vinyl group, a methoxy group, a fluoromethoxy group, a difluoromethoxy group, a methyl group, an ethyl group, a dimethylamino group, a cyclopropyl group, or a furyl group, or $Z_1$ and $Z_2$, or $Z_3$ and $Z_4$ optionally form, together with the respective carbon atoms bonded thereto, a benzene ring, a pyridine ring, or a dioxolane ring, still further preferably are the same as or different from each other and each represent a hydrogen atom, a fluorine atom, a chlorine atom, a bromine atom, a methoxy group, a fluoromethoxy group, a difluoromethoxy group, or a methyl group, or $Z_1$ and $Z_2$, or $Z_3$ and $Z_4$ optionally form, together with the respective carbon atoms bonded thereto, a benzene ring.

In the compound of formula (I) of the present invention, W represents —$CH_2$—, an oxygen atom, or —NH—. W is preferably —$CH_2$— or an oxygen atom, more preferably —$CH_2$—.

In the compound of formula (I) of the present invention, n represents an integer of from 0 to 2. n is preferably 0 or 1, more preferably 0.

In the compound of formula (I) of the present invention, $R_1$ represents an optionally substituted amino group. In this context, examples of the "substituent" which may be added to the amino group include the substituent as described above.

The optionally substituted amino group represented by $R_1$ is preferably an unsubstituted amino group.

In the compound of formula (I) of the present invention, $R_2$ and $R_3$ are the same as or different from each other and each represent a hydrogen atom, an optionally substituted C1-C6 alkoxy group, an optionally substituted C1-C6 alkyl group, or an optionally substituted C6-C14 aromatic hydrocarbon group, or $R_2$ and $R_3$ optionally form, together with the nitrogen atom bonded thereto, an optionally substituted 4- to 8-membered nitrogen-containing saturated heterocyclic group.

The "C1-C6 alkoxy group" in the "optionally substituted C1-C6 alkoxy group" represented by $R_2$ or $R_3$ is preferably a methoxy group, an ethoxy group, a n-propoxy group, an isopropoxy group, a n-butoxy group, an isobutoxy group, a sec-butoxy group, a tert-butoxy group, a pentyloxy group, or a hexyloxy group, more preferably a methoxy group, an ethoxy group, a n-propoxy group, an isopropoxy group, a n-butoxy group, an isobutoxy group, a sec-butoxy group, or a tert-butoxy group, further preferably a methoxy group.

Examples of the "substituent" for the optionally substituted C1-C6 alkoxy group represented by $R_2$ or $R_3$ include the substituent as described above.

The "optionally substituted C1-C6 alkoxy group" represented by $R_2$ or $R_3$ is preferably an unsubstituted C1-C6 alkoxy group, more preferably a methoxy group, an ethoxy group, a n-propoxy group, an isopropoxy group, a n-butoxy group, an isobutoxy group, a sec-butoxy group, a tert-butoxy group, a pentyloxy group, or a hexyloxy group, further preferably a methoxy group, an ethoxy group, a n-propoxy group, an isopropoxy group, a n-butoxy group, an isobutoxy group, a sec-butoxy group, or a tert-butoxy group, particularly preferably a methoxy group.

The "C1-C6 alkyl group" in the "optionally substituted C1-C6 alkyl group" represented by $R_2$ or $R_3$ is preferably a methyl group, an ethyl group, a n-propyl group, an isopropyl group, a n-butyl group, an isobutyl group, a sec-butyl group, a tert-butyl group, a pentyl group, or a hexyl group, more preferably a methyl group, an ethyl group, a n-propyl group, an isopropyl group, a n-butyl group, an isobutyl group, a sec-butyl group, or a tert-butyl group, further preferably a methyl group.

Examples of the "substituent" for the "optionally substituted C1-C6 alkyl group" represented by $R_2$ or $R_3$ include the substituent as described above. The substituent is preferably a C1-C6 alkoxy group, preferably a methoxy group, an ethoxy group, a n-propoxy group, an isopropoxy group, a n-butoxy group, an isobutoxy group, a sec-butoxy group, a tert-butoxy group, a pentyloxy group, or a hexyloxy group, more preferably a methoxy group, an ethoxy group, a n-propoxy group, an isopropoxy group, a n-butoxy group, an isobutoxy group, a sec-butoxy group, or a tert-butoxy group, further preferably a methoxy group or an ethoxy group.

The "optionally substituted C1-C6 alkyl group" represented by $R_2$ or $R_3$ is preferably an unsubstituted C1-C6 alkyl group or a C1-C6 alkoxy group-substituted C1-C6 alkyl group, more preferably an unsubstituted C1-C6 alkyl group, even more preferably a methyl group, an ethyl group, a n-propyl group, an isopropyl group, a n-butyl group, an isobutyl group, a sec-butyl group, a tert-butyl group, a pentyl group, or a hexyl group.

In the case of having a substituent, the number of the substituent is not particularly limited. When the substituent is a C1-C6 alkoxy group, the number thereof is preferably 1.

The "C6-C14 aromatic hydrocarbon group" in the "optionally substituted C6-C14 aromatic hydrocarbon group" represented by $R_2$ or $R_3$ is preferably a phenyl group or a naphthyl group, more preferably a phenyl group.

Examples of the "substituent" for the "optionally substituted C6-C14 aromatic hydrocarbon group" represented by $R_2$ or $R_3$ include the substituent as described above. The substituent is preferably a halogen atom. The optionally halogen atom-substituted C6-C14 aromatic hydrocarbon group is preferably an optionally fluorine atom- or chlorine atom-substituted phenyl group, more preferably a phenyl group, a fluorophenyl group, a difluorophenyl group, a trifluorophenyl group, a chlorophenyl group, a dichlorophenyl group, or a trichlorophenyl group, even more preferably a phenyl group.

The "4- to 8-membered nitrogen-containing saturated heterocyclic group" in the "optionally substituted 4- to 8-membered nitrogen-containing saturated heterocyclic group" formed by $R_2$ and $R_3$, together with the nitrogen atom bonded thereto, is a 4- to 8-membered saturated heterocyclic group containing at least one nitrogen atom in the ring and further containing 0 to 2 identical or different heteroatoms selected from the group consisting of an oxygen atom and a sulfur atom in the ring.

The 4- to 8-membered nitrogen-containing saturated heterocyclic group is preferably a 4- to 8-membered saturated heterocyclic group containing one nitrogen atom, more preferably an azetidinyl group, a pyrrolidinyl group, or a piperidinyl group.

Examples of the "substituent" for the "optionally substituted 4- to 8-membered nitrogen-containing saturated heterocyclic group" include the substituent as described above. The substituent is preferably a hydroxyl group.

The optionally substituted 4- to 8-membered nitrogen-containing saturated heterocyclic group is preferably an optionally hydroxyl group-substituted 4- to 8-membered nitrogen-containing saturated heterocyclic group, more preferably an azetidinyl group, a pyrrolidinyl group, a piperidinyl group, a hydroxyazetidinyl group, a hydroxypyrrolidinyl group, or a hydroxypiperidinyl group, even more preferably a pyrrolidinyl group, a piperidinyl group, or a hydroxyazetidinyl group.

In the compound of formula (I), $R_2$ and $R_3$ are preferably the same as or different from each other and each represent a hydrogen atom, an optionally substituted C1-C6 alkoxy group, an optionally substituted C1-C6 alkyl group, or an optionally substituted C6-C14 aromatic hydrocarbon group, or $R_2$ and $R_3$ optionally form, together with the nitrogen atom bonded thereto, an optionally substituted 4- to 8-membered nitrogen-containing saturated heterocyclic group, more preferably are the same as or different from each other and each represent a hydrogen atom, a C1-C6 alkoxy group, a C1-C6 alkyl group optionally having a C1-C6 alkoxy group as a substituent, or a C6-C14 aromatic hydrocarbon group optionally having a halogen atom as a substituent, or $R_2$ and $R_3$ optionally form, together with the nitrogen atom bonded thereto, an optionally substituted 4- to 8-membered nitrogen-containing saturated heterocyclic group, even more preferably are the same as or different from each other and each represent a hydrogen atom, a C1-C6 alkoxy group, a C1-C6 alkyl group, or a C6-C14 aromatic hydrocarbon group, or $R_2$ and $R_3$ optionally form, together with the nitrogen atom bonded thereto, a 4- to 8-membered nitrogen-containing saturated heterocyclic group optionally having a hydroxyl group as a substituent, further preferably are the same as or different from each other and each represent a C1-C6 alkoxy group, a C1-C6 alkyl group, or a C6-C14 aromatic hydrocarbon group, or $R_2$ and $R_3$ optionally form, together with the nitrogen atom bonded thereto, a 4- to 8-membered nitrogen-containing saturated heterocyclic group optionally having a hydroxyl group as a substituent, still further preferably are the same as or different from each other and each represent a methoxy group, a methyl group, or a phenyl group, or $R_2$ and $R_3$ optionally form, together with the nitrogen atom bonded thereto, an azetidinyl group optionally having a hydroxyl group as a substituent, a pyrrolidinyl group, or a piperidinyl group, still further preferably are the same as or different from each other and each represent a methoxy group, a methyl group, or a phenyl group, or $R_2$ and $R_3$ optionally form, together with the nitrogen atom bonded thereto, a hydroxyazetidinyl group, a pyrrolidinyl group, or a piperidinyl group, still further preferably each are a methyl group.

In the compound of formula (I) of the present invention, $R_4$, $R_5$, and $R_6$ are the same as or different from each other and each represent a hydrogen atom or an optionally substituted C1-C6 alkyl group.

The "C1-C6 alkyl group" in the "optionally substituted C1-C6 alkyl group" represented by $R_4$, $R_5$, or $R_6$ is preferably a methyl group, an ethyl group, a n-propyl group, an isopropyl group, a n-butyl group, an isobutyl group, a sec-butyl group, a tert-butyl group, a pentyl group, or a hexyl group, more preferably a methyl group, an ethyl group, a n-propyl group, an isopropyl group, a n-butyl group, an isobutyl group, a sec-butyl group, or a tert-butyl group, further preferably a methyl group, an ethyl group, a n-propyl group, or an isopropyl group, particularly preferably a methyl group.

Examples of the "substituent" for the "optionally substituted C1-C6 alkyl group" represented by $R_4$, $R_5$, or $R_6$ include the substituent as described above. The substituent is preferably a dialkylamino group or a saturated heterocyclic group, more preferably a di(C1-C6 alkyl)amino group or a 4- to 8-membered saturated heterocyclic group having a nitrogen atom, even more preferably a di(C1-C4 alkyl) amino group or a 4- to 8-membered saturated heterocyclic group having a nitrogen atom, further preferably a dimethylamino group, a methylethylamino group, a diethylamino group, a methylisopropylamino group, a 1-piperidinyl group, or a 1-pyrrolidinyl group, particularly preferably a dimethylamino group.

The number of the substituent is not particularly limited and is preferably 1.

The "optionally substituted C1-C6 alkyl group" represented by $R_4$, $R_5$, or $R_1$ is preferably a C1-C6 alkyl group optionally having, as a substituent, a di(C1-C6 alkyl)amino group or a 4- to 8-membered saturated heterocyclic group having a nitrogen atom, more preferably a C1-C4 alkyl group optionally having, as a substituent, a di(C1-C4 alkyl) amino group or a 4- to 8-membered saturated heterocyclic group having a nitrogen atom, even more preferably a methyl group, an ethyl group, a n-propyl group, an isopropyl group, a n-butyl group, an isobutyl group, a sec-butyl group, a tert-butyl group, a dimethylaminomethyl group, a methylethylaminomethyl group, a diethylaminomethyl group, a methylisopropylaminomethyl group, a dimethylaminoethyl group, a diethylaminoethyl group, a 1-piperidinylmethyl group, or a 1-pyrrolidinylmethyl group, further preferably a methyl group, an ethyl group, a n-propyl group, an isopropyl group, a n-butyl group, an isobutyl group, a sec-butyl group, a tert-butyl group, a dimethylaminomethyl group, a methylethylaminomethyl group, a diethylaminomethyl group, a methylisopropylaminomethyl group, a dimethylaminoethyl group, or a diethylaminoethyl group, still further preferably a methyl group, a dimethylaminomethyl group, a methylethylaminomethyl group, a diethylaminomethyl group, or a methylisopropylaminomethyl group, particularly preferably a dimethylaminomethyl group.

In the compound of formula (I), $R_4$, $R_5$, and $R_4$ are the same as or different from each other and each are preferably a hydrogen atom or an optionally substituted C1-C6 alkyl group, more preferably a hydrogen atom or a C1-C6 alkyl group optionally having, as a substituent, a di(C1-C6 alkyl) amino group or a 4- to 8-membered saturated heterocyclic group having a nitrogen atom, even more preferably a hydrogen atom or a C1-C4 alkyl group optionally having, as a substituent, a di(C1-C4 alkyl)amino group or a 4- to 8-membered saturated heterocyclic group having a nitrogen atom, further preferably a hydrogen atom, a methyl group, an ethyl group, a n-propyl group, an isopropyl group, a n-butyl group, an isobutyl group, a sec-butyl group, a tert-butyl group, a dimethylaminomethyl group, a methylethylaminomethyl group, a diethylaminomethyl group, a methylisopropylaminomethyl group, a dimethylaminoethyl group, a diethylaminoethyl group, a 1-piperidinylmethyl group, or a 1-pyrrolidinylmethyl group, still further preferably a hydrogen atom, a methyl group, an ethyl group, a n-propyl group, an isopropyl group, a n-butyl group, an isobutyl group, a sec-butyl group, a tert-butyl group, a dimethylaminomethyl group, a methylethylaminomethyl group, a diethylaminomethyl group, a methylisopropylaminomethyl group, a dimethylaminoethyl group, or a diethylaminoethyl group, still further preferably a hydrogen atom, a methyl group, a dimethylaminomethyl group, a methylethylaminomethyl group, a diethylaminomethyl group, or a methylisopropylaminomethyl group, particularly preferably a hydrogen atom or a dimethylaminomethyl group.

In the compound of formula (I), $-C(R_4)=C(R_5)(R_6)$ represented by Y is preferably

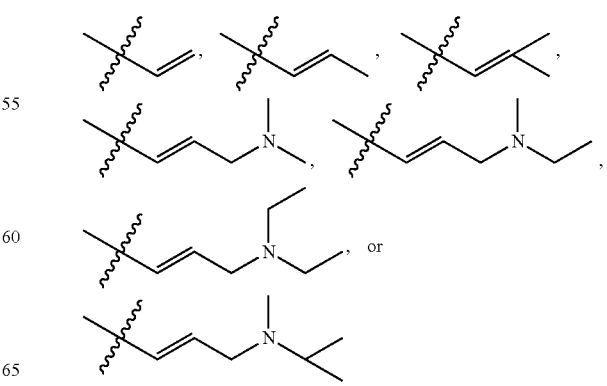

particularly preferably

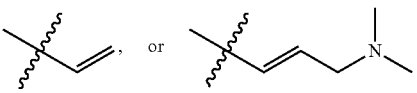

A compound preferred as the compound of the present invention of formula (I) is a compound or a salt thereof, wherein
X is an optionally substituted 4- to 10-membered nitrogen-containing saturated heterocyclic group;
Y is —C($R_4$)═C($R_5$)($R_6$);
$Z_1$, $Z_2$, $Z_3$, and $Z_4$ are the same as or different from each other and each are a hydrogen atom, a halogen atom, a cyano group, a C2-C6 alkenyl group, an optionally substituted C1-C6 alkoxy group, an optionally substituted C1-C6 alkyl group, an optionally substituted amino group, an optionally substituted C3-C7 cycloalkyl group, a C6-C14 aromatic hydrocarbon group, or a 4- to 14-membered unsaturated heterocyclic group, or $Z_1$ and $Z_2$, or $Z_3$ and $Z_4$ optionally form, together with the respective carbon atoms bonded thereto, a benzene ring or a 5- to 7-membered saturated or unsaturated heterocyclic ring;
W is —$CH_2$—, an oxygen atom, or —NH—;
n is an integer of from 0 to 2;
$R_1$ is an optionally substituted amino group;
$R_2$ and $R_3$ are the same as or different from each other and each are a hydrogen atom, an optionally substituted C1-C6 alkoxy group, an optionally substituted C1-C6 alkyl group, or an optionally substituted C6-C14 aromatic hydrocarbon group, or $R_2$ and $R_3$ optionally form, together with the nitrogen atom bonded thereto, a 4- to 8-membered nitrogen-containing saturated heterocyclic group optionally having a hydroxyl group as a substituent; and
$R_4$, $R_5$, and $R_6$ are the same as or different from each other and each are a hydrogen atom or an optionally substituted C1-C6 alkyl group.

A compound more preferred as the compound of the present invention of formula (I) is a compound or a salt thereof, wherein
X is a 4- to 10-membered nitrogen-containing saturated heterocyclic group optionally having a halogen atom, a hydroxyl group, a cyano group, a C1-C6 alkyl group, or an amino group as a substituent;
Y is —C($R_4$)═C($R_5$)($R_6$);
$Z_1$, $Z_2$, $Z_3$, and $Z_4$ are the same as or different from each other and each are a hydrogen atom, a halogen atom, a cyano group, a C2-C6 alkenyl group, an optionally substituted C1-C6 alkoxy group, an optionally substituted C1-C6 alkyl group, an optionally substituted amino group, an optionally substituted C3-C7 cycloalkyl group, or a 4- to 14-membered unsaturated heterocyclic group, or $Z_1$ and $Z_3$, or $Z_3$ and $Z_4$ optionally form, together with the respective carbon atoms bonded thereto, a benzene ring or a 5- to 7-membered saturated or unsaturated heterocyclic ring;
W is —$CH_2$—, an oxygen atom, or —NH—;
n is 0;
$R_1$ is an amino group;
$R_2$ and $R_3$ are the same as or different from each other and each are a hydrogen atom, an optionally substituted C1-C6 alkoxy group, an optionally substituted C1-C6 alkyl group, or an optionally substituted C6-C14 aromatic hydrocarbon group, or $R_2$ and $R_3$ optionally form, together with the nitrogen atom bonded thereto, a 4- to 8-membered nitrogen-containing saturated heterocyclic group optionally having a hydroxyl group as a substituent; and
$R_4$, $R_5$, and $R_5$ are the same as or different from each other and each are a hydrogen atom or an optionally substituted C1-C6 alkyl group.

A compound more preferred as the compound of the present invention of formula (I) is a compound or a salt thereof, wherein
X is a 4- to 8-membered nitrogen-containing saturated heterocyclic group optionally having a halogen atom or a C1-C6 alkyl group as a substituent;
Y is —C($R_4$)═C($R_5$)($R_6$);
$Z_1$, $Z_2$, $Z_3$, and $Z_4$ are the same as or different from each other and each are a hydrogen atom, a halogen atom, a cyano group, a C2-C6 alkenyl group, an optionally halogen atom-substituted C1-C6 alkoxy group, a C1-C6 alkyl group, an optionally C1-C6 alkyl group-substituted amino group, a C3-C7 cycloalkyl group, or a monocyclic 4- to 6-membered unsaturated heterocyclic group having one oxygen atom, or $Z_1$ and $Z_2$, or $Z_3$ and $Z_4$ optionally form, together with the respective carbon atoms bonded thereto, a benzene ring or a 5- to 7-membered saturated or unsaturated heterocyclic ring;
W is —$CH_2$—, an oxygen atom, or —NH—;
n is 0;
$R_1$ is an amino group;
$R_2$ and $R_3$ are the same as or different from each other and each are a hydrogen atom, a C1-C6 alkoxy group, a C1-C6 alkyl group, or a C6-C14 aromatic hydrocarbon group, or $R_2$ and $R_3$ optionally form, together with the nitrogen atom bonded thereto, an optionally hydroxyl group-substituted 4- to 8-membered nitrogen-containing saturated heterocyclic group; and
$R_4$, $R_5$, and $R_6$ are the same as or different from each other and each are a hydrogen atom or an optionally di(C1-C6 alkyl)amino group-substituted C1-C6 alkyl group.

A compound more preferred as the compound of the present invention of formula (I) is a compound or a salt thereof, wherein
X is a pyrrolidinyl group optionally having a C1-C6 alkyl group as a substituent, or a piperidinyl group optionally having a halogen atom as a substituent;
Y is —C($R_4$)═C($R_5$) $R_6$);
$Z_1$, $Z_2$, $Z_3$, and $Z_4$ are the same as or different from each other and each are a hydrogen atom, a halogen atom, a cyano group, a C2-C6 alkenyl group, an optionally halogen atom-substituted C1-C6 alkoxy group, a C1-C6 alkyl group, an optionally C1-C6 alkyl group-substituted amino group, a C3-C7 cycloalkyl group, or a monocyclic 4- to 6-membered unsaturated heterocyclic group having one oxygen atom, or $Z_1$ and $Z_2$, or $Z_3$ and $Z_4$ optionally form, together with the respective carbon atoms bonded thereto, a benzene ring or a 5- to 7-membered saturated or unsaturated heterocyclic ring;
W is —$CH_2$—, an oxygen atom, or —NH—;
n is 0;
$R_1$ is an amino group;
$R_2$ and $R_3$ are the same as or different from each other and each are a hydrogen atom, a C1-C6 alkoxy group, a C1-C6 alkyl group, or a C6-C14 aromatic hydrocarbon group, or $R_2$ and $R_3$ optionally form, together with the nitrogen atom bonded thereto, an optionally hydroxyl group-substituted 4- to 8-membered nitrogen-containing saturated heterocyclic group; and
$R_4$, $R_5$, and $R_6$ are the same as or different from each other and each are a hydrogen atom or a dimethylaminomethyl group.

A compound more preferred as the compound of the present invention of formula (I) is a compound or a salt thereof, wherein
X is a pyrrolidinyl group, a methylpyrrolidinyl group, a piperidinyl group, or a fluoropiperidinyl group;
Y is

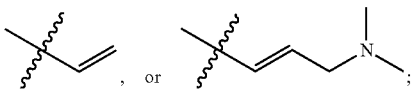

$Z_1$, $Z_2$, $Z_3$, and $Z_4$ are the same as or different from each other and each are a hydrogen atom, a fluorine atom, a chlorine atom, a bromine atom, a cyano group, a vinyl group, a methoxy group optionally having a fluorine atom as a substituent, a methyl group, an ethyl group, a dimethylamino group, a cyclopropyl group, or a furyl group, or $Z_3$ and $Z_4$ optionally form, together with the respective carbon atoms bonded thereto, a benzene ring, a pyridine ring, or a dioxolane ring;
W is —$CH_2$—, an oxygen atom, or —NH—;
n is 0;
$R_1$ is an amino group; and
$R_2$ and $R_3$ are the same as or different from each other and each are a hydrogen atom, a methoxy group, a methyl group, or a phenyl group, or $R_2$ and $R_3$ optionally form, together with the nitrogen atom bonded thereto, an azetidinyl group optionally having a hydroxyl group as a substituent, a pyrrolidinyl group, or a piperidinyl group.

A compound more preferred as the compound of the present invention of formula (I) is a compound or a salt thereof, wherein
X is a pyrrolidinyl group, a methylpyrrolidinyl group, a piperidinyl group, or a fluoropiperidinyl group;
Y is

$Z_1$, $Z_2$, $Z_3$, and $Z_4$ are the same as or different from each other and each are a hydrogen atom, a fluorine atom, a chlorine atom, a bromine atom, a cyano group, a vinyl group, a methoxy group, a fluoromethoxy group, a difluoromethoxy group, a methyl group, an ethyl group, a dimethylamino group, a cyclopropyl group, or a furyl group, or $Z_1$ and $Z_2$, or $Z_3$ and $Z_4$ optionally form, together with the respective carbon atoms bonded thereto, a benzene ring, a pyridine ring, or a dioxolane ring;
W is —$CH_2$—, an oxygen atom, or —NH—;
n is 0;
$R_1$ is an amino group; and
$R_2$ and $R_3$ are the same as or different from each other and each are a methoxy group, a methyl group, or a phenyl group, or $R_2$ and $R_3$ optionally form, together with the nitrogen atom bonded thereto, a hydroxyazetidinyl group, a pyrrolidinyl group, or a piperidinyl group.

A compound more preferred as the compound of the present invention of formula (I) is a compound or a salt thereof, wherein
X is a pyrrolidinyl group, a methylpyrrolidinyl group, a piperidinyl group, or a fluoropiperidinyl group;
Y is

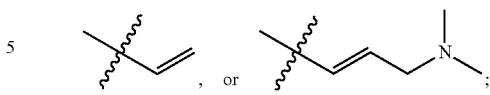

$Z_1$, $Z_2$, $Z_3$, and $Z_4$ are the same as or different from each other and each are a hydrogen atom, a fluorine atom, a chlorine atom, a bromine atom, a cyano group, a vinyl group, a methoxy group, a fluoromethoxy group, a difluoromethoxy group, a methyl group, an ethyl group, a dimethylamino group, a cyclopropyl group, or a furyl group, or $Z_1$ and $Z_2$, or $Z_3$ and $Z_4$ optionally form, together with the respective carbon atoms bonded thereto, a benzene ring, a pyridine ring, or a dioxolane ring;
W is —$CH_2$— or an oxygen atom;
n is 0;
$R_1$ is an amino group; and
$R_2$ and $R_3$ are the same as or different from each other and each are a methoxy group, a methyl group, or a phenyl group, or $R_2$ and $R_3$ optionally form, together with the nitrogen atom bonded thereto, a hydroxyazetidinyl group, a pyrrolidinyl group, or a piperidinyl group.

A compound more preferred as the compound of the present invention of formula (I) is a compound or a salt thereof, wherein
X is a pyrrolidinyl group, a methylpyrrolidinyl group, a piperidinyl group, or a fluoropiperidinyl group;
Y is

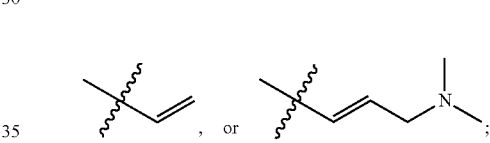

$Z_1$, $Z_2$, $Z_3$, and $Z_4$ are the same as or different from each other and each are a hydrogen atom, a fluorine atom, a chlorine atom, a bromine atom, a cyano group, a vinyl group, a methoxy group, a fluoromethoxy group, a difluoromethoxy group, a methyl group, an ethyl group, a dimethylamino group, a cyclopropyl group, or a furyl group, or $Z_1$ and $Z_2$, or $Z_3$ and $Z_4$ optionally form, together with the respective carbon atoms bonded thereto, a benzene ring, a pyridine ring, or a dioxolane ring;
W is —$CH_2$— or an oxygen atom;
n is 0;
$R_1$ is an amino group; and
each of $R_2$ and $R_3$ is a methyl group.

A compound more preferred as the compound of the present invention of formula (I) is a compound or a salt thereof, wherein
X is a piperidinyl group or a fluoropiperidinyl group;
Y is

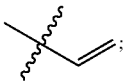 [SMILES: *C=C]

$Z_1$, $Z_2$, $Z_3$, and $Z_4$ are the same as or different from each other and each are a hydrogen atom, a fluorine atom, a chlorine atom, a bromine atom, a cyano group, a vinyl group, a methoxy group, a fluoromethoxy group, a difluoromethoxy group, a methyl group, an ethyl group, a dimethylamino group, a cyclopropyl group, or a furyl group, or $Z_1$ and $Z_2$, or $Z_3$ and $Z_4$ optionally form, together with the respective carbon atoms bonded thereto, a benzene ring, a pyridine ring, or a dioxolane ring;

W is —CH$_2$— or an oxygen atom;

n is 0;

R$_2$ is an amino group; and each of R$_2$ and R$_3$ is a methyl group.

A compound more preferred as the compound of the present invention of formula (I) is a compound or a salt thereof, wherein X is a piperidinyl group;

Y is

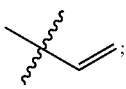 [SMILES: *C=C]

$Z_1$, $Z_2$, $Z_3$, and $Z_4$ are the same as or different from each other and each are a hydrogen atom, a fluorine atom, a chlorine atom, a bromine atom, a methoxy group, a fluoromethoxy group, a difluoromethoxy group, or a methyl group, or $Z_1$ and $Z_2$, or $Z_3$ and $Z_4$ optionally form, together with the respective carbon atoms bonded thereto, a benzene ring;

W is —CH$_2$—;

n is 0;

R$_1$ is an amino group; and each of R$_2$ and R$_3$ is a methyl group.

Specific examples of the compound of the present invention can include, but are not limited to, Example compounds 1 to 79 produced in Examples mentioned later.

Among them, preferred examples of the compound of the present invention can include the following:

(1) (R)-1-(1-acryloylpiperidin-3-yl)-4-amino-N-(5-bromo-4-(2-(dimethylamino)-2-oxoethyl)-2-methylphenyl)-1H-pyrazolo[3,4-d]pyrimidine-3-carboxamide, (2) (R)-1-(1-acryloylpiperidin-3-yl)-4-amino-N-(2-chloro-4-(2-(dimethylamino)-2-oxoethyl)-5-methylphenyl)-1H-pyrazolo[3,4-d]pyrimidine-3-carboxamide, (3) (R)-1-(1-acryloylpiperidin-3-yl)-4-amino-N-(2-chloro-4-(2-(dimethylamino)-2-oxoethyl)-3-methylphenyl)-1H-pyrazolo[3,4-d]pyrimidine-3-carboxamide, (4) (R)-1-(1-acryloylpiperidin-3-yl)-4-amino-N-(4-(2-(dimethylamino)-2-oxoethyl)-2-methylphenyl)-1H-pyrazolo[3,4-d]pyrimidine-3-carboxamide, (5) (R)-1-(1-acryloylpiperidin-3-yl)-4-amino-N-(4-(2-(dimethylamino)-2-oxoethyl)naphthalen-1-yl)-1H-pyrazolo[3,4-d]pyrimidine-3-carboxamide, (6) (R)-1-(1-acryloylpiperidin-3-yl)-4-amino-N-(2-chloro-4-(2-(dimethylamino)-2-oxoethyl)phenyl)-1H-pyrazolo[3,4-d]pyrimidine-3-carboxamide, (7) (R)-1-(1-acryloylpiperidin-3-yl)-4-amino-N-(4-(2-(dimethylamino)-2-oxoethyl)-2-methoxyphenyl)-1H-pyrazolo[3,4-d]pyrimidine-3-carboxamide, (8) (R)-1-(1-acryloylpiperidin-3-yl)-4-amino-N-(3-chloro-4-(2-(dimethylamino)-2-oxoethyl)phenyl)-1H-pyrazolo[3,4-d]pyrimidine-3-carboxamide, (9) (R)-1-(1-acryloylpiperidin-3-yl)-4-amino-N-(5-chloro-4-(2-(dimethylamino)-2-oxoethyl)-2-methoxyphenyl)-1H-pyrazolo[3,4-d]pyrimidine-3-carboxamide,

(10) (R)-1-(1-acryloylpiperidin-3-yl)-4-amino-N-(4-(2-(dimethylamino)-2-oxoethyl)-5-fluoro-2-methylphenyl)-1H-pyrazolo[3,4-d]pyrimidine-3-carboxamide,

(11) (R)-1-(1-acryloylpiperidin-3-yl)-4-amino-N-(3-chloro-4-(2-(dimethylamino)-2-oxoethyl)-2-methoxyphenyl)-1H-pyrazolo[3,4-d]pyrimidine-3-carboxamide,

(12) (R)-1-(1-acryloylpiperidin-3-yl)-4-amino-N-(4-(2-(dimethylamino)-2-oxoethyl)-3-fluoro-2-methylphenyl)-1H-pyrazolo[3,4-d]pyrimidine-3-carboxamide,

(13) (R)-1-(1-acryloylpiperidin-3-yl)-4-amino-N-(4-(2-(dimethylamino)-2-oxoethyl)-2,3-dimethylphenyl)-1H-pyrazolo[3,4-d]pyrimidine-3-carboxamide,

(14) (R)-1-(1-acryloylpiperidin-3-yl)-4-amino-N-(4-(2-(dimethylamino)-2-oxoethyl)-3-fluoro-2-methoxyphenyl)-1H-pyrazolo[3,4-d]pyrimidine-3-carboxamide,

(15) (R)-1-(1-acryloylpiperidin-3-yl)-4-amino-N-(2-(difluoromethoxy)-4-(2-(dimethylamino)-2-oxoethyl)phenyl)-1H-pyrazolo[3,4-d]pyrimidine-3-carboxamide,

(16) (R)-1-(1-acryloylpiperidin-3-yl)-4-amino-N-(4-(2-(dimethylamino)-2-oxoethyl)-2-(fluoromethoxy)phenyl)-1H-pyrazolo[3,4-d]pyrimidine-3-carboxamide,

(17) (R)-1-(1-acryloylpiperidin-3-yl)-4-amino-N-(2-bromo-4-(2-(dimethylamino)-2-oxoethyl)phenyl)-1H-pyrazolo[3,4-d]pyrimidine-3-carboxamide,

(18) (R)-1-(1-acryloylpiperidin-3-yl)-4-amino-N-(2-chloro-4-(2-(dimethylamino)-2-oxoethyl)-5-fluorophenyl)-1H-pyrazolo[3,4-d]pyrimidine-3-carboxamide,

(19) (R)-1-(1-acryloylpiperidin-3-yl)-4-amino-N-(5-chloro-4-(2-(dimethylamino)-2-oxoethyl)-2-methylphenyl)-1H-pyrazolo[3,4-d]pyrimidine-3-carboxamide, and

(20) (R)-1-(1-acryloylpiperidin-3-yl)-4-amino-N-(2,5-dichloro-4-(2-(dimethylamino)-2-oxoethyl)phenyl)-1H-pyrazolo[3,4-d]pyrimidine-3-carboxamide.

Next, the method for producing the compound according to the present invention will be described.

The compound (I) of the present invention can be produced by, for example, a production method given below or method shown in Examples. However, the method for producing the compound (I) of the present invention is not limited to these reaction examples.

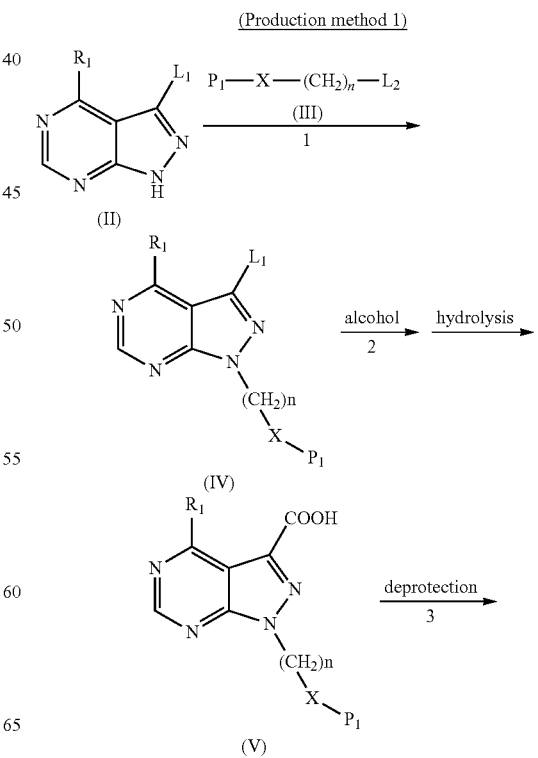

(Production method 1)

-continued (VI) → (VII)

wherein $L_1$ and $L_2$ are the same as or different from each other and each represent a leaving group; $P_1$ represents a protective group for the amino group contained in X; and X, Y, and n are as defined above.

(1st Step)

This step is a step of producing a compound of formula (IV) using compounds of formula (II) and the formula (III).

In the formula (II), the leaving group represented by $L_1$ is preferably a bromine atom or an iodine atom. This compound is a commercially available product or can be produced according to a method known in the art.

In the formula (III), examples of the leaving group of $L_2$ include a chlorine atom, a bromine atom, an iodine atom, methanesulfonate, and p-toluenesulfonate. This compound is a commercially available product or can be produced according to a method known in the art.

The compound of formula (III) can be used at from 1 to 10 mol, preferably from 1 to 5 mol, with respect to 1 mol of the compound of formula (II).

When the compound of formula (III) is used as an alkylation reagent, this step can be carried out in the presence of a base.

Examples of the base include: inorganic bases such as sodium bicarbonate, sodium carbonate, potassium carbonate, cesium carbonate, cesium hydroxide, sodium hydride, and potassium hydride; and organic amines such as trimethylamine, triethylamine, tripropylamine, diisopropylethylamine, N-methylmorpholine, pyridine, 4-(N,N-dimethylamino)pyridine, lutidine, and collidine. Potassium carbonate is preferred.

The amount of the base used can be from 1 to 100 mol, preferably from 2 to 10 mol, with respect to 1 mol of the compound of formula (II).

Examples of the solvent include: aprotic polar solvents such as N,N-dimethylformamide, N,N-dimethylacetamide, dimethyl sulfoxide, and N-methylpyrrolidin-2-one; ethers such as tetrahydrofuran and 1,4-dioxane; and nitriles such as acetonitrile. These solvents can be used alone or as a mixture. N,N-Dimethylacetamide is preferred.

The reaction time is preferably from 0.1 to 100 hours, more preferably from 0.5 to 24 hours. The reaction temperature is preferably from 0° C. to the boiling temperature of the solvent, more preferably from 0 to 100° C.

Thus-obtained compound of formula (IV) can be isolated and purified by a separation and purification approach known in the art mentioned later or can be subjected to a subsequent step without being isolated and purified.

(2nd Step)

This step is a step of producing a compound of formula (V) by reacting the compound of formula (IV) with, for example, a transition metal and, if necessary, a base, in a solvent which has no side reaction in the presence of an alcohol in a carbon monoxide atmosphere.

In this step, the pressure of the carbon monoxide is usually from 1 atm to 10 atm, preferably from 1 atm to 5 atm.

The amount of the alcohol compound used can be from 1 to 10 mol, preferably from 1 to 5 mol, with respect to 1 mol of the compound of formula (IV). Examples of the alcohol compound include methanol, ethanol, propanol, isopropyl alcohol, diethylaminoethanol, isobutanol, 4-(2-hydroxyethyl) morpholine, 3-morpholinopropanol, and diethylaminopropanol.

The transition metal which may be used in this step is, for example, a palladium catalyst (e.g., palladium acetate, tris (dibenzylideneacetone)dipalladium, bis(triphenylphosphine)palladium(II) dichloride, a 1,1'-bis(diphenylphosphino) ferrocene-palladium(II) dichloride-dichloromethane complex). If necessary, a ligand (e.g., triphenylphosphine, xantphos, tri-tert-butylphosphine) is added.

The amount of the transition metal used differs by the type of the catalyst and is usually from 0.0001 to 1 mol, preferably from 0.001 to 0.5 mol, with respect to 1 mol of the compound of formula (IV). The amount of the ligand used is usually from 0.0001 to 4 mol, preferably from 0.01 to 2 mol, with respect to 1 mol of the compound of formula (IV).

For the reaction, if necessary, a base can be added. Examples of the base include: organic bases such as triethylamine, diisopropylethylamine, pyridine, lutidine, collidine, 4-dimethylaminopyridine, N-methylmorpholine, potassium tert-butyrate, sodium tert-butyrate, sodium methoxide, sodium ethoxide, lithium hexamethyldisilazide, sodium hexamethyldisilazide, potassium hexamethyldisilazide, and butyllithium; and inorganic bases such as sodium bicarbonate, sodium carbonate, potassium carbonate, cesium carbonate, sodium hydroxide, and sodium hydride.

The amount of the base used is usually from 0.1 to 50 mol, preferably from 1 to 20 mol, with respect to 1 mol of the compound of formula (IV).

The reaction solvent is not particularly limited as long as the solvent does not interfere with the reaction. Examples thereof include hydrocarbons (e.g., benzene, toluene, xylene), nitriles (e.g., acetonitrile), ethers (e.g., dimethoxyethane, tetrahydrofuran, 1,4-dioxane), alcohols (e.g., methanol, ethanol), aprotic polar solvents (e.g., dimethylformamide, dimethylacetamide, N-methylpyrrolidinone, dimethyl sulfoxide, hexamethylphosphoramide), water, and mixtures thereof.

The reaction time is preferably from 0.1 to 100 hours, more preferably from 0.5 to 24 hours.

The reaction temperature is from 0° C. to the boiling temperature of the solvent, preferably from 0 to 150° C.

After this reaction, an ester mixture corresponding to the carboxylic acid compound (V) and the alcohol used is formed. Therefore, this ester mixture is converted to a compound of formula (V) through hydrolysis reaction.

The hydrolysis reaction is carried out using a base. Examples of the base include: organic bases such as diethylamine, diisopropylamine, potassium tert-butyrate, sodium tert-butyrate, sodium methoxide, sodium ethoxide, lithium hexamethyldisilazide, sodium hexamethyldisilazide, potassium hexamethyldisilazide, and butyllithium; and inorganic bases such as sodium bicarbonate, sodium carbonate, potassium carbonate, cesium carbonate, and sodium hydroxide.

The reaction solvent is not particularly limited as long as the solvent does not interfere with the hydrolysis reaction. Examples thereof include hydrocarbons (e.g., benzene, toluene, xylene), nitriles (e.g., acetonitrile), ethers (e.g., dimethoxyethane, tetrahydrofuran, 1,4-dioxane), alcohols (e.g., methanol and ethanol), aprotic polar solvents (e.g., dimethylformamide, dimethylacetamide, N-methylpyrrolidinone, dimethyl sulfoxide, hexamethylphosphoramide), water, and mixtures thereof.

The hydrolysis reaction time is preferably from 0.1 to 100 hours, more preferably from 0.5 to 24 hours.

The hydrolysis reaction temperature is from 0° C. to the boiling temperature of the solvent, preferably from 0 to 150° C.

Thus-obtained compound of formula (V) can be isolated and purified by a separation and purification approach known in the art mentioned later or can be subjected to a subsequent step without being isolated and purified.

(3rd Step)

This step is a step of producing a compound of formula (VI) by deprotecting the protected amino group in the compound of formula (V).

The deprotection method can be carried out by an ordinary method known in the art, for example, a method described in Protective Groups in Organic Synthesis, T. W. Greene, John Wiley & Sons, Inc. (1981) or a method equivalent thereto. Examples of the protective group include tert-butyloxycarbonyl.

When a tert-butyloxycarbonyl group is used as the protective group, the deprotection is preferably performed under acidic conditions. Examples of the acid include hydrochloric acid, acetic acid, trifluoroacetic acid, sulfuric acid, methanesulfonic acid, and tosylic acid. Alternatively, deprotection using Lewis acid is also preferred. Examples thereof include trimethylsilyl iodide and a boron trifluoride-diethyl ether complex.

The amount of the acid used is preferably from 1 to 100 mol, with respect to 1 mol of the compound of formula (V).

The reaction solvent is not particularly limited as long as the solvent does not interfere with the reaction. Examples of the solvent used include alcohols (e.g., methanol), hydrocarbons (e.g., benzene, toluene, xylene), halogenated hydrocarbons (e.g., methylene chloride, chloroform, 1,2-dichloroethane), nitriles (e.g., acetonitrile), ethers (e.g., dimethoxyethane, tetrahydrofuran), aprotic polar solvents (e.g., N,N-dimethylformamide, dimethyl sulfoxide, hexamethylphosphoramide), and mixtures thereof.

The reaction time is preferably from 0.1 to 100 hours, more preferably from 0.5 to 24 hours.

The reaction temperature is from 0 to 120° C., preferably from 0 to 90° C.

Thus-obtained compound of formula (VI) can be isolated and purified by a separation and purification approach known in the art mentioned later or can be subjected to a subsequent step without being isolated and purified.

(4th Step)

This step is a step of producing a compound of formula (VII) through the condensing reaction of the compound of formula (VI) with a carboxylic acid represented by Y—COOH or an acid halide represented by Y—C(=O)-L (L represents a chlorine atom or a bromine atom).

When the carboxylic acid represented by Y—COOH is used as a reagent, the reaction is carried out using from 0.5 to 10 mol, preferably from 1 to 3 mol, of the carboxylic acid with respect to 1 mol of the compound of formula (VI) in the presence of an appropriate condensing agent.

This carboxylic acid is a commercially available product or can be produced according to a method known in the art.

The reaction solvent is not particularly limited as long as the solvent does not interfere with the reaction. Preferred examples thereof include: alcohols such as isopropanol and tert-butyl alcohol; hydrocarbons such as toluene and benzene; halogenated hydrocarbons such as methylene chloride and chloroform; ethers such as tetrahydrofuran and 1,4-dioxane; aprotic polar solvents such as dimethylformamide, dimethylacetamide, N-methylpyrrolidinone, and dimethyl sulfoxide; and mixed solvents thereof.

The reaction temperature is usually from −78 to 200° C., preferably from 0 to 50° C.

The reaction time is usually from 5 minutes to 3 days, preferably from 5 minutes to 10 hours.

Examples of the condensing agent include diphenylphosphoryl azide, N,N'-dicyclohexylcarbodiimide, benzotriazol-1-yloxy-trisdimethylaminophosphonium salt, 4-(4,6-dimethoxy-1,3,5-triazin-2-yl)-4-methylmorpholinium chloride, 1-ethyl-3-(3-dimethylaminopropyl)carbodiimide, a combination of 1-ethyl-3-(3-dimethylaminopropyl)carbodiimide and 1-hydroxybenzotriazole, 2-chloro-1,3-dimethylimidazolinium chloride, and O-(7-azabenzotriazol-1-yl)-N,N,N',N'-tetramethylhexauronium hexafluorophosphate.

For the reaction, if necessary, a base can be added. Examples of the base include: organic bases such as triethylamine, diisopropylethylamine, pyridine, lutidine, collidine, 4-dimethylaminopyridine, potassium tert-butyrate, sodium tert-butyrate, sodium methoxide, sodium ethoxide, lithium hexamethyldisilazide, sodium hexamethyldisilazide, potassium hexamethyldisilazide, and butyllithium; and inorganic bases such as sodium bicarbonate, sodium carbonate, potassium carbonate, cesium carbonate, sodium hydroxide, and sodium hydride.

The amount of the base used is preferably from 1 to 100 mol, more preferably from 1 to 10 mol, with respect to 1 mol of the compound of formula (VI).

When the acid halide represented by Y—C(=O)-L (L represents a chlorine atom or a bromine atom) is used as a reagent, the reaction is carried out using from 0.5 to 5 mol, preferably from 0.9 to 1.1 mol, of the acid halide with respect to 1 mol of the compound of formula (VI).

This acid halide is a commercially available product or can be produced according to a method known in the art.

The reaction solvent is not particularly limited as long as the solvent does not interfere with the reaction. Preferred examples thereof include: water; hydrocarbons such as toluene and benzene; halogenated hydrocarbons such as methylene chloride and chloroform; ethers such as tetrahydrofuran and 1,4-dioxane; nitriles such as acetonitrile; aprotic polar solvents such as dimethylformamide, dimethylacetamide, and N-methylpyrrolidinone; and mixed solvents thereof.

The reaction temperature is usually from −78 to 200° C., preferably from −20 to 50° C.

The reaction time is usually from 5 minutes to 3 days, preferably from 5 minutes to 10 hours.

For the reaction, if necessary, a base can be added. Examples of the base include: organic bases such as triethylamine, diisopropylethylamine, pyridine, lutidine, collidine, 4-dimethylaminopyridine, potassium tert-butyrate, sodium tert-butyrate, sodium methoxide, sodium ethoxide, lithium hexamethyldisilazide, sodium hexamethyldisilazide, potassium hexamethyldisilazide, and butyllithium; and inorganic bases such as sodium bicarbonate, sodium carbonate, potassium carbonate, cesium carbonate, sodium hydroxide, and sodium hydride.

The amount of the base used is preferably from 1 to 100 mol, more preferably from 1 to 10 mol, with respect to 1 mol of the compound of formula (VI).

Thus-obtained compound of formula (VII) can be isolated and purified by a separation and purification approach known in the art mentioned later.

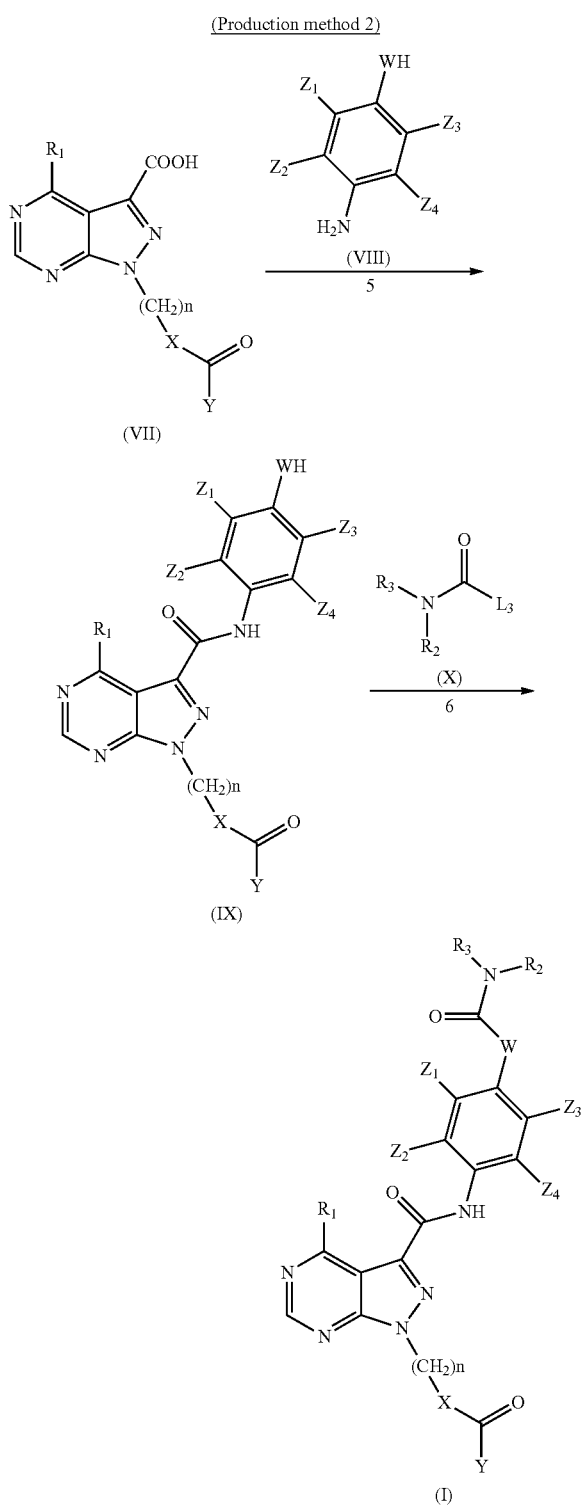

(Production method 2)

wherein $L_3$ represents a leaving group; and X, Y, $Z_1$, $Z_2$, $Z_3$, $Z_4$, W, n, $R_1$, $R_2$, and $R_3$ are as defined above.

(5th Step)

This step is a step of producing a compound of formula (IX) through the condensing reaction of a compound of formula (VII) with a compound of formula (VIII).

The reaction is carried out using from 0.5 to 10 mol, preferably from 1 to 3 mol, of the compound of formula (VIII) with respect to 1 mol of the compound of formula (VII) in the presence of an appropriate condensing agent as a reagent. This aniline compound is a commercially available product or can be produced according to a method known in the art.

The reaction solvent is not particularly limited as long as the solvent does not interfere with the reaction. Preferred examples thereof include isopropanol, tert-butyl alcohol, toluene, benzene, methylene chloride, chloroform, tetrahydrofuran, 1,4-dioxane, dimethylformamide, dimethylacetamide, N-methylpyrrolidinone, dimethyl sulfoxide, and mixed solvents thereof.

The reaction temperature is usually from −78 to 200° C., preferably from 0 to 50° C.

The reaction time is usually from 5 minutes to 3 days, preferably from 5 minutes to 10 hours.

Examples of the condensing agent include diphenylphosphoryl azide, N,N'-dicyclohexylcarbodiimide, benzotriazol-1-yloxy-trisdimethylaminophosphonium salt, 4-(4,6-dimethoxy-1,3,5-triazin-2-yl)-4-methylmorpholinium chloride, 1-ethyl-3-(3-dimethylaminopropyl)carbodiimide, a combination of 1-ethyl-3-(3-dimethylaminopropyl)carbodiimide and 1-hydroxybenzotriazole, 2-chloro-1,3-dimethylimidazolinium chloride, and O-(7-azabenzotriazol-1-yl)-N,N,N',N'-tetramethylhexauronium hexafluorophosphate.

For the reaction, if necessary, a base can be added. Examples of the base include: organic bases such as triethylamine, diisopropylethylamine, pyridine, lutidine, collidine, 4-dimethylaminopyridine, potassium tert-butyrate, sodium tert-butyrate, sodium methoxide, sodium ethoxide, lithium hexamethyldisilazide, sodium hexamethyldisilazide, potassium hexamethyldisilazide, and butyllithium; and inorganic bases such as sodium bicarbonate, sodium carbonate, potassium carbonate, cesium carbonate, sodium hydroxide, and sodium hydride.

The amount of the base used is from 1 to 100 mol, preferably from 1 to 10 mol, with respect to 1 mol of the compound of formula (VII).

Thus-obtained compound of formula (IX) can be isolated and purified by a separation and purification approach known in the art mentioned later or can be subjected to a subsequent step without being isolated and purified.

(6th Step)

This step is a step of producing the compound of the present invention of formula (I) from the compound of formula (IX) and a compound of formula (X).

In the formula (X), the leaving group represented by $L_3$ is preferably chlorine, bromine, iodine, methanesulfonic acid ester, or p-toluenesulfonic acid ester. The compound of formula (X) is a commercially available product or can be produced according to a method known in the art.

The compound of formula (X) can be used at from 1 to 10 mol, preferably from 1 to 5 mol, with respect to 1 mol of the compound of formula (IX).

For the reaction, if necessary, a base can be added. Examples of the base include: inorganic bases such as sodium bicarbonate, sodium carbonate, potassium carbonate, cesium carbonate, cesium hydroxide, sodium hydride, and potassium hydride; and organic amines such as trimethylamine, triethylamine, tripropylamine, diisopropylethylamine, N-methylmorpholine, pyridine, 4-(N,N-dimethylamino)pyridine, lutidine, and collidine.

The amount of the base used can be from 1 to 100 mol, preferably from 2 to 10 mol, with respect to 1 mol of the compound of formula (IX).

Examples of the solvent which can be used include N,N-dimethylformamide, N,N-dimethylacetamide, dimethyl sulfoxide, tetrahydrofuran, 1,4-dioxane, N-methylpyrrolidin-2-one, acetonitrile, and mixed solvents thereof.

The reaction time is preferably from 0.1 to 100 hours, more preferably from 0.5 to 24 hours.

The reaction temperature is from 0° C. to the boiling temperature of the solvent, preferably from 0 to 100° C.

Thus-obtained compound of formula (I) can be isolated and purified by a separation and purification approach known in the art mentioned later.

Also, the compound (I) of the present invention can be produced by, for example, the following production method:

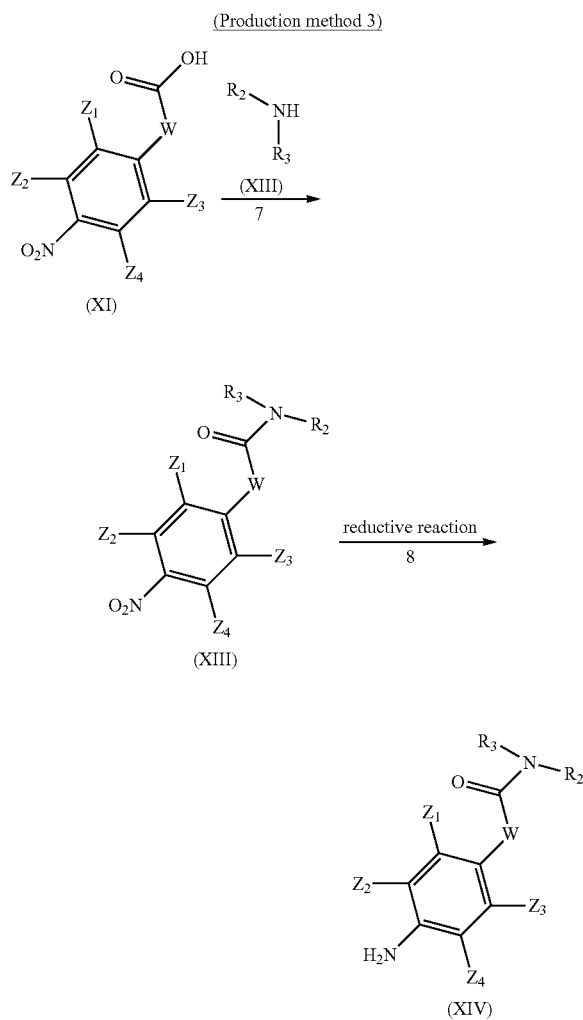

wherein $Z_1$, $Z_2$, $Z_3$, $Z_4$, W, $R_2$, and $R_3$ are as defined above.

(7th Step)

This step is a step of producing a compound of formula (XIII) through the condensing reaction of a compound of formula (XI) with a compound of formula (XII).

The reaction is carried out using from 0.5 to 10 mol, preferably from 1 to 3 mol, of the compound of formula (XII) with respect to 1 mol of the compound of formula (XI) in the presence of an appropriate condensing agent as a reagent. This amine (XII) is a commercially available product or can be produced according to a method known in the art.

The reaction solvent is not particularly limited as long as the solvent does not interfere with the reaction. Preferred examples thereof include isopropanol, tert-butyl alcohol, toluene, benzene, methylene chloride, chloroform, tetrahydrofuran, 1,4-dioxane, dimethylformamide, dimethylacetamide, N-methylpyrrolidinone, dimethyl sulfoxide, and mixed solvents thereof.

The reaction temperature is usually from −78 to 200° C., preferably from 0 to 50° C.

The reaction time is usually from 5 minutes to 3 days, preferably from 5 minutes to 10 hours.

Examples of the condensing agent include diphenylphosphoryl azide, N,N'-dicyclohexylcarbodiimide, benzotriazol-1-yloxy-trisdimethylaminophosphonium salt, 4-(4,6-dimethoxy-1,3,5-triazin-2-yl)-4-methylmorpholinium chloride, 1-ethyl-3-(3-dimethylaminopropyl)carbodiimide, a combination of 1-ethyl-3-(3-dimethylaminopropyl)carbodiimide and 1-hydroxybenzotriazole, 2-chloro-1,3-dimethylimidazolinium chloride, and O-(7-azabenzotriazol-1-yl)-N,N,N',N'-tetramethylhexauronium hexafluorophosphate.

For the reaction, if necessary, a base can be added. Examples of the base include: organic bases such as triethylamine, diisopropylethylamine, pyridine, lutidine, collidine, 4-dimethylaminopyridine, potassium tert-butyrate, sodium tert-butyrate, sodium methoxide, sodium ethoxide, lithium hexamethyldisilazide, sodium hexamethyldisilazide, potassium hexamethyldisilazide, and butyllithium; and inorganic bases such as sodium bicarbonate, sodium carbonate, potassium carbonate, cesium carbonate, sodium hydroxide, and sodium hydride.

The amount of the base used is from 1 to 100 mol, preferably from 1 to 10 mol, with respect to 1 mol of the compound of formula (XI).

Thus-obtained compound of formula (XIII) can be isolated and purified by a separation and purification approach known in the art mentioned later or can be subjected to a subsequent step without being isolated and purified.

(8th Step)

This step is a step of producing a compound of formula (XIV) through the reduction reaction of the compound of formula (XIII) using a metal catalyst.

The metal catalyst for use in this step is an iron reagent, a palladium reagent, a nickel reagent, or the like. Hydrogen gas, formic acid, or the like can be used as a reducing agent.

The reaction solvent is not particularly limited as long as the solvent does not interfere with the reaction. Examples thereof include alcohols (e.g., methanol, ethanol), ethers (e.g., tetrahydrofuran, 1,4-dioxane), aprotic polar solvents (e.g., dimethylformamide, dimethylacetamide, N-methylpyrrolidinone, dimethyl sulfoxidt, hexamethylphosphoramide), water, and mixtures thereof.

The reaction time is preferably from 0.1 to 100 hours, more preferably from 0.5 to 24 hours.

The reaction temperature is from 0° C. to the boiling temperature of the solvent, preferably from 0 to 150° C.

Thus-obtained compound of formula (XIV) can be isolated and purified by a separation and purification approach known in the art mentioned later.

(Production method 4)

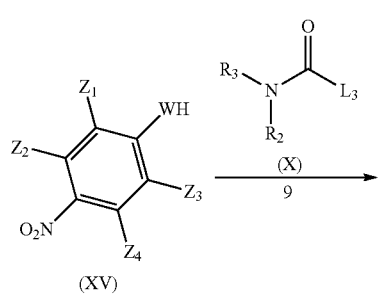

(XV)

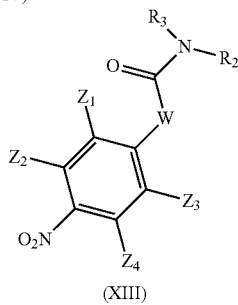

(XIII)

reductive reaction
10

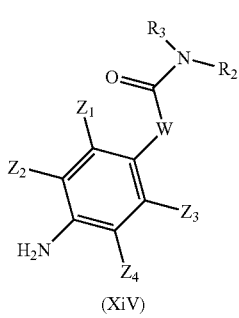

(XiV)

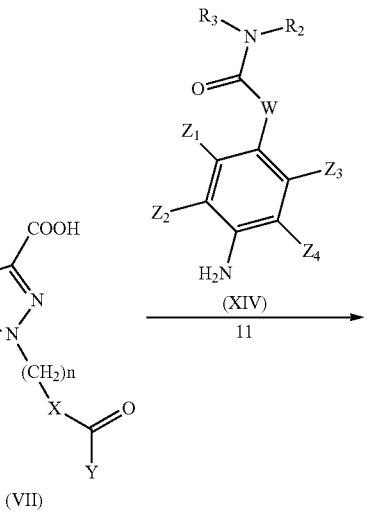

(VII)

dimethyl sulfoxide, tetrahydrofuran, 1,4-dioxane, N-methylpyrrolidin-2-one, acetonitrile, and mixed solvents thereof.

The reaction time is preferably from 0.1 to 100 hours, more preferably from 0.5 to 24 hours.

The reaction temperature is from 0° C. to the boiling temperature of the solvent, preferably from 0 to 100° C.

Thus-obtained compound of formula (XIII) can be isolated and purified by a separation and purification approach known in the art mentioned later or can be subjected to a subsequent step without being isolated and purified.

(10th Step)

This step is a step of producing a compound of formula (XIV) through reduction reaction from the compound of formula (XIII). This compound can be produced by the same production method as in the 8th step described above.

(Production method 5)

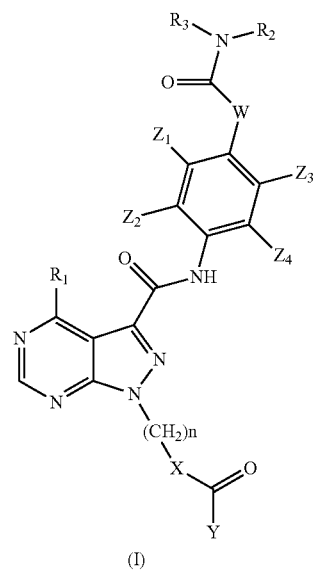

(I)

wherein $L_3$ represents a leaving group; and $Z_1$, $Z_2$, $Z_3$, $Z_4$, W, $R_2$, and $R_3$ are as defined above.

(9th Step)

This step is a step of producing a compound of formula (XIII) from a compound of formula (XV) and a compound of formula (X).

The compound of formula (X) can be used at from 1 to 10 mol, preferably from 1 to 5 mol, with respect to 1 mol of the compound of formula (XV).

Examples of the reagent for use in the reaction include dialkylcarbamoyl chloride, S-methyl dialkylcarbamoyl ester, and dichloromethylene dialkyliminium chloride. These reagents are commercially available products or can be produced according to a method known in the art.

The reagent can be used at from 1 to 100 mol, preferably from 2 to 10 mol, with respect to 1 mol of the compound of formula (XV).

For the reaction, if necessary, a base can be added. Examples of the base include: inorganic bases such as sodium bicarbonate, sodium carbonate, potassium carbonate, cesium carbonate, cesium hydroxide, sodium hydride, and potassium hydride; and organic amines such as trimethylamine, triethylamine, tripropylamine, diisopropylethylamine, N-methylmorpholine, pyridine, 4-(N,N-dimethylamino)pyridine, lutidine, and collidine.

The amount of the base used can be from 1 to 100 mol, preferably from 2 to 10 mol, with respect to 1 mol of the compound of formula (XV).

Examples of the reaction solvent which can be used include N,N-dimethylformamide, N,N-dimethylacetamide, wherein X, $Z_1$, $Z_2$, $Z_3$, $Z_4$, W, n, $R_1$, $R_2$, and $R_3$ are as defined above.

(11th Step)

This step is a step of producing the compound of the present invention of formula (I) through the condensing reaction of a compound of formula (VII) with a compound of formula (XIV).

The reaction is carried out using from 0.5 to 10 mol, preferably from 1 to 3 mol, of the compound of formula (XIV) with respect to 1 mol of the compound of formula (VII) in the presence of an appropriate condensing agent as a reagent.

The reaction solvent is not particularly limited as long as the solvent does not interfere with the reaction. Preferred examples thereof include isopropanol, tert-butyl alcohol, toluene, benzene, methylene chloride, chloroform, tetrahydrofuran, 1,4-dioxane, dimethylformamide, dimethylacetamide, N-methylpyrrolidinone, dimethyl sulfoxide, and mixed solvents thereof.

The reaction temperature is usually from −78 to 200° C., preferably from 0 to 50° C. The reaction time is usually from 5 minutes to 3 days, preferably from 5 minutes to 10 hours.

Examples of the condensing agent include diphenylphosphoryl azide, N,N'-dicyclohexylcarbodiimide, benzotriazol-1-yloxy-trisdimethylaminophosphonium salt, 4-(4,6-dimethoxy-1,3,5-triazin-2-yl)-4-methylmorpholinium chloride, 1-ethyl-3-(3-dimethylaminopropyl)carbodiimide, a combination of 1-ethyl-3-(3-dimethylaminopropyl)carbodiimide and 1-hydroxybenzotriazole, 2-chloro-1,3-dimethylimidazolinium chloride, and O-(7-azabenzotriazol-1-yl)-N,N,N',N'-tetramethyluronium hexafluorophosphate.

For the reaction, if necessary, a base can be added. Examples of the base include: organic bases such as triethylamine, diisopropylethylamine, pyridine, lutidine, collidine, 4-dimethylaminopyridine, potassium tert-butyrate, sodium tert-butyrate, sodium methoxide, sodium ethoxide, lithium hexamethyldisilazide, sodium hexamethyldisilazide, potassium hexamethyldisilazide, and butyllithium; and inorganic bases such as sodium bicarbonate, sodium carbonate, potassium carbonate, cesium carbonate, sodium hydroxide, and sodium hydride.

The amount of the base used is from 1 to 100 mol, preferably from 1 to 10 mol, with respect to 1 mol of the compound of formula (VII).

Thus-obtained compound of the present invention of formula (I) can be isolated and purified by a separation and purification approach known in the art mentioned later.

In Production methods 1 to 5 described above, when it comes to an amino group, an imino group, a hydroxy group, a carboxyl group, a carbonyl group and an amide group, and a functional group having an active proton such as indole, a reagent protected in an appropriate step in each production method may be used, or a protective group thereof may be introduced to the functional group by a conventional method and then the protective group may be removed.

The "protective group for the amino group or the imino group" is not particularly limited as long as the protective group has the function. Examples thereof include: aralkyl groups such as a benzyl group, a p-methoxybenzyl group, a 3,4-dimethoxybenzyl group, a o-nitrobenzyl group, a p-nitrobenzyl group, a benzhydryl group, a trityl group, and a cumyl group; lower alkanoyl groups such as a formyl group, an acetyl group, a propionyl group, a butyryl group, a pivaloyl group, a trifluoroacetyl group, and a trichloroacetyl group; a benzoyl group; arylalkanoyl groups such as a phenylacetyl group and a phenoxyacetyl group; lower alkoxycarbonyl groups such as a methoxycarbonyl group, an ethoxycarbonyl group, a propyloxycarbonyl group, and a tert-butoxycarbonyl group; aralkyloxycarbonyl groups such as a p-nitrobenzyloxycarbonyl group and a phenethyloxycarbonyl group; lower alkylsilyl groups such as a trimethylsilyl group and a tert-butyldimethylsilyl group; a tetrahydropyranyl group; a trimethylsilylethoxymethyl group; lower alkylsulfonyl groups such as a methylsulfonyl group, an ethylsulfonyl group, and a tert-butylsulfonyl group; lower alkylsulfinyl groups such as a tert-butylsulfinyl group; arylsulfonyl groups such as a benzenesulfonyl group and a toluenesulfonyl group; and imide groups such as a phthalimide group. Particularly, a trifluoroacetyl group, an acetyl group, a tert-butoxycarbonyl group, a benzyloxycarbonyl group, a trimethylsilylethoxymethyl group, or a cumyl group is preferred.

The "protective group for the hydroxy group" is not particularly limited as long as the protective group has the function. Examples thereof include: lower alkyl groups such as a methyl group, an ethyl group, a propyl group, an isopropyl group, and a tert-butyl group; lower alkylsilyl groups such as a trimethylsilyl group and a tert-butyldimethylsilyl group; lower alkoxymethyl groups such as a methoxymethyl group and a 2-methoxyethoxymethyl group; a tetrahydropyranyl group; a trimethylsilylethoxymethyl group; aralkyl groups such as a benzyl group, a p-methoxybenzyl group, a 2,3-dimethoxybenzyl group, a o-nitrobenzyl group, a p-nitrobenzyl group, and a trityl group; and acyl groups such as a formyl group, an acetyl group, and a trifluoroacetyl group. Particularly, a methyl group, a methoxymethyl group, a tetrahydropyranyl group, a trimethylsilylethoxymethyl group, a tert-butyldimethylsilyl group, or an acetyl group is preferred.

The "protective group for the carboxyl group" is not particularly limited as long as the protective group has the function. Examples thereof include: lower alkyl groups such as a methyl group, an ethyl group, a propyl group, an isopropyl group, and a tert-butyl group; halo-lower alkyl groups such as a 2,2,2-trichloroethyl group; lower alkenyl groups such as an allyl group; a trimethylsilylethoxymethyl group; and aralkyl groups such as a benzyl group, a p-methoxybenzyl group, a p-nitrobenzyl group, a benzhydryl group, and a trityl group. Particularly, a methyl group, an ethyl group, a tert-butyl group, an allyl group, a benzyl group, a p-methoxybenzyl group, or a trimethylsilylethoxymethyl group is preferred.

The "protective group for the carbonyl group" is not particularly limited as long as the protective group has the function. Examples thereof include ketals and acetals such as ethylene ketal, trimethylene ketal, dimethyl ketal, ethylene acetal, trimethylene acetal, and dimethyl acetal.

The "protective group for the amide group or the functional group having active proton such as indole" is not particularly limited as long as the protective group has the function. Examples thereof include: lower alkyl groups such as a methyl group, an ethyl group, a propyl group, an isopropyl group, and a tert-butyl group; lower alkylsilyl groups such as a trimethylsilyl group and a tert-butyldimethylsilyl group; lower alkoxymethyl groups such as a methoxymethyl group and a 2-methoxyethoxymethyl group; a tetrahydropyranyl group; a trimethylsilylethoxymethyl group; aralkyl groups such as a benzyl group, a p-methoxybenzyl group, a 2,3-dimethoxybenzyl group, a o-nitrobenzyl group, a p-nitrobenzyl group, and a trityl group; and acyl groups such as a formyl group, an acetyl group, and a trifluoroacetyl group. Particularly, a methyl group, a methoxymethyl group, a tetrahydropyranyl group, a trimethylsilylethoxymethyl group, a tert-butyldimethylsilyl group, or an acetyl group is preferred.

The method for removing the protective group differs by the type of the protective group, the stability of the compound of interest, etc., and is carried out according to, for example, a method described in the literature (see Protective Groups in Organic Synthesis, 3rd edition, T. W. Greene, John Wiley & Sons, Inc., 1999) or a method equivalent thereto, for example, solvolysis using an acid or a base, i.e., a method of allowing, for example, 0.01 mol to a large excess of an acid, preferably trifluoroacetic acid, formic acid, or hydrochloric acid, or an equimolar amount to a large excess of a base, preferably potassium hydroxide or calcium hydroxide, to act thereon; chemical reduction using a metal halide complex or the like; or catalytic reduction using a palladium-carbon catalyst, a Raney nickel catalyst, or the like.

The compound of formula (I) of the present invention and the intermediates thereof can each be isolated and purified easily by a separation and purification approach known in the art. Examples of such an approach can include concentration, concentration under reduced pressure, solvent extraction, recrystallization, reprecipitation, preparative reverse-phase high-performance liquid chromatography, column chromatography, and preparative thin-layer chromatography.

When the compound of the present invention has optical isomers, stereoisomers, tautomers, or rotational isomers, any of these isomers and mixtures thereof are also included in the compound of the present invention. A racemate of the compound of the present invention or optically active forms resolved from the racemate are also included in the compound of the present invention. These isomers can each be obtained as a single compound by a synthesis approach and a separation approach (concentration, solvent extraction, column chromatography, recrystallization, etc.) known per se in the art.

The compound of the present invention also includes tautomers.

The compound of the present invention or a salt thereof may be crystalline. A single crystal form or a polymorphic mixture is also included in the compound of the present invention or the salt thereof. The crystals can be produced by crystallization using a crystallization method known per se in the art. The compound of the present invention or the salt thereof may be a solvate (e.g., a hydrate) or may be a non-solvate. Both of them are also included in the compound of the present invention or the salt thereof. A compound labeled with an isotope (e.g., $^{3}H$, $^{14}C$, $^{35}S$, $^{125}I$) or the like is also included in the compound of the present invention or the salt thereof.

A prodrug of the compound of the present invention or the salt thereof is also encompassed by the present invention. The prodrug refers to a compound which is converted to the compound of the present invention or the salt thereof through reaction with an enzyme, gastric juice, or the like under physiological conditions in vivo, i.e., a compound which is converted to the compound of the present invention or the salt thereof through enzymatic oxidation, reduction, hydrolysis, etc., or a compound which is converted to the compound of the present invention or the salt thereof through hydrolysis, etc., with gastric juice or the like. Alternatively, the prodrug of the compound of the present invention or the salt thereof may be converted to the compound of the present invention or the salt thereof under physiological conditions as described in Hirokawa-Shoten Ltd. (1990) "Iyakuhin no Kaihatsu (Development of drugs in English)", Vol. 7, Molecular Design, p. 163-198.

The salt of the compound of the present invention is not particularly limited as long as the salt is pharmaceutically acceptable. The salt of the compound of the present invention means a salt routinely used in the organic chemical field. Examples thereof can include salts including: when the compound has a carboxyl group, a base-addition salt of the carboxyl group; and when the compound has an amino group or a basic heterocyclic group, an acid-addition salt of the amino group or the basic heterocyclic group.

Examples of the base-addition salt include: alkali metal salts such as sodium salt and potassium salt; alkaline earth metal salts such as calcium salt and magnesium salt; ammonium salts; and organic amine salts such as trimethylamine salt, triethylamine salt, dicyclohexylamine salt, ethanolamine salt, diethanolamine salt, triethanolamine salt, procaine salt, and N,N'-dibenzylethylenediamine salt.

Examples of the acid-addition salt include: inorganic acid salts such as hydrochloride, sulfate, nitrate, phosphate, and perchlorate; organic acid salts such as acetate, formate, maleate, fumarate, tartrate, citrate, ascorbate, and trifluoroacetate; and sulfonates such as methanesulfonate, isethionate, benzenesulfonate, and p-toluenesulfonate.

The compound of the present invention or the salt thereof has excellent HER2 inhibitory activity. The compound of the present invention or the salt thereof also has excellent selectivity for HER2. Thus, the compound of the present invention or the salt thereof is useful as an antitumor agent and also has the advantage that there are fewer adverse effects ascribable to the inhibition of other kinases.

In the present specification, the term "HER2" includes human or nonhuman mammalian HER2 and is preferably human HER2. The term "HER2" also includes isoforms.

The compound of the present invention or the salt thereof is useful as a medicament for the prevention or treatment of a disease involving HER2, because of its excellent HER2 inhibitory activity.

Examples of the "disease involving HER2" include diseases in which the functional deletion, suppression, and/or inhibition of HER2 leads to reduction in incidence, remission of symptoms, alleviation, and/or complete cure. Examples of such a disease include, but are not limited to, malignant tumor. The disease is preferably malignant tumor having HER2 overexpression, HER2 gene amplification, or HER2 mutation. Examples of the targeted "malignant tumor" include, but are not particularly limited to, head and neck cancer, esophageal cancer, stomach cancer, colon cancer, rectal cancer, liver cancer, gallbladder or bile duct cancer, biliary cancer, pancreatic cancer, lung cancer, breast cancer, ovary cancer, uterine cervical cancer, uterine body cancer, kidney cancer, bladder cancer, prostate cancer, testis tumor, bone or soft tissue sarcoma, blood cancer, multiple myeloma, skin cancer, brain tumor, and mesothelioma. The malignant tumor is preferably breast cancer, stomach cancer, esophageal cancer, ovary cancer, lung cancer, esophageal cancer, gallbladder or bile duct cancer, biliary cancer, bladder cancer, or colon cancer, more preferably breast cancer, stomach cancer, esophageal cancer, biliary cancer, ovary cancer, lung cancer, or esophageal cancer, even more preferably breast cancer or stomach cancer.

For use of the compound of the present invention or the salt thereof as a medicament, various dosage forms, if necessary, containing pharmaceutical carriers can be adopted according to the prophylactic or therapeutic purposes. The form may be, for example, any of oral agents, injections, suppositories, ointments, and patches. These dosage forms can each be produced by a routine formulation method known to those skilled in the art.

Various organic or inorganic carrier substances routinely used as pharmaceutical materials are used as the pharmaceutical carriers. A solid preparation is supplemented with an excipient, a binder, a disintegrant, a lubricant, a coating agent, or the like, and a liquid preparation is supplemented with a solvent, a solubilizer, a suspending agent, a tonicity agent, a pH adjuster or a buffer, a soothing agent, or the like.

If necessary, pharmaceutical additives such as an antiseptic, an antioxidant, a colorant, a corrigent, and a stabilizer can also be used.

Examples of the excipient include lactose, saccharose, D-mannitol, starch, crystalline cellulose, and calcium silicate.

Examples of the binder include hydroxypropylcellulose, methylcellulose, polyvinylpyrrolidone, maltose syrup powder, and hypromellose.

Examples of the disintegrant include sodium starch glycolate, carmellose calcium, croscarmellose sodium, crospovidone, low-substituted hydroxypropylcellulose, and partially pregelatinized starch.

Examples of the lubricant include talc, magnesium stearate, sucrose fatty acid ester, stearic acid, and sodium stearyl fumarate.

Examples of the coating agent include ethylcellulose, aminoalkyl methacrylate copolymer RS, hypromellose, and saccharose.

Examples of the solvent include water, propylene glycol, and saline.

Examples of the solubilizer include polyethylene glycol, ethanol, α-cyclodextrin, macrogol 400, and polysorbate 80.

Examples of the suspending agent include carrageenan, crystalline cellulose-carmellose sodium, and polyoxyethylene hydrogenated castor oil.

Examples of the tonicity agent include sodium chloride, glycerin, and potassium chloride.

Examples of the pH adjuster or the buffer include sodium citrate, hydrochloric acid, lactic acid, phosphoric acid, and sodium dihydrogen phosphate.

Examples of the soothing agent include procaine hydrochloride and lidocaine.

Examples of the antiseptic include ethyl p-hydroxybenzoate, cresol, and benzalkonium chloride.

Examples of the antioxidant include sodium sulfite, ascorbic acid, and natural vitamin E.

Examples of the colorant include titanium oxide, iron sesquioxide, Food Blue No. 1, and copper chlorophyll.

Examples of the corrigent include aspartame, saccharin, sucralose, 1-menthol, and mint flavor.

Examples of the stabilizer include sodium pyrosulfite, sodium edetate, erythorbic acid, magnesium oxide, and dibutylhydroxytoluene.

An oral solid preparation can be prepared by adding an excipient, a binder, a disintegrant, a lubricant, a colorant, a corrigent, or the like to the compound of the present invention and then producing tablets, coated tablets, granules, powders, capsules, or the like by a routine method.

An injection can be prepared by adding a pH adjuster, a buffer, a stabilizer, a tonicity agent, a local anesthetic, or the like to the compound of the present invention and producing subcutaneous, intramuscular, and intravenous injections by a routine method.

The amount of the compound of the present invention to be contained in each dosage unit form described above varies by the symptoms of a patient to receive this or by the dosage form, etc., and is generally desirably from 0.05 to 1000 mg for oral agents, from 0.01 to 500 mg for injections, or from 1 to 1000 mg for suppositories, per dosage unit form.

The daily dose of the drug having the dosage form differs by the symptoms, body weight, age, sex, etc., of the patient and cannot be generalized. The daily dose can be usually from 0.05 to 5000 mg, preferably from 0.1 to 1000 mg, of the compound of the present invention in an adult (body weight: 50 kg), and this dose is preferably administered once a day or in approximately two or three divided portions per day.

EXAMPLES

Hereinafter, the present invention will be described further specifically with reference to Examples. However, the present invention is not intended to be limited to these Examples by any means.

Various types of reagents were used in Examples which were commercially available unless otherwise specified. Purif-Pack® SI manufactured by Moritex Corp., KP-Sil® Silica Prepacked Column manufactured by Biotage Japan Ltd., or HP-Sil® Silica Prepacked Column manufactured by Biotage Japan Ltd. was used in silica gel column chromatography.

Purif-Pack® NH manufactured by Moritex Corp. or KP-NH® Prepacked Column manufactured by Biotage Japan Ltd. was used in basic silica gel column chromatography.

Kieselgel™ 60F254, Art. 5744 manufactured by Merck KGaA or NH2 Silica Gel 60F254 Plate manufactured by Wako Pure Chemical Industries, Ltd. was used in preparative thin-layer chromatography.

NMR spectra were measured using AL400 (400 MHz; JEOL Ltd.), Mercury 400 (400 MHz; Agilent Technologies, Inc.) spectrometer, or Inova 400 (400 MHz; Agilent Technologies, Inc.) spectrometer equipped with OMNMR probe (Protasis Corp.) and using tetramethylsilane as an internal standard in the case of containing tetramethylsilane in a deuterated solvent and a NMR solvent as an internal standard in other cases. Total δ values were indicated by ppm.

Microwave reaction was carried out using Discover S class manufactured by CEM Corp.

LCMS spectra were measured using ACQUITY SQD (quadrupole type) manufactured by Waters Corp. under the following conditions:

Column: YMC-Triart C18 manufactured by YMC Co., Ltd., 2.0×50 mm, 1.9 μm

MS detection: ESI positive

UV detection: 254 and 210 nm

Column flow rate: 0.5 mL/min

Mobile phase: water/acetonitrile (0.1% formic acid)

Injection volume: 1 μL

Gradient (table 1)

| Time (min) | Water | Acetonitrile |
|---|---|---|
| 0 | 95 | 5 |
| 0.1 | 95 | 5 |
| 2.1 | 5 | 95 |
| 3.0 | STOP | |

Reverse-phase preparative HPLC purification was carried out using a preparative system manufactured by Waters Corp. under the following conditions: Column: YMC-Actus Triart C18 manufactured by YMC Co., Ltd., 20×50 mm, 5 μm and YMC-Actus Triart C18 manufactured by YMC Co., Ltd., 20×10 mm, 5 μm connected for use UV detection: 254 nm MS detection: ESI positive Column flow rate: 25 mL/min Mobile phase: water/acetonitrile (0.1% formic acid)

Injection volume: 0.1 to 0.5 mL

The meanings of abbreviations are as follows:
s: singlet
d: doublet
t: triplet
q: quartet
dd: double doublet
dt: double triplet
td: triple doublet
tt: triple triplet
ddd: double double doublet
ddt: double double triplet
dtd: double triple doublet
tdd: triple double doublet
m: multiplet
br: broad
brs: broad singlet
DMSO-$d_6$: deuterated dimethyl sulfoxide
$CDCl_3$: deuterated chloroform
$CD_3OD$: deuterated methanol
THF: tetrahydrofuran
DMF: N,N-dimethylformamide
DMA: N,N-dimethylacetamide
NMP: 1-methyl-2-pyrrolidinone
DME: ethylene glycol dimethyl ether
DMSO: dimethyl sulfoxide
TFA: trifluoroacetic acid
WSC: 1-(3-dimethylaminopropyl)-3-ethylcarbodiimide hydrochloride
HATU: (dimethylamino)-N,N-dimethyl(3H-[1,2,3]triazolo[4,5-b]pyridin-3-yloxy)methaniminium hexafluorophosphate
DIPEA: diisopropylethylamine
Boc: tert-butoxycarbonyl group
dppf: 1,1'-bis(diphenylphosphino) ferrocene Reference Example 1 Synthesis of (R)-tert-butyl 3-(4-amino-3-iodo-1H-pyrazolo[3,4-d]pyrimidin-1-yl) piperidine-1-carboxylate

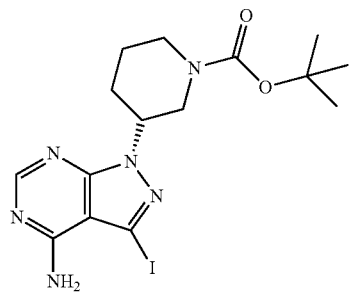

(Step 1) Synthesis of (S)-tert-butyl 3-(methylsulfonyloxy)piperidine-1-carboxylate (S)—N-Boc-3-piperidinol (20 g) was dissolved in toluene (100 mL). To the solution, triethylamine (21 mL) and methanesulfonyl chloride (9.2 mL) were added at 0° C. The mixture was stirred under ice cooling for 1 hour, and then, ethyl acetate and water were added thereto to separate an organic layer. The organic layer was washed with a saturated aqueous solution of sodium bicarbonate, a saturated aqueous solution of ammonium chloride, and water and then dried over anhydrous sodium sulfate, and the solvent was distilled off under reduced pressure to obtain 26.8 g of the title compound as a colorless solid.

(Step 2) Synthesis of (R)-tert-butyl 3-(4-amino-3-iodo-1H-pyrazolo[3,4-d]pyrimidin-1-yl) piperidine-1-carboxylate 3-Iodo-1H-pyrazolo[3,4-d]pyrimidin-4-amine (14.6 g) synthesized by the method described in the pamphlet of International Publication No. WO 2007/126841, (S)-tert-butyl 3-(methylsulfonyloxy) piperidine-1-carboxylate (25 g) obtained in (Step 1), and potassium carbonate (69 g) were suspended in DMA (150 mL), and the suspension was heated to 100° C. and stirred for 10 hours. After the mixture was cooled to room temperature, water (300 mL) was added thereto, and the precipitated solid was collected by filtration, washed with water, and then dried to obtain 26.9 g of the title compound as a yellow solid.

Physical property value: m/z $[M+H]^+$ 446.2

Reference Example 2 Synthesis of (R)-4-amino-1-(1-(tert-butyloxycarbonyl) piperidin-3-yl)-1H-pyrazolo[3,4-d]pyrimidine-3-carboxylic acid

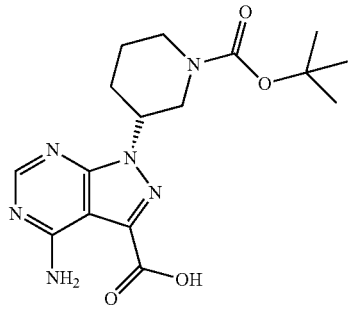

(R)-tert-Butyl 3-(4-amino-3-iodo-1H-pyrazolo[3,4-d]pyrimidin-1-yl)piperidine-1-carboxylate (2 g) obtained in Reference Example 1, 2-diethylaminoethanol (3 mL), and $Pd(PPh_3)_2Cl_2$ (158 mg) were dissolved in NMP (20 mL). After purging of the system with carbon monoxide, the solution was heated to 120° C. The solution was stirred for 1 hour and then cooled to room temperature. Methanol (10 mL) was added thereto, then a 5 N aqueous sodium hydroxide solution (6 mL) was added thereto, and the mixture was stirred for 10 minutes. After water was added, the aqueous layer was washed with ethyl acetate and adjusted to pH 4 with hydrochloric acid, and the precipitated solid was collected by filtration, washed with water, and then dried to obtain 1.26 g of the title compound as a pale yellow solid.

Physical property value: m/z $[M+H]^+$ 363.1

Reference Example 3 Synthesis of (R)-1-(1-acryloylpiperidin-3-yl)-4-amino-1H-pyrazolo[3,4-d]pyrimidine-3-carboxylic acid

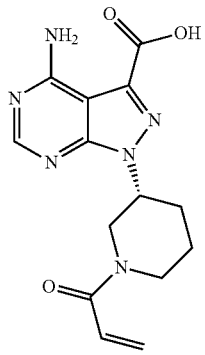 [SMILES: C=CC(=O)N1CCC[C@@H](n2nc(C(=O)O)c3c(N)ncnc32)C1]

To (R)-4-amino-1-(1-(tert-butyloxycarbonyl) piperidin-3-yl)-1H-pyrazolo[3,4-d]pyrimidine-3-carboxylic acid (10 g) obtained in Reference Example 2, 4 N hydrochloric acid/1,4-dioxane (50 mL) was added, and the mixture was stirred for 1 hour. Then, the solvent was removed with an evaporator. Chloroform (140 mL) and triethylamine (25 mL) were added to the residue, and the mixture was cooled in ice, followed by adding acryloyl chloride (2.23 mL). The mixture was stirred for 1.5 hours, and then, the solvent was removed with an evaporator. To the residue, formic acid was added until adjusting to pH 3.0, and the mixture was stirred for 2 hours. Then, the precipitated solid was collected by filtration and dried under reduced pressure to obtain 8.93 g of the title compound as a white-brown solid.

Physical property value: m/z [M+H]$^+$ 317.3

Reference Example 4 Synthesis of (R)-4-amino-1-(1-(tert-butyloxycarbonyl)pyrrolidin-3-yl)-1H-pyrazolo[3,4-d]pyrimidine-3-carboxylic acid

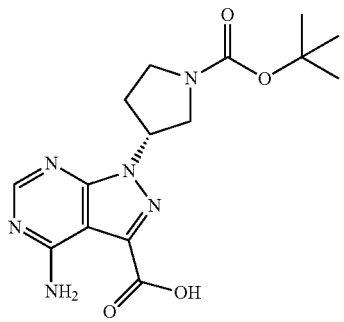 [SMILES: CC(C)(C)OC(=O)N1CC[C@@H](n2nc(C(=O)O)c3c(N)ncnc32)C1]

(Step 1) Synthesis of (S)-tert-butyl 3-(methylsulfonyloxy)pyrrolidine-1-carboxylate (S)-(−)-N-Boc-3-pyrrolidinol (935 mg) was dissolved in chloroform (15 mL). To the solution, triethylamine (1.04 mL) and methanesulfonyl chloride (467 μL) were added under ice cooling. The mixture was stirred at room temperature for 1.5 hours, and then, ethyl acetate and water were added thereto to separate an organic layer. The organic layer was washed with a saturated aqueous solution of sodium bicarbonate, a saturated aqueous solution of ammonium chloride, and water and then dried over anhydrous sodium sulfate, and the solvent was distilled off under reduced pressure to obtain 1.3 g of the title compound as a colorless oil.

Physical property value: m/z [M+H]$^+$ 266.1

(Step 2) Synthesis of (R)-tert-butyl 3-(4-amino-3-iodo-1H-pyrazolo[3,4-d]pyrimidin-1-yl)pyrrolidine-1-carboxylate 3-Iodo-1H-pyrazolo[3,4-d]pyrimidin-4-amine (20.0 g) synthesized by the method described in the pamphlet of International Publication No. WO 2007/126841, (S)-tert-butyl 3-(methylsulfonyloxy) pyrrolidine-1-carboxylate (23 g) obtained in (Step 1), and potassium carbonate (32 g) were suspended in DMA (200 mL), and the suspension was heated to 85° C. and stirred for 3 hours. After the mixture was cooled to room temperature, water (400 mL) was added thereto, and the precipitated solid was collected by filtration, washed with water, and then dried to obtain 23.5 g of the title compound as a pale yellow solid.

Physical property value: m/z [M+H]$^+$ 431.0

(Step 3) Synthesis of (R)-4-amino-1-(1-(tert-butyloxycarbonyl) pyrrolidin-3-yl)-1H-pyrazolo[3,4-d]pyrimidine-3-carboxylic acid (R)-tert-Butyl 3-(4-amino-3-iodo-1H-pyrazolo[3,4-d]pyrimidin-1-yl)pyrrolidine-1-carboxylate (2.0 g) obtained in (Step 2), 2-diethylaminoethanol (3.1 mL), and Pd(PPh$_3$)$_2$Cl$_2$ (163 mg) were dissolved in NMP (20 mL). After the system was purged with carbon monoxide, the solution was heated to 120° C. The solution was stirred for 1 hour and then cooled to room temperature. Methanol (10 mL) was added thereto, then a 5 N aqueous sodium hydroxide solution (6 mL) was added thereto, and the mixture was stirred for 10 minutes. After water was added, the aqueous layer was washed with chloroform and adjusted to pH 4 with hydrochloric acid, and the precipitated solid was collected by filtration, washed with water, and then dried to obtain 1.35 g of the title compound as a pale yellow solid.

Physical property value: m/z [M+H]$^+$ 349.1

Reference Example 5 Synthesis of (R)-1-(1-acryloylpyrrolidin-3-yl)-1H-pyrazolo[3,4-d]pyrimidine-3-carboxylic acid

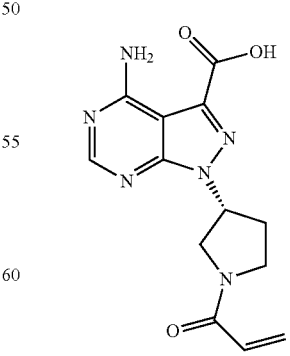

To (R)-4-amino-1-(1-(tert-butyloxycarbonyl) pyrrolidin-3-yl)-1H-pyrazolo[3,4-d]pyrimidine-3-carboxylic acid (1.0 g) obtained in Reference Example 4, 4 N hydrochloric acid/1,4-dioxane (5 mL) was added, and the mixture was stirred for 1 hour. Then, the solvent was removed with an evaporator. Chloroform (28 mL) and triethylamine (1.5 mL) were added to the residue, and the mixture was cooled in ice, followed by adding acryloyl chloride (0.21 mL). The mixture was stirred for 1.5 hours, and then, the solvent was removed with an evaporator. To the residue, formic acid was added until adjusting to pH 3.0, and the mixture was stirred for 2 hours. Then, the precipitated solid was collected by filtration and dried under reduced pressure to obtain 0.859 g of the title compound as a white-brown solid.

Physical property value: m/z [M+H]$^+$ 303.3

Example 1 Synthesis of (R)-1-(1-acryloylpiperidin-3-yl)-4-amino-N-(5-bromo-4-(2-(dimethylamino)-2-oxoethyl)-2-methylphenyl)-1H-pyrazolo[3,4-d]pyrimidine-3-carboxamide (Step 1) Synthesis of 2-(2-bromo-5-methyl-4-nitrophenyl)acetic acid According to the method described in the pamphlet of International Publication No. WO 2012/058134, NMP (10 mL) was added to diethyl malonate (2.4 g). Then, the solution was cooled in an ice bath, and sodium hydride (960 mg) was added thereto. The mixture was stirred at 0° C. for 30 minutes, and then, 1-bromo-2-fluoro-4-methyl-5-nitrobenzene (2.34 g) was added thereto. The mixture was stirred at room temperature for 1 hour, and then, ethyl acetate and water were added thereto to separate an organic layer. The organic layer was washed with a saturated aqueous solution of ammonium chloride and then dried over anhydrous sodium sulfate, and the solvent was distilled off under reduced pressure. The residue was purified by silica gel column chromatography (hexane/ethyl acetate) to obtain 3.13 g of a colorless oil. Next, methanol (30 mL) and a 5 M aqueous sodium hydroxide solution (7.5 mL) were added to the obtained oil, and the mixture was heated to reflux for 5 hours. After the solution was cooled to room temperature, the solvent was distilled off under reduced pressure, and a 2 M aqueous hydrochloric acid solution was added to the residue. The precipitated solid was collected by filtration and dried to obtain 1.18 g of the title compound as a yellow solid.

(Step 2) Synthesis of 2-(2-bromo-5-methyl-4-nitrophenyl)-N,N-dimethylacetamide 2-(2-Bromo-5-methyl-4-nitrophenyl)acetic acid (1.15 g) obtained in (Step 1) was dissolved in dichloromethane (20 mL). To the solution, oxalyl chloride (0.426 mL) and DMF (0.0653 mL) were added under ice cooling, and then, the mixture was stirred at room temperature for 2 hours. After concentration of the solution, toluene was added to the residue, and the mixture was concentrated again. The obtained light brown oil was dissolved in chloroform (30 mL). To the solution, a 2.0 M solution of dimethylamine in THF (10.5 mL) was added, and the mixture was stirred for 1 hour. The solution was concentrated, and the residue was dissolved in chloroform and washed with water. The obtained organic layer was dried over anhydrous sodium sulfate, filtered, and concentrated, and then, the residue was purified by silica gel chromatography (eluent:hexane-ethyl acetate) to obtain the title compound (1.15 g) as a yellow solid.

(Step 3) Synthesis of 2-(4-amino-2-bromo-5-methylphenyl)-N,N-dimethylacetamide

To 2-(2-bromo-5-methyl-4-nitrophenyl)-N,N-dimethylacetamide (300 mg) obtained in (Step 2), ethanol (3 mL) and water (3 mL) were added, and then, ammonium chloride (300 mg) and iron powder (300 mg) were added. The solution was heated to 70° C., stirred for 2 hours, then cooled to room temperature, and filtered through celite to remove iron. Ethyl acetate was added to the filtrate for extraction. The extract was dried over anhydrous sodium sulfate, and the solvent was distilled off under reduced pressure. The obtained residue was purified by silica gel chromatography (hexane/ethyl acetate) to obtain 200 mg of the title compound as a yellow solid.

(Step 4) Synthesis of Example Compound 1

(R)-1-(1-Acryloylpiperidin-3-yl)-4-amino-1H-pyrazolo[3,4-d]pyrimidine-3-carboxylic acid (50 mg) obtained in Reference Example 3 and 2-(4-amino-2-bromo-5-methylphenyl)-N,N-dimethylacetamide (64 mg) obtained in (Step 3) were dissolved by adding DMF (1 mL) and DIPEA (0.055 mL). To the solution, HATU (90 mg) was then added. The mixture was stirred at room temperature for 1 hour, then purified by reverse-phase preparative HPLC purification (water/acetonitrile (0.1% formic acid)), and concentrated, and then, the residue was dissolved in chloroform, washed with a saturated aqueous solution of sodium carbonate, dried using anhydrous sodium sulfate, and concentrated. Then, the obtained residue was suspended in ethyl acetate-hexane, and the suspension was filtered to obtain 58 mg of the title compound as an off-white solid.

Example 2 Synthesis of (R)-1-(1-acryloylpiperidin-3-yl)-4-amino-N-(2-chloro-4-(2-(dimethylamino)-2-oxoethyl)-5-methylphenyl)-1H-pyrazolo[3,4-d]pyrimidine-3-carboxamide (Step 1) Synthesis of 2-(5-chloro-2-methyl-4-nitrophenyl)acetic acid According to (Step 1) of Example 1, 952 mg of the title compound was obtained as a pale yellow solid by using 1-chloro-5-fluoro-4-methyl-2-nitrobenzene (1.00 g) instead of 1-bromo-2-fluoro-4-methyl-5-nitrobenzene.

(Step 2) Synthesis of 2-(5-chloro-2-methyl-4-nitrophenyl)-N,N-dimethylacetamide

According to (Step 2) of Example 1, 1.03 g of the title compound was obtained as a pale yellow solid by using 2-(5-chloro-2-methyl-4-nitrophenyl)acetic acid (922 mg) obtained in (Step 1) instead of 2-(2-bromo-5-methyl-4-nitrophenyl)acetic acid.

(Step 3) Synthesis of 2-(4-amino-5-chloro-2-methylphenyl)-N,N-dimethylacetamide

According to (Step 3) of Example 1, 720 mg of the title compound was obtained as a pale yellow solid by using 2-(5-chloro-2-methyl-4-nitrophenyl)-N,N-dimethylacetamide (1.03 g) obtained in (Step 2) instead of 2-(2-bromo-5-methyl-4-nitrophenyl)-N,N-dimethylacetamide.

(Step 4) Synthesis of Example Compound 2

According to (Step 4) of Example 1, (R)-1-(1-acryloylpiperidin-3-yl)-4-amino-1H-pyrazolo[3,4-d]pyrimidine-3-carboxylic acid (66.5 mg) and 2-(4-amino-2-chloro-5-methylphenyl)-N,N-dimethylacetamide (95.3 mg) obtained in (Step 3) were dissolved by adding DMSO (0.665 mL) and DIPEA (73.2 μL). To the solution, HATU (240 mg) was then added to obtain 56.2 mg of the title compound as a white solid.

Example 3 Synthesis of (R)-1-(1-acryloylpiperidin-3-yl)-4-amino-N-(2-chloro-4-(2-(dimethylamino)-2-oxoethyl)-3-methylphenyl)-1H-pyrazolo[3,4-d]pyrimidine-3-carboxamide (Step 1) Synthesis of 2-(3-chloro-2-methyl-4-nitrophenyl)acetic acid According to (Step 1) of Example 1, 1.23 g of the title compound was obtained as a pale yellow solid by using 2-chloro-4-fluoro-3-methyl-1-nitrobenzene (1.00 g) instead of 1-bromo-2-fluoro-4-methyl-5-nitrobenzene.

(Step 2) Synthesis of 2-(3-chloro-2-methyl-4-nitrophenyl)-N,N-dimethylacetamide

According to (Step 2) of Example 1, 900 mg of the title compound was obtained as a pale yellow solid by using 2-(3-chloro-2-methyl-4-nitrophenyl)acetic acid (1.23 g) obtained in (Step 1) instead of 2-(2-bromo-5-methyl-4-nitrophenyl)acetic acid.

(Step 3) Synthesis of 2-(4-amino-3-chloro-2-methylphenyl)-N,N-dimethylacetamide

According to (Step 3) of Example 1, 590 mg of the title compound was obtained as a white solid by using 2-(3-chloro-2-methyl-4-nitrophenyl)-N,N-dimethylacetamide (900 mg) obtained in (Step 2) instead of 2-(2-bromo-5-methyl-4-nitrophenyl)-N,N-dimethylacetamide.

(Step 4) Synthesis of Example Compound 3

According to (Step 4) of Example 1, (R)-1-(1-acryloylpiperidin-3-yl)-4-amino-1H-pyrazolo[3,4-d]pyrimidine-3-carboxylic acid (66.5 mg) and 2-(4-amino-3-chloro-2-methylphenyl)-N,N-dimethylacetamide (95.3 mg) obtained in (Step 3) were dissolved by adding DMSO (0.665 mL) and DIPEA (73.2 μL). To the solution, HATU (240 mg) was then added to obtain 78.2 mg of the title compound as a white solid.

Example 4 Synthesis of (R)-1-(1-acryloylpiperidin-3-yl)-4-amino-N-(4-(2-(dimethylamino)-2-oxo-ethyl)-2-methylphenyl)-1H-pyrazolo[3,4-d]pyrimidine-3-carboxamide (Step 1) Synthesis of N,N-dimethyl-2-(3-methyl-4-nitrophenyl)acetamide 3-Methyl-4-nitrophenylacetic acid (50 mg) was dissolved by adding DMF (1.3 mL), DIEPA (0.13 mL), and a 2.0 M solution of dimethylamine in THF (0.38 mL). To the solution, HATU (145 mg) was then added. The mixture was stirred at room temperature for 2 hours, and then, ethyl acetate and water were added thereto to separate an organic layer. The organic layer was washed with a saturated aqueous solution of sodium bicarbonate, a saturated aqueous solution of ammonium chloride, and water and then dried over anhydrous sodium sulfate, and the solvent was distilled off under reduced pressure. The residue was purified by silica gel chromatography (hexane/ethyl acetate) to obtain 50 mg of the title compound as a colorless oil.

(Step 2) Synthesis of 2-(4-amino-3-methylphenyl)-N,N-dimethylacetamide

N,N-Dimethyl-2-(3-methyl-4-nitrophenyl)acetamide (50 mg) obtained in (Step 1) was dissolved in methanol (2.2 mL). To the solution, 10% Pd on carbon (5 mg) was then added. The mixture was stirred overnight in a hydrogen atmosphere and then filtered through celite to remove Pd on carbon. The solvent was distilled off under reduced pressure to obtain 40 mg of the title compound as a colorless oil.

(Step 3) Synthesis of Example Compound 4

(R)-1-(1-Acryloylpiperidin-3-yl)-4-amino-1H-pyrazolo[3,4-d]pyrimidine-3-carboxylic acid (10 mg) obtained in Reference Example 3 and 2-(4-amino-3-methylphenyl)-N,N-dimethylacetamide (9.2 mg) obtained in (Step 2) were dissolved by adding DMF (0.2 mL) and DIPEA (20 μL). To the solution, HATU (18 mg) was then added. The mixture was stirred at room temperature for 1 hour. Then, DMSO (1 mL) was added thereto, and the mixture was purified by reverse-phase preparative HPLC purification (water/acetonitrile (0.1% formic acid)) to obtain 3.4 mg of the title compound as a white solid.

Example 5 Synthesis of (R)-1-(1-acryloylpiperidin-3-yl)-4-amino-N-(4-(2-(dimethylamino)-2-oxoethyl)naphthalen-1-yl)-1H-pyrazolo[3,4-d]pyrimidine-3-carboxamide (Step 1) Synthesis of N,N-dimethyl-2-(4-nitronaphthalen-1-yl)acetamide 1-Naphthylacetic acid (500 mg) was dissolved in DMF. To the solution, a 2.0 M solution of diethylamine in THF (2.7 mL), DIPEA (1.4 mL), and HATU (1.3 g) were then added. The mixture was stirred at room temperature for 2 hours, and then, ethyl acetate and water were added thereto to separate an organic layer. The organic layer was washed with a saturated aqueous solution of sodium bicarbonate and water and then dried over anhydrous sodium sulfate, and the solvent was distilled off under reduced pressure. Sulfuric acid (5 mL) was added to the obtained residue, and the solution was cooled to 0° C. Then, fuming nitric acid (1 mL) was added dropwise thereto. The mixture was stirred at 0° C. for 30 minutes, and then, the solution was added to an aqueous sodium bicarbonate solution and neutralized, followed by extraction with ethyl acetate. The extract was dried over anhydrous sodium sulfate, and the solvent was distilled off under reduced pressure. The obtained residue was purified by silica gel chromatography (hexane/ethyl acetate) to obtain 310 mg of the title compound as a yellow solid.

(Step 2) Synthesis of 2-(4-aminonaphthalen-1-yl)-N,N-dimethylacetamide

According to (Step 2) of Example 4, 18 mg of the title compound was obtained as a colorless oil by using N,N-dimethyl-2-(4-nitronaphthalen-1-yl)acetamide (20 mg).

(Step 3) Synthesis of Example Compound 5

According to (Step 3) of Example 4, 8.9 mg of the title compound was obtained as a white solid by using (R)-1-(1- acryloylpiperidin-3-yl)-4-amino-1H-pyrazolo[3,4-d]pyrimidine-3-carboxylic acid (10 mg) and 2-(4-aminonaphthalen-1-yl)-N,N-dimethylacetamide (11 mg) obtained in (Step 2).

Example 6 Synthesis of (R)-1-(1-acryloylpiperidin-3-yl)-4-amino-N-(2-chloro-4-(2-(dimethylamino)-2-oxoethyl)phenyl)-1H-pyrazolo[3,4-d]pyrimidine-3-carboxamide (Step 1) Synthesis of 2-(3-chloro-4-nitrophenyl)-N,N-dimethylacetamide According to (Step 1) of Example 4, 890 mg of the title compound was obtained as a brown oil by using 2-(3-chloro-4-nitrophenyl)acetic acid (980 mg) instead of 3-methyl-4-nitrophenylacetic acid.

(Step 2) Synthesis of 2-(4-amino-3-chlorophenyl)-N,N-dimethylacetamide

To 2-(3-chloro-4-nitrophenyl)-N,N-dimethylacetamide (1.4 g) obtained in (Step 1), ethanol (14 mL) and water (14 mL) were added, and then, ammonium chloride (1.4 g) and iron powder (1.4 g) were added. The solution was heated to 70° C., stirred for 2 hours, then cooled to room temperature, and filtered through celite to remove iron. Ethyl acetate was added to the filtrate for extraction. The extract was dried over anhydrous sodium sulfate, and the solvent was distilled off under reduced pressure. The obtained residue was purified by silica gel chromatography (hexane/ethyl acetate) to obtain 1.1 g of the title compound as a yellow solid.

(Step 3) Synthesis of Example Compound 6

According to (Step 3) of Example 4, 6.0 mg of the title compound was obtained as a white solid by using (R)-1-(1-acryloylpiperidin-3-yl)-4-amino-1H-pyrazolo[3,4-d]pyrimidine-3-carboxylic acid (25 mg) and 2-(4-amino-3-chlorophenyl)-N,N-dimethylacetamide (25 mg) obtained in (Step 2).

Example 7 Synthesis of (R)-1-(1-acryloylpiperidin-3-yl)-4-amino-N-(4-(2-(dimethylamino)-2-oxoethyl)-2-methoxyphenyl)-1H-pyrazolo[3,4-d]pyrimidine-3-carboxamide (Step 1) Synthesis of 2-(3-methoxy-4-nitrophenyl)-N,N-dimethylacetamide According to the synthesis method described in European Journal of Medicinal Chemistry, 46 (1), 285-296; 2010, 480 mg of the title compound was obtained as a yellow oil by using 3-methoxy-4-nitrobenzaldehyde (510 mg) instead of 4-nitrobenzaldehyde.

(Step 2) Synthesis of 2-(4-amino-3-methoxyphenyl)-N,N-dimethylacetamide

According to (Step 2) of Example 6, 450 mg of the title compound was obtained as a yellow oil by using 2-(3-methoxy-4-nitrophenyl)-N,N-dimethylacetamide (480 mg) instead of 2-(3-chloro-4-nitrophenyl)-N,N-dimethylacetamide.

(Step 3) Synthesis of Example Compound 7

According to (Step 3) of Example 4, 18 mg of the title compound was obtained as a white solid by using (R)-1-(1-acryloylpiperidin-3-yl)-4-amino-1H-pyrazolo[3,4-d]pyrimidine-3-carboxylic acid (30 mg) and 2-(4-amino-3-methoxyphenyl)-N,N-dimethylacetamide (29 mg) obtained in (Step 2).

Example 8 Synthesis of (R)-1-(1-acryloylpiperidin-3-yl)-4-amino-N-(3-chloro-4-(2-(dimethylamino)-2-oxoethyl)phenyl)-1H-pyrazolo[3,4-d]pyrimidine-3-carboxamide (Step 1) Synthesis of 2-(2-chloro-4-nitrophenyl)-N,N-dimethylacetamide According to (Step 1) of Example 4, 220 mg of the title compound was obtained as a yellow solid by using 2-(2-chloro-4-nitrophenyl)acetic acid (220 mg) instead of 3-methyl-4-nitrophenylacetic acid.

(Step 2) Synthesis of 2-(4-amino-2-chlorophenyl)-N,N-dimethylacetamide

According to (Step 2) of Example 6, 180 mg of the title compound was obtained as a yellow oil by using 2-(2-chloro-4-nitrophenyl)-N,N-dimethylacetamide (220 mg) instead of 2-(3-chloro-4-nitrophenyl)-N,N-dimethylacetamide.

(Step 3) Synthesis of Example Compound 8

According to (Step 3) of Example 4, 13.5 mg of the title compound was obtained as a white solid by using (R)-1-(1-acryloylpiperidin-3-yl)-4-amino-1H-pyrazolo[3,4-d]pyrimidine-3-carboxylic acid (10 mg) and 2-(4-amino-2-chlorophenyl)-N,N-dimethylacetamide (10 mg) obtained in (Step 2).

Example 9 Synthesis of (R)-1-(1-acryloylpiperidin-3-yl)-4-amino-N-(5-chloro-4-(2-(dimethylamino)-2-oxoethyl)-2-methoxyphenyl)-1H-pyrazolo[3,4-d]pyrimidine-3-carboxamide (Step 1) Synthesis of 2-(2-chloro-5-methoxy-4-nitrophenyl)-N,N-dimethylacetamide According to (Step 1) of Example 4, 388 mg of the title compound was obtained as a yellow solid by using 2-(2-chloro-5-methoxy-4-nitrophenyl)acetic acid (350 mg) instead of 3-methyl-4-nitrophenylacetic acid.

(Step 2) Synthesis of 2-(4-amino-2-chloro-5-methoxyphenyl)-N,N-dimethylacetamide According to (Step 2) of Example 6, 340 mg of the title compound was obtained as a yellow oil by using 2-(2-chloro-5-methoxy-4-nitrophenyl)-N,N-dimethylacetamide (388 mg) instead of 2-(3-chloro-4-nitrophenyl)-N,N-dimethylacetamide.

(Step 3) Synthesis of Example Compound 9

According to (Step 3) of Example 4, 17.5 mg of the title compound was obtained as a white solid by using (R)-1-(1-acryloylpiperidin-3-yl)-4-amino-1H-pyrazolo[3,4-d]pyrimidine-3-carboxylic acid (10 mg) and 2-(4-amino-2-chloro-5-methoxyphenyl)-N,N-dimethylacetamide (10 mg) obtained in (Step 2).

Example 10 Synthesis of (R)-1-(1-acryloylpiperidin-3-yl)-4-amino-N-(4-(2-(dimethylamino)-2-oxoethyl)-5-fluoro-2-methylphenyl)-1H-pyrazolo[3,4-d]pyrimidine-3-carboxamide (Step 1) Synthesis of 2-(2-fluoro-5-methyl-4-nitrophenyl)acetic acid According to the method described in the pamphlet of International Publication No. WO 2012/058134, NMP (30 mL) was added to diethyl malonate (1.0 g). Then, the solution was cooled in an ice bath, and sodium hydride (380 mg) was added thereto. The mixture was stirred at 0° C. for 30 minutes, and then, 1,2-difluoro-4-methyl-5-nitrobenzene (690 mg) was added thereto. The mixture was stirred at room temperature for 1 hour, and then, ethyl acetate and water were added thereto to separate an organic layer. The organic layer was washed with a saturated aqueous solution of ammonium chloride and then dried over anhydrous sodium sulfate, and the solvent was distilled off under reduced pressure. The residue was purified by silica gel chromatography (hexane/ethyl acetate) to obtain 1.20 g of a colorless oil. Next, methanol (10 mL) and a 5 M aqueous sodium hydroxide solution (2.5 mL) were added to the obtained oil, and the mixture was heated to reflux for 5 hours. After the solution was cooled to room temperature, the solvent was distilled off under reduced pressure, and a 2 M aqueous hydrochloric acid solution was added to the residue. The precipitated solid was collected by filtration and dried to obtain 610 mg of the title compound as a yellow solid.

(Step 2) Synthesis of 2-(2-fluoro-5-methyl-4-nitrophenyl)-N,N-dimethylacetamide

According to (Step 1) of Example 4, 600 mg of the title compound was obtained as a yellow oil by using 2-(2-fluoro-5-methyl-4-nitrophenyl)acetic acid (610 mg) instead of 3-methyl-4-nitrophenylacetic acid.

(Step 3) Synthesis of 2-(4-amino-2-fluoro-5-methylphenyl)-N,N-dimethylacetamide

According to (Step 2) of Example 6, 540 mg of the title compound was obtained as a yellow oil by using 2-(2-fluoro-5-methyl-4-nitrophenyl)-N,N-dimethylacetamide (600 mg) instead of 2-(3-chloro-4-nitrophenyl)-N,N-dimethylacetamide.

(Step 4) Synthesis of Example Compound 10

According to (Step 3) of Example 4, 7.3 mg of the title compound was obtained as a white solid by using (R)-1-(1-acryloylpiperidin-3-yl)-4-amino-1H-pyrazolo[3,4-d]pyrimidine-3-carboxylic acid (10 mg) and 2-(4-amino-2-fluoro-5-methylphenyl)-N,N-dimethylacetamide (10 mg) obtained in (Step 3).

Example 11 Synthesis of (R)-1-(1-acryloylpiperidin-3-yl)-4-amino-N-(3-chloro-4-(2-(dimethylamino)-2-oxoethyl)-2-methoxyphenyl)-1H-pyrazolo[3,4-d]pyrimidine-3-carboxamide (Step 1) Synthesis of 2-(2-chloro-3-methoxy-4-nitrophenyl)acetic acid According to (Step 1) of Example 10, 710 mg of the title compound was obtained as a yellow solid by using 2-chloro-1-fluoro-3-methoxy-4-nitrobenzene (800 mg) instead of 1,2-difluoro-4-methyl-5-nitrobenzene.

(Step 2) Synthesis of 2-(2-chloro-3-methoxy-4-nitrophenyl)-N,N-dimethylacetamide According to (Step 1) of Example 4, 110 mg of the title compound was obtained as a yellow oil by using 2-(2-chloro-3-methoxy-4-nitrophenyl)acetic acid (100 mg) obtained in (Step 1) instead of 3-methyl-4-nitrophenylacetic acid.

(Step 3) Synthesis of 2-(4-amino-2-chloro-3-methoxyphenyl)-N,N-dimethylacetamide According to (step 2) of Example 6, 95 mg of the title compound was obtained as a yellow oil by using 2-(2-chloro-3-methoxy-4-nitrophenyl)-N,N-dimethylacetamide (110 mg) obtained in (Step 2) instead of 2-(3-chloro-4-nitrophenyl)-N,N-dimethylacetamide.

(Step 4) Synthesis of Example Compound 11

According to (Step 3) of Example 4, 6.9 mg of the title compound was obtained as a white solid by using (R)-1-(1-acryloylpiperidin-3-yl)-4-amino-1H-pyrazolo[3,4-d]pyrimidine-3-carboxylic acid (10 mg) and 2-(4-amino-2-chloro-3-methoxyphenyl)-N,N-dimethylacetamide (10 mg) obtained in (Step 3).

Example 12 Synthesis of (R)-1-(1-acryloylpiperidin-3-yl)-4-amino-N-(4-(2-(dimethylamino)-2-oxoethyl)-3-fluoro-2-methylphenyl)-1H-pyrazolo[3,4-d]pyrimidine-3-carboxamide (Step 1) Synthesis of 2-(2-fluoro-3-methyl-4-nitrophenyl)acetic acid According to (Step 1) of Example 10, 800 mg of the title compound was obtained as a yellow solid by using 1,2-difluoro-3-methyl-4-nitrobenzene (560 mg) instead of 1,2-difluoro-4-methyl-5-nitrobenzene.

(Step 2) Synthesis of 2-(2-fluoro-3-methyl-4-nitrophenyl)-N,N-dimethylacetamide

According to (Step 1) of Example 4, 290 mg of the title compound was obtained as a yellow oil by using 2-(2-fluoro-3-methyl-4-nitrophenyl)acetic acid (260 mg) obtained in (Step 1) instead of 3-methyl-4-nitrophenylacetic acid.

(Step 3) Synthesis of 2-(4-amino-2-fluoro-3-methylphenyl)-N,N-dimethylacetamide

According to (Step 2) of Example 6, 230 mg of the title compound was obtained as a yellow oil by using 2-(2-fluoro-3-methyl-4-nitrophenyl)-N,N-dimethylacetamide (290 mg) obtained in (Step 2) instead of 2-(3-chloro-4-nitrophenyl)-N,N-dimethylacetamide.

(Step 4) Synthesis of Example Compound 12

According to (Step 3) of Example 4, 8.2 mg of the title compound was obtained as a white solid by using (R)-1-(1-acryloylpiperidin-3-yl)-4-amino-1H-pyrazolo[3,4-d]pyrimidine-3-carboxylic acid (10 mg) and 2-(4-amino-2-fluoro-3-methylphenyl)-N,N-dimethylacetamide (10 mg) obtained in (Step 3).

Example 13 Synthesis of (R)-1-(1-acryloylpiperidin-3-yl)-4-amino-N-(4-(2-(dimethylamino)-2-oxoethyl)-2,3-dimethylphenyl)-1H-pyrazolo[3,4-d]pyrimidine-3-carboxamide (Step 1) Synthesis of 2-(2,3-dimethyl-4-nitrophenyl)acetic acid According to (Step 1) of Example 10, 1.12 g of the title compound was obtained as a yellow solid by using 1-fluoro-2,3-dimethyl-4-nitrobenzene (1.2 g) instead of 1,2-difluoro-4-methyl-5-nitrobenzene.

(Step 2) Synthesis of 2-(2,3-dimethyl-4-nitrophenyl)-N,N-dimethylacetamide

According to (Step 1) of Example 4, 1.30 g of the title compound was obtained as a yellow oil by using 2-(2,3-dimethyl-4-nitrophenyl)acetic acid (1.12 g) obtained in (Step 1) instead of 3-methyl-4-nitrophenylacetic acid.

(Step 3) Synthesis of 2-(4-amino-2,3-dimethylphenyl)-N,N-dimethylacetamide

According to (Step 2) of Example 6, 1.03 g of the title compound was obtained as a yellow oil by using 2-(2,3-dimethyl-4-nitrophenyl)-N,N-dimethylacetamide (1.26 g) obtained in (Step 2) instead of 2-(3-chloro-4-nitrophenyl)-N,N-dimethylacetamide.

(Step 4) Synthesis of Example Compound 13

According to (Step 3) of Example 4, 48 mg of the title compound was obtained as a white solid by using (R)-1-(1-acryloylpiperidin-3-yl)-4-amino-1H-pyrazolo[3,4-d]pyrimidine-3-carboxylic acid (40 mg) and 2-(2,3-dimethyl-4-nitrophenyl)-N,N-dimethylacetamide (31 mg) obtained in (Step 3).

Example 14 Synthesis of (R)-1-(1-acryloylpiperidin-3-yl)-4-amino-N-(4-(2-(dimethylamino)-2-oxoethyl)-3-fluoro-2-methoxyphenyl)-1H-pyrazolo[3,4-d]pyrimidine-3-carboxamide (Step 1) Synthesis of 2-(2-fluoro-3-methoxy-4-nitrophenyl)acetic acid According to (Step 1) of Example 10, 1.10 g of the title compound was obtained as a yellow solid by using 1,2-difluoro-3-methoxy-4-nitrobenzene (1.0 g) instead of 1,2-difluoro-4-methyl-5-nitrobenzene.

(Step 2) Synthesis of 2-(2-fluoro-3-methoxy-4-nitrophenyl)-N,N-dimethylacetamide According to (Step 1) of Example 4, 120 mg of the title compound was obtained as a yellow oil by using 2-(2-fluoro-3-methoxy-4-nitrophenyl)acetic acid (100 mg) obtained in (Step 1) instead of 3-methyl-4-nitrophenylacetic acid.

(Step 3) Synthesis of 2-(4-amino-2-fluoro-3-methoxyphenyl)-N,N-dimethylacetamide According to (Step 2) of Example 6, 100 mg of the title compound was obtained as a yellow oil by using 2-(2-fluoro-3-methoxy-4-nitrophenyl)-N,N-dimethylacetamide (120 mg) obtained in (Step 2) instead of 2-(3-chloro-4-nitrophenyl)-N,N-dimethylacetamide.

(Step 4) Synthesis of Example Compound 14

According to (Step 3) of Example 4, 4.9 mg of the title compound was obtained as a yellow solid by using (R)-1-(1-acryloylpiperidin-3-yl)-4-amino-1H-pyrazolo[3,4-d]pyrimidine-3-carboxylic acid (10 mg) and 2-(4-amino-2-fluoro-3-methoxyphenyl)-N,N-dimethylacetamide (10 mg) obtained in (Step 3).

Example 15 Synthesis of (R)-1-(1-acryloylpiperidin-3-yl)-4-amino-N-(2-(difluoromethoxy)-4-(2-(dimethylamino)-2-oxoethyl)phenyl)-1H-pyrazolo[3,4-d]pyrimidine-3-carboxamide (Step 1) Synthesis of 2-(3-(difluoromethoxy)-4-nitrophenyl)-N,N-dimethylacetamide According to (Step 1) of Example 4, 450 mg of 2-(3-hydroxy-4-nitrophenyl)-N,N-dimethylacetamide was obtained as a yellow oil by using 2-(3-hydroxy-4-nitrophenyl)acetic acid (420 mg) instead of 3-methyl-4-nitrophenylacetic acid. Next, DMF (4.5 mL) and potassium carbonate (250 mg) were added to the obtained 2-(3-hydroxy-4-nitrophenyl)-N,N-dimethylacetamide (200 mg), and sodium 2-chloro-2,2-difluoroacetate (270 mg) was added to the suspension. The mixture was stirred at room temperature for 1 hour, and then, ethyl acetate and water were added thereto to separate an organic layer. The organic layer was washed with a saturated aqueous solution of ammonium chloride and then dried over anhydrous sodium sulfate, and the solvent was distilled off under reduced pressure. The residue was purified by silica gel chromatography (hexane/ethyl acetate) to obtain 155 mg of the title compound as a yellow solid.

(Step 2) Synthesis of 2-(4-amino-3-(difluoromethoxy)phenyl)-N,N-dimethylacetamide According to (Step 2) of Example 6, 120 mg of the title compound was obtained as a yellow oil by using 2-(3-(difluoromethoxy)-4-nitrophenyl)-N,N-dimethylacetamide (155 mg) obtained in (Step 1) instead of 2-(3-chloro-4-nitrophenyl)-N,N-dimethylacetamide.

(Step 3) Synthesis of Example Compound 15

According to (Step 3) of Example 4, 13.5 mg of the title compound was obtained as a yellow solid by using (R)-1-(1-acryloylpiperidin-3-yl)-4-amino-1H-pyrazolo[3,4-d]pyrimidine-3-carboxylic acid (10 mg) and 2-(4-amino-3-(difluoromethoxy)phenyl)-N,N-dimethylacetamide (10 mg) obtained in (Step 2).

Example 16 Synthesis of (R)-1-(1-acryloylpiperidin-3-yl)-4-amino-N-(4-(2-(dimethylamino)-2-oxoethyl)-2-(fluoromethoxy)phenyl)-1H-pyrazolo[3,4-d]pyrimidine-3-carboxamide (Step 1) Synthesis of 2-(3-(fluoromethoxy)-4-nitrophenyl)-N,N-dimethylacetamide According to (Step 1) of Example 4, 450 mg of 2-(3-hydroxy-4-nitrophenyl)-N,N-dimethylacetamide was obtained as a yellow oil by using 2-(3-hydroxy-4-nitrophenyl)acetic acid (420 mg) instead of 3-methyl-4-nitrophenylacetic acid. Next, DMF (4.5 mL) and potassium carbonate (370 mg) were added to the obtained 2-(3-hydroxy-4-nitrophenyl)-N,N-dimethylacetamide (200 mg), and bromo-fluoromethane (200 mg) was added to the suspension. The mixture was stirred at room temperature for 1 hour, and then, ethyl acetate and water were added thereto to separate an organic layer. The organic layer was washed with a saturated aqueous solution of ammonium chloride and then dried over anhydrous sodium sulfate, and the solvent was distilled off under reduced pressure. The residue was purified by silica gel chromatography (hexane/ethyl acetate) to obtain 145 mg of the title compound as a yellow solid.

(Step 2) Synthesis of 2-(4-amino-3-(fluoromethoxy)phenyl)-N,N-dimethylacetamide

According to (Step 2) of Example 6, 110 mg of the title compound was obtained as a yellow oil by using 2-(3-(fluoromethoxy)-4-nitrophenyl)-N,N-dimethylacetamide (145 mg) obtained in (Step 1) instead of 2-(3-chloro-4-nitrophenyl)-N,N-dimethylacetamide.

(Step 3) Synthesis of Example Compound 16

According to (Step 3) of Example 4, 14.5 mg of the title compound was obtained as a yellow solid by using (R)-1-(1-acryloylpiperidin-3-yl)-4-amino-1H-pyrazolo[3,4-d]pyrimidine-3-carboxylic acid (10 mg) and 2-(4-amino-3-(fluoromethoxy)phenyl)-N,N-dimethylacetamide (10 mg) obtained in (Step 2).

Example 17 Synthesis of (R)-1-(1-acryloylpiperidin-3-yl)-4-amino-N-(2-bromo-4-(2-(dimethylamino)-2-oxoethyl)phenyl)-1H-pyrazolo[3,4-d]pyrimidine-3-carboxamide (Step 1) Synthesis of 2-(3-bromo-4-nitrophenyl)-N,N-dimethylacetamide According to (Step 1) of Example 4, 440 mg of the title compound was obtained as a yellow oil by using 2-(3-bromo-4-nitrophenyl)acetic acid (430 mg) instead of 3-methyl-4-nitrophenylacetic acid.

(Step 2) Synthesis of 2-(4-amino-3-bromophenyl)-N,N-dimethylacetamide

According to (Step 2) of Example 6, 80 mg of the title compound was obtained as a yellow oil by using 2-(3-bromo-4-nitrophenyl)-N,N-dimethylacetamide (100 mg) obtained in (Step 1) instead of 2-(3-chloro-4-nitrophenyl)-N,N-dimethylacetamide.

(Step 3) Synthesis of Example Compound 17

According to (Step 3) of Example 4, 2.10 mg of the title compound was obtained as a white solid by using (R)-1-(1-acryloylpiperidin-3-yl)-4-amino-1H-pyrazolo[3,4-d]pyrimidine-3-carboxylic acid (10 mg) and 2-(4-amino-3-bromophenyl)-N,N-dimethylacetamide (10 mg) obtained in (Step 2).

Example 18 Synthesis of (R)-1-(1-acryloylpiperidin-3-yl)-4-amino-N-(2-chloro-4-(2-(dimethylamino)-2-oxoethyl)-5-fluorophenyl)-1H-pyrazolo[3,4-d]pyrimidine-3-carboxamide (Step 1) Synthesis of 2-(5-chloro-2-fluoro-4-nitrophenyl)acetic acid According to (Step 1) of Example 10, 275 mg of the title compound was obtained as a yellow solid by using 1-chloro-4,5-difluoro-2-nitrobenzene (500 mg) instead of 1,2-difluoro-4-methyl-5-nitrobenzene.

(Step 2) Synthesis of 2-(5-chloro-2-fluoro-4-nitrophenyl)-N,N-dimethylacetamide

According to (Step 1) of Example 4, 205 mg of the title compound was obtained as a yellow oil by using 2-(5-chloro-2-fluoro-4-nitrophenyl)acetic acid (234 mg) obtained in (Step 1) instead of 3-methyl-4-nitrophenylacetic acid.

(Step 3) Synthesis of 2-(4-amino-5-chloro-2-fluorophenyl)-N,N-dimethylacetamide

According to (Step 2) of Example 6, 150 mg of the title compound was obtained as a yellow solid by using 2-(5-chloro-2-fluoro-4-nitrophenyl)-N,N-dimethylacetamide (205 mg) obtained in (Step 2) instead of 2-(3-chloro-4-nitrophenyl)-N,N-dimethylacetamide.

(Step 4) Synthesis of Example Compound 18

According to (Step 3) of Example 4, (R)-1-(1-acryloylpiperidin-3-yl)-4-amino-1H-pyrazolo[3,4-d]pyrimidine-3-carboxylic acid (10 mg) and 2-(4-amino-5-chloro-2-fluorophenyl)-N,N-dimethylacetamide (20 mg) obtained in (Step 3) were dissolved by adding DMSO (0.2 mL) and DIPEA (20 μL). To the solution, HATU (50 mg) was then added to obtain 2.34 mg of the title compound as a white solid.

Example 19 Synthesis of (R)-1-(1-acryloylpiperidin-3-yl)-4-amino-N-(5-chloro-4-(2-(dimethylamino)-2-oxoethyl)-2-methylphenyl)-1H-pyrazolo[3,4-d]pyrimidine-3-carboxamide (Step 1) Synthesis of 1-chloro-2-fluoro-4-methyl-5-nitrobenzene 1-Chloro-2-fluoro-4-methylbenzene (1.00 g) was dissolved in TFA (10 mL). The solution was cooled to 0° C., and then, fuming nitric acid (5.0 mL) was added dropwise thereto. The mixture was stirred at 0° C. for 30 minutes, and then, the solution was added to an aqueous sodium bicarbonate solution and neutralized, followed by extraction with chloroform. The extract was dried over anhydrous sodium sulfate, and the solvent was distilled off under reduced pressure. The obtained residue was purified by silica gel chromatography (hexane/ethyl acetate) to obtain 1.31 g of the title compound as a white solid.

(Step 2) Synthesis of 2-(2-chloro-5-methyl-4-nitrophenyl)acetic acid

According to (Step 1) of Example 1, 440 mg of the title compound was obtained as a yellow solid by using 1-chloro- 2-fluoro-4-methyl-5-nitrobenzene (500 mg) obtained in (Step 1) instead of 1-bromo-2-fluoro-4-methyl-5-nitrobenzene.

(Step 3) Synthesis of 2-(2-chloro-5-methyl-4-nitrophenyl)-N,N-dimethylacetamide

According to (Step 2) of Example 1, 149 mg of the title compound was obtained as a pale yellow solid by using 2-(2-chloro-5-methyl-4-nitrophenyl)acetic acid (230 mg) obtained in (Step 2) instead of 2-(2-bromo-5-methyl-4-nitrophenyl)acetic acid.

(Step 4) Synthesis of 2-(4-amino-2-chloro-5-methylphenyl)-N,N-dimethylacetamide

According to (Step 3) of Example 1, 170 mg of the title compound was obtained as a white solid by using 2-(2-chloro-5-methyl-4-nitrophenyl)-N,N-dimethylacetamide (149 mg) obtained in (Step 3) instead of 2-(2-bromo-5-methyl-4-nitrophenyl)-N,N-dimethylacetamide.

(Step 5) Synthesis of Example Compound 19

According to (Step 4) of Example 1, (R)-1-(1-acryloylpiperidin-3-yl)-4-amino-1H-pyrazolo[3,4-d]pyrimidine-3-carboxylic acid (10 mg) and 2-(4-amino-2-chloro-5-methylphenyl)-N,N-dimethylacetamide (20 mg) obtained in (Step 4) were dissolved by adding DMSO (0.2 mL) and DIPEA (20 μL). To the solution, HATU (50 mg) was then added to obtain 3.39 mg of the title compound as a white solid.

Example 20 Synthesis of (R)-1-(1-acryloylpiperidin-3-yl)-4-amino-N-(2,5-dichloro-4-(2-(dimethylamino)-2-oxoethyl)phenyl)-1H-pyrazolo[3,4-d]pyrimidine-3-carboxamide (Step 1) Synthesis of 1,4-dichloro-2-fluoro-5-nitrobenzene According to (Step 1) of Example 19, 1,4-dichloro-2-fluorobenzene (1.00 g) was dissolved instead of 1-chloro-2-fluoro-4-methylbenzene in TFA (10 mL). To the solution, fuming nitric acid (5.0 mL) was added dropwise. The mixture was stirred at room temperature for 3 hours, and then, the solution was added to an aqueous sodium bicarbonate solution. The precipitated solid was collected by filtration and dried to obtain 1.30 g of the title compound as a white solid.

(Step 2) Synthesis of 2-(2,5-dichloro-4-nitrophenyl)acetic acid

According to (Step 1) of Example 1, 423 mg of the title compound was obtained as a yellow solid by using 1,4-dichloro-2-fluoro-5-nitrobenzene (500 mg) obtained in (Step 1) instead of 1-bromo-2-fluoro-4-methyl-5-nitrobenzene.

(Step 3) Synthesis of 2-(2,5-dichloro-4-nitrophenyl)-N,N-dimethylacetamide

According to (Step 2) of Example 1, 150 mg of the title compound was obtained as a pale yellow solid by using 2-(2,5-dichloro-4-nitrophenyl)acetic acid (250 mg) obtained in (Step 2) instead of 2-(2-bromo-5-methyl-4-nitrophenyl) acetic acid.

(Step 4) Synthesis of 2-(4-amino-2,5-dichlorophenyl)-N,N-dimethylacetamide

According to (Step 3) of Example 1, 160 mg of the title compound was obtained as a white solid by using 2-(2,5-dichloro-4-nitrophenyl)-N,N-dimethylacetamide (150 mg) obtained in (Step 3) instead of 2-(2-bromo-5-methyl-4-nitrophenyl)-N,N-dimethylacetamide.

(Step 5) Synthesis of Example Compound 20

According to (Step 4) of Example 1, (R)-1-(1-acryloylpiperidin-3-yl)-4-amino-1H-pyrazolo[3,4-d]pyrimidine-3-carboxylic acid (10 mg) and 2-(4-amino-2,5-dichlorophenyl)-N,N-dimethylacetamide (20 mg) obtained in (Step 4) were dissolved by adding DMSO (0.2 mL) and DIPEA (20 μL). To the solution, HATU (50 mg) was then added to obtain 0.89 mg of the title compound as a white solid.

Example 21 Synthesis of (R)-4-(1-(1-acryloylpiperidin-3-yl)-4-amino-1H-pyrazolo[3,4-d]pyrimidine-3-carboxamido)phenyldimethyl carbamate (Step 1) Synthesis of (R)-1-(1-acryloylpiperidin-3-yl)-4-amino-N-(4-hydroxyphenyl)-1H-pyrazolo[3,4-d]pyrimidine-3-carboxamide (R)-1-(1-Acryloylpiperidin-3-yl)-4-amino-1H-pyrazolo[3,4-d]pyrimidine-3-carboxylic acid (30 mg) synthesized in Reference Example 3 was dissolved by adding DMF (4.5 mL), 4-aminophenol (17 mg), and DIPEA (50 μL). To the solution, HATU (55 mg) was then added. The mixture was stirred at room temperature for 1 hour, and then, ethyl acetate and water were added thereto to separate an organic layer. The organic layer was dried over anhydrous sodium sulfate, and the solvent was distilled off under reduced pressure. The residue was purified by silica gel chromatography (chloroform/methanol) to obtain 25 mg of the title compound as a colorless oil.

(Step 2) Synthesis of Example Compound 21

To (R)-1-(1-acryloylpiperidin-3-yl)-4-amino-N-(4-hydroxyphenyl)-1H-pyrazolo[3,4-d]pyrimidine-3-carboxamide (10 mg) obtained in (Step 1), potassium carbonate (10 mg) and acetonitrile (250 μL) were added to prepare a suspension. Then, N,N-dimethylcarbamoyl chloride (8 mg) was added thereto. The mixture was stirred at 60° C. for 3 hours, and then, chloroform and water were added thereto to separate an organic layer. The organic layer was dried over anhydrous sodium sulfate, and the solvent was distilled off under reduced pressure. The residue was purified by reverse-phase preparative HPLC purification (water/acetonitrile (0.1% formic acid)) to obtain 2.62 mg of the title compound as a white solid.

Example 22 Synthesis of (R)-1-(1-acryloylpiperidin-3-yl)-4-amino-N-(2-cyclopropyl-4-(2-(dimethylamino)-2-oxoethyl)phenyl)-1H-pyrazolo[3,4-d]pyrimidine-3-carboxamide (Step 1) Synthesis of 2-cyclopropyl-4-fluoro-1-nitrobenzene 2-Bromo-4-fluoro-1-nitrobenzene (1.22 g), potassium phosphate (4.12 g), and cyclopropylboronic acid were suspended in toluene (15 mL). To the suspension, water (0.75 mL), palladium acetate (0.062 mg), and tricyclohexylphosphine (155 mg) were added, and the mixture was heated to reflux in a nitrogen atmosphere and stirred for 4 hours. The mixture was allowed to cool, and then, water was added thereto, followed by extraction with ethyl acetate. The obtained organic layer was washed with water and subsequently washed with saturated saline. The obtained organic layer was dried using anhydrous sodium sulfate, filtered, and concentrated, and then, the residue was purified by silica gel chromatography to obtain the title compound (895 mg) as a light brown oil.

(Step 2) Synthesis of 2-(3-cyclopropyl-4-nitrophenyl)acetic acid

The title compound (845 mg) was obtained as a light orange solid in the same way as in the approach of (Step 1) of Example 10 by using 2-cyclopropyl-4-fluoro-1-nitrobenzene (895 mg) instead of 1,2-difluoro-4-methyl-5-nitrobenzene as a starting material.

(Step 3) Synthesis of 2-(3-cyclopropyl-4-nitrophenyl)-N,N-dimethylacetamide

According to (step 1) of Example 4, the title compound (445 mg) was obtained by using 2-(3-cyclopropyl-4-nitrophenyl)acetic acid (895 mg) instead of 3-methyl-4-nitrophenylacetic acid.

(Step 4) Synthesis of 2-(4-amino-3-cyclopropylphenyl)-N,N-dimethylacetamide

According to (Step 2) of Example 6, the title compound (225 mg) was obtained as a light brown oil by using 2-(3-cyclopropyl-4-nitrophenyl)-N,N-dimethylacetamide (445 mg) instead of 2-(3-chloro-4-nitrophenyl)-N,N-dimethylacetamide.

(Step 5) Synthesis of Example Compound 22

According to (Step 4) of Example 1, (R)-1-(1-acryloylpiperidin-3-yl)-4-amino-1H-pyrazolo[3,4-d]pyrimidine-3-carboxylic acid (50 mg) obtained in Reference Example 3 and 2-(4-amino-3-cyclopropylphenyl)-N,N-dimethylacetamide (51 mg) obtained in (Step 4) were dissolved by adding DMF (1 mL) and DIPEA (0.055 mL). To the solution, HATU (90 mg) was then added to obtain 52 mg of the title compound as a colorless solid.

Example 23 Synthesis of (R)-1-(1-acryloylpiperidin-3-yl)-4-amino-N-(2-cyano-4-(2-(dimethylamino)-2-oxoethyl)phenyl)-1H-pyrazolo[3,4-d]pyrimidine-3-carboxamide (Step 1) Synthesis of 2-(4-amino-3-bromophenyl)-N,N-dimethylacetamide 2-(4-Aminophenyl)acetic acid (1.03 g) was suspended in THF (40 mL). To the suspension, N-bromosuccinimide (1.27 g) was then added at room temperature, and then, the mixture was stirred for 1 hour. The solution was concentrated. To the residue, a 2.0 M solution of dimethylamine in THF (17 mL) was added, and subsequently, HATU (3.89 g) was added at room temperature. The mixture was stirred at room temperature. Then, the solution was concentrated, and the residue was diluted with ethyl acetate. The ethyl acetate solution was washed with water, then washed with a 1 N aqueous sodium hydroxide solution, and subsequently washed with saturated saline. The obtained organic layer was dried over anhydrous sodium sulfate, filtered, and concentrated, and the residue was purified by silica gel chromatography (eluent:hexane-ethyl acetate) to obtain the title compound (1.07 g) as a pale yellow oil.

(Step 2) Synthesis of 2-(4-amino-3-cyanophenyl)-N,N-dimethylacetamide 2-(4-Amino-3-bromophenyl)-N,N-dimethylacetamide (1.07 g) obtained in (Step 1) was dissolved in DMF (10 mL). After purging with nitrogen, tetrakis(triphenylphosphine)palladium (481 mg) and zinc cyanide (977 mg) were added to the solution, and the mixture was stirred at 120° C. for 16 hours. The mixture was allowed to cool to room temperature and then diluted with ethyl acetate. A 28% aqueous ammonium solution was added thereto, and the mixture was stirred for 10 minutes. After extraction with ethyl acetate, the extract was washed with a 28% aqueous ammonium solution again, then washed with water, and washed with saturated saline. The obtained organic layer was dried over anhydrous sodium sulfate, filtered, and concentrated, and the residue was purified by silica gel chromatography (eluent:hexane-ethyl acetate) to obtain the title compound (360 mg) as a pale yellow solid.

(Step 3) Synthesis of Example Compound 23

According to (Step 4) of Example 1, (R)-1-(1-acryloylpiperidin-3-yl)-4-amino-1H-pyrazolo[3,4-d]pyrimidine-3-carboxylic acid (50 mg) obtained in Reference Example 3 and 2-(4-amino-3-cyanophenyl)-N,N-dimethylacetamide (48 mg) obtained in (Step 2) were dissolved by adding DMF (1 mL) and DIPEA (0.055 mL). To the solution, HATU (90 mg) was then added to obtain 12 mg of the title compound as a colorless solid.

Example 24 Synthesis of (R)-1-(1-acryloylpiperidin-3-yl)-4-amino-N-(5-cyano-4-(2-(dimethylamino)-2-oxoethyl)-2-methylphenyl)-1H-pyrazolo[3,4-d]pyrimidine-3-carboxamide (Step 1) Synthesis of 2-(2-cyano-5-methyl-4-nitrophenyl)-N,N-dimethylacetamide 2-(2-Bromo-5-methyl-4-nitrophenyl)-N,N-dimethylacetamide (500 mg) obtained in (Step 2) of Example 1 was dissolved in DMF (5 mL). After purging with nitrogen, tetrakis(triphenylphosphine)palladium (191 mg) and zinc cyanide (390 mg) were added to the solution, and the mixture was stirred at 120° C. for 16 hours. The mixture was allowed to cool to room temperature and then diluted with ethyl acetate. A 28% aqueous ammonium solution was added thereto, and the mixture was stirred for 10 minutes. After extraction with ethyl acetate, the extract was washed with a 28% aqueous ammonium solution again, then washed with water, and washed with saturated saline. The obtained organic layer was dried over anhydrous sodium sulfate, filtered, and concentrated, and the residue was purified by silica gel chromatography (eluent:hexane-ethyl acetate) to obtain the title compound (209 mg) as a pale yellow solid.

(Step 2) Synthesis of 2-(4-amino-2-cyano-5-methylphenyl)-N,N-dimethylacetamide

According to (Step 2) of Example 4, the title compound (143 mg) was obtained as a colorless solid by using 2-(2- cyano-5-methyl-4-nitrophenyl)-N,N-dimethylacetamide (200 mg) instead of N,N-dimethyl-2-(3-methyl-4-nitrophenyl)acetamide.

(Step 3) Synthesis of Example Compound 24

According to (Step 4) of Example 1, (R)-1-(1-acryloylpiperidin-3-yl)-4-amino-1H-pyrazolo[3,4-d]pyrimidine-3-carboxylic acid (50 mg) obtained in Reference Example 3 and 2-(4-amino-2-cyano-5-methylphenyl)-N,N-dimethylacetamide (51 mg) obtained in (Step 2) were dissolved by adding DMF (1 mL) and DIPEA (0.055 mL). To the solution, HATU (90 mg) was then added to obtain 57 mg of the title compound as an off-white solid.

Example 25 Synthesis of (R)-1-(1-acryloylpiperidin-3-yl)-4-amino-N-(4-(2-(dimethylamino)-2-oxoethyl)-2-fluorophenyl)-1H-pyrazolo[3,4-d]pyrimidine-3-carboxamide (Step 1) Synthesis of 2-(4-amino-3-fluorophenyl)-N,N-dimethylacetamide 2-(4-Amino-3-fluorophenyl)acetic acid (400 mg) was suspended in a 2.0 M solution of dimethylamine in THF (7 mL). To the suspension, WSC (0.58 g) was then added at room temperature, and the mixture was stirred at room temperature for 1 hour. A 2.0 M solution of dimethylamine in THF (7 mL) was added thereto, subsequently HATU (1.16 g) was added thereto, and the mixture was stirred for 30 minutes. After concentration of the solution, the residue was purified by silica gel chromatography (eluent:hexane-ethyl acetate) to obtain the title compound (300 mg) as a light brown oil.

(Step 2) Synthesis of Example Compound 25

According to (Step 4) of Example 1, (R)-1-(1-acryloylpiperidin-3-yl)-4-amino-1H-pyrazolo[3,4-d]pyrimidine-3-carboxylic acid (50 mg) obtained in Reference Example 3 and 2-(4-amino-3-fluorophenyl)-N,N-dimethylacetamide (46 mg) obtained in (Step 1) were dissolved by adding DMF (1 mL) and DIPEA (0.055 mL). To the solution, HATU (90 mg) was then added to obtain 8.1 mg of the title compound as a colorless solid.

Example 26 Synthesis of (R)-4-(1-(1-acryloylpiperidin-3-yl)-4-amino-1H-pyrazolo[3,4-d]pyrimidine-3-carboxamido)-3-methylphenyl dimethylcarbamate (Step 1) Synthesis of (R)-1-(1-acryloylpiperidin-3-yl)-4-amino-N-(4-hydroxy-2-methylphenyl)-1H-pyrazolo[3,4-d]pyrimidine-3-carboxamide (R)-1-(1-Acryloylpiperidin-3-yl)-4-amino-1H-pyrazolo[3,4-d]pyrimidine-3-carboxylic acid (30 mg) synthesized in Reference Example 3 was dissolved by adding DMF (4.5 mL), 4-amino-3-methylphenol (17 mg), and DIPEA (50 μL). To the solution, HATU (55 mg) was then added. The mixture was stirred at room temperature for 1 hour, and then, ethyl acetate and water were added thereto to separate an organic layer. The organic layer was dried over anhydrous sodium sulfate, and the solvent was distilled off under reduced pressure. The residue was purified by silica gel chromatography (chloroform/methanol) to obtain 25 mg of the title compound as a colorless oil.

(Step 2) Synthesis of Example Compound 26

To (R)-1-(1-acryloylpiperidin-3-yl)-4-amino-N-(4-hydroxy-2-methylphenyl)-1H-pyrazolo[3,4-d]pyrimidine-3-carboxamide (10 mg) obtained in (Step 1), potassium carbonate (10 mg) and acetonitrile (250 μL) were added to prepare a suspension. Then, N,N-dimethylcarbamoyl chloride (8 mg) was added thereto. The mixture was stirred at 60° C. for 3 hours, and then, chloroform and water were added thereto to separate an organic layer. The organic layer was dried over anhydrous sodium sulfate, and the solvent was distilled off under reduced pressure. The residue was purified by reverse-phase preparative HPLC purification (water/acetonitrile (0.1% formic acid)) to obtain 2.62 mg of the title compound as a white solid.

Example 27 Synthesis of (R)-4-(1-(1-acryloylpiperidin-3-yl)-4-amino-1H-pyrazolo[3,4-d]pyrimidine-3-carboxamido)-3-chlorophenyl dimethylcarbamate (Step 1) Synthesis of (R)-1-(1-acryloylpiperidin-3-yl)-4-amino-N-(2-chloro-4-hydroxyphenyl)-1H-pyrazolo[3,4-d]pyrimidine-3-carboxamide According to (Step 1) of Example 26, 41 mg of the title compound was obtained as a white solid by using (R)-1-(1-acryloylpiperidin-3-yl)-4-amino-1H-pyrazolo[3,4-d]pyrimidine-3-carboxylic acid (30 mg) and 4-amino-3-chlorophenol (25 mg).

(Step 2) Synthesis of Example Compound 27

According to (Step 2) of Example 26, 8.1 mg of the title compound was obtained as a white solid by using (R)-1-(1-acryloylpiperidin-3-yl)-4-amino-N-(2-chloro-4-hydroxyphenyl)-1H-pyrazolo[3,4-d]pyrimidine-3-carboxamide (10 mg) obtained in (Step 1) instead of (R)-1-(1-acryloylpiperidin-3-yl)-4-amino-N-(4-hydroxy-2-methylphenyl)-1H-pyrazolo[3,4-d]pyrimidine-3-carboxamide.

Example 28 Synthesis of (R)-1-(1-acryloylpiperidin-3-yl)-4-amino-N-(4-(2-(dimethylamino)-2-oxoethyl)phenyl)-1H-pyrazolo[3,4-d]pyrimidine-3-carboxamide (Step 1) Synthesis of N,N-dimethyl-2-(4-nitrophenyl)acetamide According to (Step 1) of Example 4, 60 mg of the title compound was obtained as a yellow oil by using 2-(4-nitrophenyl)acetic acid (50 mg) instead of 3-methyl-4-nitrophenylacetic acid.

(Step 2) Synthesis of 2-(4-aminophenyl)-N,N-dimethylacetamide

According to (Step 2) of Example 6, 50 mg of the title compound was obtained as a yellow oil by using N,N-dimethyl-2-(4-nitrophenyl)acetamide (60 mg) obtained in (Step 1) instead of 2-(3-chloro-4-nitrophenyl)-N,N-dimethylacetamide.

(Step 3) Synthesis of Example Compound 28

According to (Step 3) of Example 4, 5.22 mg of the title compound was obtained as a white solid by using (R)-1-(1-acryloylpiperidin-3-yl)-4-amino-1H-pyrazolo[3,4-d]pyrimidine-3-carboxylic acid (7.5 mg) and 2-(4-aminophenyl)-N,N-dimethylacetamide (7.5 mg) obtained in (Step 2).

Example 29 Synthesis of (R)-4-(1-(1-acryloylpiperi-
din-3-yl)-4-amino-1H-pyrazolo[3,4-d]pyrimidine-3-
carboxamido)-2-chlorophenyl dimethylcarbamate (Step 1) Synthesis of 2-chloro-4-nitrophenyl dimethylcarbamate To 2-chloro-4-nitrophenol (100 mg), potassium carbonate (160 mg) and acetonitrile (3.0 mL) were added, and N,N-dimethylcarbamoyl chloride (100 mg) was added to the suspension. The mixture was stirred at 60° C. for 2 hours, and then, ethyl acetate and water were added thereto to separate an organic layer. The organic layer was dried over anhydrous sodium sulfate, and the solvent was distilled off under reduced pressure. The residue was purified by silica gel chromatography (hexane/ethyl acetate) to obtain 120 mg of the title compound as a colorless oil.

(Step 2) Synthesis of 4-amino-2-chlorophenyl dimethylcarbamate

According to (Step 2) of Example 6, 95 mg of the title compound was obtained as a yellow oil by using 2-chloro-4-nitrophenyl dimethylcarbamate (120 mg) obtained in (Step 1) instead of 2-(3-chloro-4-nitrophenyl)-N,N-dimethylacetamide.

(Step 3) Synthesis of Example Compound 29

According to (Step 3) of Example 4, 4.27 mg of the title compound was obtained as a white solid by using (R)-1-(1-acryloylpiperidin-3-yl)-4-amino-1H-pyrazolo[3,4-d]pyrimidine-3-carboxylic acid (10 mg) and 4-amino-2-chlorophenyl dimethylcarbamate (10 mg) obtained in (Step 2).

Example 30 Synthesis of (R)-4-(1-(1-acryloylpiperi-
din-3-yl)-4-amino-1H-pyrazolo[3,4-d]pyrimidine-3-
carboxamido)-2-methylphenyl dimethylcarbamate (Step 1) Synthesis of Example Compound 30

(R)-1-(1-Acryloylpiperidin-3-yl)-4-amino-1H-pyrazolo[3,4-d]pyrimidine-3-carboxylic acid (10 mg) synthesized in Reference Example 3 was dissolved by adding DMF (0.2 mL), 4-amino-2-methylphenol (7 mg), and DIPEA (20 µL). To the solution, HATU (18 mg) was then added. The mixture was stirred at room temperature for 1 hour, and then, the solution was purified by silica gel chromatography (chloroform/methanol) to obtain 10 mg of a white solid compound. Next, potassium carbonate (10 mg) and acetonitrile (250 µL) were added to the obtained compound (10 mg) to prepare a suspension. Then, N,N-dimethylcarbamoyl chloride (12 mg) was added thereto. The mixture was stirred at 60° C. for 3 hours, and then, chloroform and water were added thereto to separate an organic layer. The organic layer was dried over anhydrous sodium sulfate, and the solvent was distilled off under reduced pressure. The residue was purified by reverse-phase preparative HPLC purification (water/acetonitrile (0.1% formic acid)) to obtain 3.27 mg of the title compound as a white solid.

Example 31 Synthesis of (R)-4-(1-(1-acryloylpiperi-
din-3-yl)-4-amino-1H-pyrazolo[3,4-d]pyrimidine-3-
carboxamido)-3-fluorophenyl dimethylcarbamate (Step 1) Synthesis of Example Compound 31

According to Example 30, 2.47 mg of the title compound was obtained as a white solid by using (R)-1-(1-acryloylpiperidin-3-yl)-4-amino-1H-pyrazolo[3,4-d]pyrimidine-3-carboxylic acid (10 mg) and 4-amino-3-fluorophenol (7 mg).

Example 32 Synthesis of (R)-4-(1-(1-acryloylpiperi-
din-3-yl)-4-amino-1H-pyrazolo[3,4-d]pyrimidine-3-
carboxamido)-2,3-dimethylphenyl dimethylcarbamate (Step 1) Synthesis of Example Compound 32

According to Example 30, 2.67 mg of the title compound was obtained as a white solid by using (R)-1-(1-acryloylpiperidin-3-yl)-4-amino-1H-pyrazolo[3,4-d]pyrimidine-3-carboxylic acid (10 mg) and 4-amino-2,3-dimethylphenol (7 mg).

Example 33 Synthesis of (R)-4-(1-(1-acryloylpiperi-
din-3-yl)-4-amino-1H-pyrazolo[3,4-d]pyrimidine-3-
carboxamido) naphthalen-1-yl dimethylcarbamate (Step 1) Synthesis of Example Compound 33

According to Example 30, 2.60 mg of the title compound was obtained as a white solid by using (R)-1-(1-acryloylpiperidin-3-yl)-4-amino-1H-pyrazolo[3,4-d]pyrimidine-3-carboxylic acid (10 mg) and 4-aminonaphthol (10 mg).

Example 34 Synthesis of (R)-4-(1-(1-acryloylpiperi-
din-3-yl)-4-amino-1H-pyrazolo[3,4-d]pyrimidine-3-
carboxamido)-2-fluorophenyl dimethylcarbamate (Step 1) Synthesis of Example Compound 34

According to Example 30, 1.92 mg of the title compound was obtained as a white solid by using (R)-1-(1-acryloylpiperidin-3-yl)-4-amino-1H-pyrazolo[3,4-d]pyrimidine-3-carboxylic acid (10 mg) and 4-amino-2-fluorophenol (7 mg).

Example 35 Synthesis of (R)-4-(1-(1-acryloylpiperi-
din-3-yl)-4-amino-1H-pyrazolo[3,4-d]pyrimidine-3-
carboxamido)-2,3-difluorophenyl dimethylcarbamate (Step 1) Synthesis of Example Compound 35

According to Example 30, 1.10 mg of the title compound was obtained as a white solid by using (R)-1-(1-acryloylpiperidin-3-yl)-4-amino-1H-pyrazolo[3,4-d]pyrimidine-3-carboxylic acid (10 mg) and 4-amino-2,3-difluorophenol (7 mg).

Example 36 Synthesis of (R)-4-(1-(1-acryloylpiperi-
din-3-yl)-4-amino-1H-pyrazolo[3,4-d]pyrimidine-3-
carboxamido)-3-methoxyphenyl dimethylcarbamate (Step 1) Synthesis of Example Compound 36

According to Example 30, 10.8 mg of the title compound was obtained as a white solid by using (R)-1-(1-acryloylpiperidin-3-yl)-4-amino-1H-pyrazolo[3,4-d]pyrimidine-3-carboxylic acid (25 mg) and 4-amino-3-methoxyphenol (17 mg).

Example 37 Synthesis of (R)-8-(1-(1-acryloylpiperidin-3-yl)-4-amino-1H-pyrazolo[3,4-d]pyrimidine-3-carboxamido)quinolin-5-yl dimethylcarbamate (Step 1) Synthesis of 8-nitroquinolin-5-yl dimethylcarbamate To 8-nitroquinolin-5-ol (100 mg), potassium carbonate (220 mg) and acetonitrile (2.6 mL) were added, and N,N-dimethylcarbamoyl chloride (113 mg) was added to the suspension. The mixture was stirred at 60° C. for 2 hours, and then, ethyl acetate and water were added thereto to separate an organic layer. The organic layer was dried over anhydrous sodium sulfate, and the solvent was distilled off under reduced pressure. The residue was purified by silica gel chromatography (hexane/ethyl acetate) to obtain 110 mg of the title compound as a yellow solid.

(Step 2) Synthesis of 8-aminoquinolin-5-yl dimethylcarbamate

According to (Step 2) of Example 6, 90 mg of the title compound was obtained as a yellow oil by using 8-nitroquinolin-5-yl dimethylcarbamate (110 mg) obtained in (Step 1) instead of 2-(3-chloro-4-nitrophenyl)-N,N-dimethylacetamide.

(Step 3) Synthesis of Example Compound 37

According to (Step 3) of Example 4, 5.37 mg of the title compound was obtained as a white solid by using (R)-1-(1-acryloylpiperidin-3-yl)-4-amino-1H-pyrazolo[3,4-d]pyrimidine-3-carboxylic acid (10 mg) and 8-aminoquinolin-5-yl dimethylcarbamate (10 mg) obtained in (Step 2).

Example 38 Synthesis of (R)-4-(1-(1-acryloylpiperidin-3-yl)-4-amino-1H-pyrazolo[3,4-d]pyrimidine-3-carboxamido)-2,5-dimethylphenyl dimethylcarbamate (Step 1) Synthesis of Example Compound 38

According to Example 30, 8.01 mg of the title compound was obtained as a white solid by using (R)-1-(1-acryloylpiperidin-3-yl)-4-amino-1H-pyrazolo[3,4-d]pyrimidine-3-carboxylic acid (10 mg) and 4-amino-2,5-dimethylphenol (10 mg).

Example 39 Synthesis of (R)-1-(1-acryloylpiperidin-3-yl)-4-amino-N-(4-(2-(dimethylamino)-2-oxoethyl)-2,5-dimethylphenyl)-1H-pyrazolo[3,4-d]pyrimidine-3-carboxamide (Step 1) Synthesis of 2-(2,5-dimethyl-4-nitrophenyl)-N,N-dimethylacetamide According to (Step 1) of Example 4, 110 mg of the title compound was obtained as a yellow oil by using 2-(2,5-dimethyl-4-nitrophenyl)acetic acid (100 mg) instead of 3-methyl-4-nitrophenylacetic acid.

(Step 2) Synthesis of 2-(4-amino-2,5-dimethylphenyl)-N,N-dimethylacetamide

According to (Step 2) of Example 6, 90 mg of the title compound was obtained as a yellow oil by using 2-(2,5-dimethyl-4-nitrophenyl)-N,N-dimethylacetamide (110 mg) obtained in (Step 1) instead of 2-(3-chloro-4-nitrophenyl)-N,N-dimethylacetamide.

(Step 3) Synthesis of Example Compound 39

According to (Step 3) of Example 4, 4.50 mg of the title compound was obtained as a white solid by using (R)-1-(1-acryloylpiperidin-3-yl)-4-amino-1H-pyrazolo[3,4-d]pyrimidine-3-carboxylic acid (10 mg) and 2-(4-amino-2,5-dimethylphenyl)-N,N-dimethylacetamide (10 mg) obtained in (Step 2).

Example 40 Synthesis of (R)-1-(1-acryloylpiperidin-3-yl)-4-amino-N-(4-(2-(dimethylamino)-2-oxoethyl)-3-methoxyphenyl)-1H-pyrazolo[3,4-d]pyrimidine-3-carboxamide (Step 1) Synthesis of 2-(2-methoxy-4-nitrophenyl)-N,N-dimethylacetamide According to the synthesis method described in European Journal of Medicinal Chemistry, 46 (1), 285-296; 2010, 250 mg of the title compound was obtained as a yellow oil by using 2-methoxy-4-nitrobenzaldehyde (300 mg) instead of 4-nitrobenzaldehyde.

(Step 2) Synthesis of 2-(4-amino-2-methoxyphenyl)-N,N-dimethylacetamide

According to (Step 2) of Example 6, 185 mg of the title compound was obtained as a yellow oil by using 2-(2-methoxy-4-nitrophenyl)-N,N-dimethylacetamide (250 mg) obtained in (Step 1) instead of 2-(3-chloro-4-nitrophenyl)-N,N-dimethylacetamide.

(Step 3) Synthesis of Example Compound 40

According to (Step 3) of Example 4, 8.22 mg of the title compound was obtained as a white solid by using (R)-1-(1-acryloylpiperidin-3-yl)-4-amino-1H-pyrazolo[3,4-d]pyrimidine-3-carboxylic acid (10 mg) and 2-(4-amino-2-methoxyphenyl)-N,N-dimethylacetamide (10 mg) obtained in (Step 2).

Example 41 Synthesis of (R)-1-(1-acryloylpiperidin-3-yl)-4-amino-N-(4-(2-(dimethylamino)-2-oxoethyl) quinolin-8-yl)-1H-pyrazolo[3,4-d]pyrimidine-3-carboxamide (Step 1) Synthesis of N,N-dimethyl-2-(8-nitroquinolin-5-yl)acetamide According to (Step 1) of Example 5, 150 mg of the title compound was obtained as a yellow solid by using 2-(quinolin-5-yl)acetic acid (220 mg) instead of 1-naphthylacetic acid.

(Step 2) Synthesis of 2-(8-aminoquinolin-5-yl)-N,N-dimethylacetamide

According to (Step 2) of Example 6, 110 mg of the title compound was obtained as a yellow oil by using N,N-dimethyl-2-(8-nitroquinolin-5-yl)acetamide (150 mg) obtained in (Step 1) instead of 2-(3-chloro-4-nitrophenyl)-N,N-dimethylacetamide.

(Step 3) Synthesis of Example Compound 41

According to (Step 3) of Example 4, 12.8 mg of the title compound was obtained as a white solid by using (R)-1-(1-acryloylpiperidin-3-yl)-4-amino-1H-pyrazolo[3,4-d]pyrimidine-3-carboxylic acid (10 mg) and 2-(8-aminoquinolin-5-yl)-N,N-dimethylacetamide (10 mg) obtained in (Step 2).

Example 42 Synthesis of (R)-1-(1-acryloylpiperidin-3-yl)-4-amino-N-(4-(2-(dimethylamino)-2-oxoethyl)-3-fluorophenyl)-1H-pyrazolo[3,4-d]pyrimidine-3-carboxamide (Step 1) Synthesis of 2-(2-fluoro-4-nitrophenyl)-N,N-dimethylacetamide According to the synthesis method described in European Journal of Medicinal Chemistry, 46 (1), 285-296; 2010, 420 mg of the title compound was obtained as a yellow oil by using 2-fluoro-4-nitrobenzaldehyde (550 mg) instead of 4-nitrobenzaldehyde.

(Step 2) Synthesis of 2-(4-amino-2-fluorophenyl)-N,N-dimethylacetamide

According to (Step 2) of Example 6, 320 mg of the title compound was obtained as a yellow oil by using 2-(2-fluoro-4-nitrophenyl)-N,N-dimethylacetamide (420 mg) obtained in (Step 1) instead of 2-(3-chloro-4-nitrophenyl)-N,N-dimethylacetamide.

(Step 3) Synthesis of Example Compound 42

According to (Step 3) of Example 4, 8.3 mg of the title compound was obtained as a white solid by using (R)-1-(1-acryloylpiperidin-3-yl)-4-amino-1H-pyrazolo[3,4-d]pyrimidine-3-carboxylic acid (10 mg) and 2-(4-amino-2-fluorophenyl)-N,N-dimethylacetamide (10 mg) obtained in (Step 2).

Example 43 Synthesis of (R)-4-(1-(1-acryloylpiperidin-3-yl)-4-amino-1H-pyrazolo[3,4-d]pyrimidine-3-carboxamido)-2,6-difluorophenyl dimethylcarbamate (Step 1) Synthesis of 2,6-difluoro-4-nitrophenyl dimethylcarbamate According to (Step 1) of Example 29, 260 mg of the title compound was obtained as a yellow oil by using 2,6-difluoro-4-nitrophenol (200 mg) instead of 2-chloro-4-nitrophenol.

(Step 2) Synthesis of 4-amino-2,6-difluorophenyl dimethylcarbamate

According to (Step 2) of Example 6, 220 mg of the title compound was obtained as a yellow oil by using 2,6-difluoro-4-nitrophenyl dimethylcarbamate (260 mg) obtained in (Step 1) instead of 2-(3-chloro-4-nitrophenyl)-N,N-dimethylacetamide.

(Step 3) Synthesis of Example Compound 43

According to (Step 3) of Example 4, 7.47 mg of the title compound was obtained as a brown solid by using (R)-1-(1-acryloylpiperidin-3-yl)-4-amino-1H-pyrazolo[3,4-d]pyrimidine-3-carboxylic acid (10 mg) and 4-amino-2,6-difluorophenyl dimethylcarbamate (10 mg) obtained in (Step 2).

Example 44 Synthesis of (R)-4-(1-(1-acryloylpiperidin-3-yl)-4-amino-1H-pyrazolo[3,4-d]pyrimidine-3-carboxamido)-3,5-dimethylphenyl dimethylcarbamate (Step 1) Synthesis of (R)-1-(1-acryloylpiperidin-3-yl)-4-amino-N-(4-hydroxy-2,6-dimethylphenyl)-1H-pyrazolo[3,4-d]pyrimidine-3-carboxamide According to (Step 1) of Example 26, 30 mg of the title compound was obtained as a white solid by using (R)-1-(1-acryloylpiperidin-3-yl)-4-amino-1H-pyrazolo[3,4-d]pyrimidine-3-carboxylic acid (30 mg) and 4-amino-3,5-dimethylphenol (25 mg).

(Step 2) Synthesis of Example Compound 44

According to (Step 2) of Example 26, 12 mg of the title compound was obtained as a white solid by using (R)-1-(1-acryloylpiperidin-3-yl)-4-amino-N-(4-hydroxy-2,6-dimethylphenyl)-1H-pyrazolo[3,4-d]pyrimidine-3-carboxamide (10 mg) obtained in (Step 1) instead of (R)-1-(1-acryloylpiperidin-3-yl)-4-amino-N-(4-hydroxy-2-methylphenyl)-1H-pyrazolo[3,4-d]pyrimidine-3-carboxamide.

Example 45 Synthesis of (R)-4-(1-(1-acryloylpiperidin-3-yl)-4-amino-1H-pyrazolo[3,4-d]pyrimidine-3-carboxamido)-2,6-dichlorophenyl dimethylcarbamate (Step 1) Synthesis of (R)-1-(1-acryloylpiperidin-3-yl)-4-amino-N-(3,5-dichloro-4-hydroxyphenyl)-1H-pyrazolo[3,4-d]pyrimidine-3-carboxamide According to (Step 1) of Example 26, 20 mg of the title compound was obtained as a white solid by using (R)-1-(1-acryloylpiperidin-3-yl)-4-amino-1H-pyrazolo[3,4-d]pyrimidine-3-carboxylic acid (30 mg) and 4-amino-2,6-dichlorophenol (25 mg).

(Step 2) Synthesis of Example Compound 45

According to (Step 2) of Example 26, 7.5 mg of the title compound was obtained as a white solid by using (R)-1-(1-acryloylpiperidin-3-yl)-4-amino-N-(3,5-dichloro-4-hydroxyphenyl)-1H-pyrazolo[3,4-d]pyrimidine-3-carboxamide (10 mg) obtained in (step 1) instead of (R)-1-(1-acryloylpiperidin-3-yl)-4-amino-N-(4-hydroxy-2-methylphenyl)-1H-pyrazolo[3,4-d]pyrimidine-3-carboxamide.

Example 46 Synthesis of (R)-4-(1-(1-acryloylpiperidin-3-yl)-4-amino-1H-pyrazolo[3,4-d]pyrimidine-3-carboxamido)-2,6-dimethylphenyl dimethylcarbamate (Step 1) Synthesis of 2,6-dimethyl-4-nitrophenyl dimethylcarbamate According to (Step 1) of Example 29, 260 mg of the title compound was obtained as a yellow oil by using 2,6-dimethyl-4-nitrophenol (200 mg) instead of 2-chloro-4-nitrophenol.

(Step 2) Synthesis of 4-amino-2,6-dimethylphenyl dimethylcarbamate

According to (Step 2) of Example 6, 210 mg of the title compound was obtained as a yellow oil by using 2,6-dimethyl-4-nitrophenyl dimethylcarbamate (260 mg) obtained in (Step 1) instead of 2-(3-chloro-4-nitrophenyl)-N,N-dimethylacetamide.

(Step 3) Synthesis of Example Compound 46

According to (Step 3) of Example 4, 13.2 mg of the title compound was obtained as a white solid by using (R)-1-(1-acryloylpiperidin-3-yl)-4-amino-1H-pyrazolo[3,4-d]pyrimidine-3-carboxylic acid (10 mg) and 4-amino-2,6-dimethylphenyl dimethylcarbamate (10 mg) obtained in (Step 2).

Example 47 Synthesis of (R)-1-(1-acryloylpiperidin-3-yl)-4-amino-N-(2-(dimethylamino)-4-(2-(dimethylamino)-2-oxoethyl)phenyl)-1H-pyrazolo[3,4-d]pyrimidine-3-carboxamide

(Step 1) Synthesis of 2-(3-fluoro-4-nitrophenyl)-N,N-dimethyl-2-acetamide

According to the synthesis method described in European Journal of Medicinal Chemistry, 46 (1), 285-296; 2010, 300 mg of the title compound was obtained as a yellow oil by using 3-fluoro-4-nitrobenzaldehyde (500 mg) instead of 4-nitrobenzaldehyde.

(Step 2) Synthesis of 2-(4-amino-3-fluorophenyl)-N,N-dimethylacetamide

According to (Step 2) of Example 6, 240 mg of the title compound was obtained as a yellow oil by using 2-(3-fluoro-4-nitrophenyl)-N,N-dimethyl-2-acetamide (300 mg) obtained in (Step 1) instead of 2-(3-chloro-4-nitrophenyl)-N,N-dimethylacetamide.

(Step 3) Synthesis of Example Compound 47

According to (Step 3) of Example 4, 10.2 mg of the title compound was obtained as a white solid by using (R)-1-(1-acryloylpiperidin-3-yl)-4-amino-1H-pyrazolo[3,4-d]pyrimidine-3-carboxylic acid (10 mg) and 2-(4-amino-3-fluorophenyl)-N,N-dimethylacetamide (10 mg) obtained in (Step 2).

Example 48 Synthesis of (R)-1-(1-acryloylpiperidin-3-yl)-4-amino-N-(4-(2-(dimethylamino)-2-oxoethyl)-2-vinylphenyl)-1H-pyrazolo[3,4-d]pyrimidine-3-carboxamide

(Step 1) Synthesis of N,N-dimethyl-2-(4-nitro-3-vinylphenyl)acetamide

To 2-(3-bromo-4-nitrophenyl)-N,N-dimethylacetamide (330 mg) obtained in (Step 1) of Example 17, potassium vinyltrifluoroborate (330 mg), a Pd-dppf complex (93 mg), DME (5.7 mL), and a 2 M aqueous sodium carbonate solution (2.9 mL) were added. The mixture was stirred at 80° C. for 12 hours, and then, ethyl acetate and water were added thereto to separate an organic layer. The organic layer was dried over anhydrous sodium sulfate, and the solvent was distilled off under reduced pressure. The residue was purified by silica gel chromatography (hexane/ethyl acetate) to obtain 270 mg of the title compound as a yellow solid.

(Step 2) Synthesis of 2-(4-amino-3-vinylphenyl)-N,N-dimethylacetamide

According to (Step 2) of Example 6, 80 mg of the title compound was obtained as a yellow oil by using N,N-dimethyl-2-(4-nitro-3-vinylphenyl)acetamide (100 mg) obtained in (Step 1) instead of 2-(3-chloro-4-nitrophenyl)-N,N-dimethylacetamide.

(Step 3) Synthesis of Example Compound 48

According to (Step 3) of Example 4, 8.16 mg of the title compound was obtained as a green solid by using (R)-1-(1-acryloylpiperidin-3-yl)-4-amino-1H-pyrazolo[3,4-d]pyrimidine-3-carboxylic acid (10 mg) and 2-(4-amino-3-vinylphenyl)-N,N-dimethylacetamide (10 mg) obtained in (Step 2).

Example 49 Synthesis of (R)-1-(1-acryloylpiperidin-3-yl)-4-amino-N-(4-(2-(dimethylamino)-2-oxoethyl)-2-ethylphenyl)-1H-pyrazolo[3,4-d]pyrimidine-3-carboxamide

(Step 1) Synthesis of 2-(4-amino-3-ethylphenyl)-N,N-dimethylacetamide

According to (Step 2) of Example 4, 80 mg of the title compound was obtained as a yellow oil by using N,N-dimethyl-2-(4-nitro-3-vinylphenyl)acetamide (100 mg) obtained in (Step 1) of Example 48 instead of 2-(3-methyl-4-nitrophenyl)-N,N-dimethylacetamide.

(Step 2) Synthesis of Example Compound 49

According to (Step 3) of Example 4, 11.0 mg of the title compound was obtained as a yellow solid by using (R)-1-(1-acryloylpiperidin-3-yl)-4-amino-1H-pyrazolo[3,4-d]pyrimidine-3-carboxylic acid (10 mg) and 2-(4-amino-3-ethylphenyl)-N,N-dimethylacetamide (10 mg) obtained in (Step 1).

Example 50 Synthesis of (R)-1-(1-acryloylpiperidin-3-yl)-4-amino-N-(2-chloro-4-(2-(dimethylamino)-2-oxoethyl)-3-fluorophenyl)-1H-pyrazolo[3,4-d]pyrimidine-3-carboxamide

(Step 1) Synthesis of 2-(3-chloro-2-fluoro-4-nitrophenyl)acetic acid

To diethyl malonate (621 mg), NMP (5.0 mL), sodium hydride (248 mg), and 2-chloro-3,4-difluoro-1-nitrobenzene (500 mg) were added in this order at room temperature. The solution was heated to 100° C., stirred for 10 minutes, and then cooled to room temperature, and ethyl acetate and a saturated aqueous solution of ammonium chloride were added thereto to separate an organic layer. The organic layer was washed with water and saturated saline and then dried over anhydrous sodium sulfate, and the solvent was distilled off under reduced pressure. The residue was purified by silica gel chromatography (hexane/ethyl acetate) to obtain 1.00 g of a yellow oil. Next, methanol (5.0 mL) and a 5 M aqueous sodium hydroxide solution (2.5 mL) were added to the obtained oil, and the mixture was heated to 70° C. and stirred for 1.5 hours. the solution was cooled to room temperature, the solvent was distilled off under reduced pressure, and a 5 M aqueous hydrochloric acid solution was added to the residue. The precipitated solid was collected by filtration and dried to obtain 366 mg of the title compound as a yellow solid.

(Step 2) Synthesis of 2-(3-chloro-2-fluoro-4-nitrophenyl)-N,N-dimethylacetamide 2-(3-Chloro-2-fluoro-4-nitrophenyl)acetic acid (366 mg) obtained in (Step 1) was dissolved by adding DMF (7.85 mL), DIPEA (3.14 mL), and a 2.0 M solution of dimethylamine in THF (3.14 mL). To the solution, HATU (895 mg) was then added. The mixture was stirred at room temperature for 1 hour, and then, ethyl acetate and water were added thereto to separate an organic layer. The organic layer was washed with water and saturated saline and then dried over anhydrous sodium sulfate, and the solvent was distilled off under reduced pressure. The residue was purified by silica gel chromatography (hexane/ethyl acetate) to obtain 366 mg of the title compound as a yellow solid.

(Step 3) Synthesis of 2-(4-amino-3-chloro-2-fluorophenyl)-N,N-dimethylacetamide

To 2-(3-chloro-2-fluoro-4-nitrophenyl)-N,N-dimethylacetamide (150 mg) obtained in (Step 2), THF (1.5 mL) and water (1.5 mL) were added, and then, ammonium chloride (150 mg) and iron powder (150 mg) were added. The solution was heated to 70° C., stirred for 2 hours, then cooled to room temperature, and filtered through celite to remove iron. The solvent in the filtrate was distilled off under reduced pressure, and the obtained residue was purified by silica gel chromatography (ethyl acetate/methanol) to obtain 120 mg of the title compound as a yellow solid.

(Step 4) Synthesis of Example Compound 50

(R)-1-(1-Acryloylpiperidin-3-yl)-4-amino-1H-pyrazolo[3,4-d]pyrimidine-3-carboxylic acid (10 mg) obtained in Reference Example 3 and 2-(4-amino-3-chloro-2-fluorophenyl)-N,N-dimethylacetamide (30 mg) obtained in (Step 3) were dissolved by adding DMSO (0.2 mL) and DIPEA (10 μL). To the solution, HATU (50 mg) was then added. The mixture was stirred at room temperature for 1 hour. Then, DMSO (1 mL) was added thereto, and the mixture was purified by reverse-phase preparative HPLC purification (water/acetonitrile (0.1% formic acid)) to obtain 6.7 mg of the title compound as a white solid.

Example 51 Synthesis of (R)-1-(1-acryloylpiperidin-3-yl)-4-amino-N-(4-(2-(dimethylamino)-2-oxoethyl)-2-(furan-2-yl)phenyl)-1H-pyrazolo[3,4-d]pyrimidine-3-carboxamide (Step 1) Synthesis of 2-(3-(furan-2-yl)-4-nitrophenyl)N,N-dimethyl-acetamide To 2-(3-bromo-4-nitrophenyl)-N,N-dimethylacetamide (50 mg) obtained in (Step 1) of Example 17, 2-furylboronic acid (30 mg), a Pd-dppf complex (14 mg), DME (0.9 mL), and a 2 M aqueous sodium carbonate solution (0.45 mL) were added. The mixture was stirred at 80° C. for 12 hours, and then, ethyl acetate and water were added thereto to separate an organic layer. The organic layer was dried over anhydrous sodium sulfate, and the solvent was distilled off under reduced pressure. The residue was purified by silica gel chromatography (hexane/ethyl acetate) to obtain 45 mg of the title compound as a yellow solid.

(Step 2) Synthesis of 2-(4-amino-3-(furan-2-yl)phenyl)-N,N-dimethylacetamide

According to (Step 2) of Example 6, 30 mg of the title compound was obtained as a yellow oil by using 2-(3-(furan-2-yl)-4-nitrophenyl)-N,N-dimethylacetamide (45 mg) obtained in (Step 1) instead of 2-(3-chloro-4-nitrophenyl)-N,N-dimethylacetamide.

(Step 3) Synthesis of Example Compound 51

According to (Step 3) of Example 4, 8.09 mg of the title compound was obtained as a brown solid by using (R)-1-(1-acryloylpiperidin-3-yl)-4-amino-1H-pyrazolo[3,4-d]pyrimidine-3-carboxylic acid (10 mg) and 2-(4-amino-3-(furan-2-yl)phenyl)-N,N-dimethylacetamide (10 mg) obtained in (Step 2).

Example 52 Synthesis of (R)-1-(1-acryloylpiperidin-3-yl)-4-amino-N-(4-(2-(dimethylamino)-2-oxoethyl)-2-(furan-3-yl)phenyl)-1H-pyrazolo[3,4-d]pyrimidine-3-carboxamide (Step 1) Synthesis of 2-(3-(furan-3-yl)-4-nitrophenyl)-N,N-dimethylacetamide According to (Step 1) of Example 51, 45 mg of the title compound was obtained as a yellow oil by using 3-furylboronic acid (30 mg) instead of 2-furylboronic acid.

(Step 2) Synthesis of 2-(4-amino-3-(furan-3-yl)phenyl)-N,N-dimethylacetamide

According to (Step 2) of Example 6, 30 mg of the title compound was obtained as a yellow oil by using 2-(3-(furan-3-yl)-4-nitrophenyl)-N,N-dimethylacetamide (45 mg) obtained in (Step 1) instead of 2-(3-chloro-4-nitrophenyl)-N,N-dimethylacetamide.

(Step 3) Synthesis of Example Compound 52

According to (Step 3) of Example 4, 4.23 mg of the title compound was obtained as a white solid by using (R)-1-(1-acryloylpiperidin-3-yl)-4-amino-1H-pyrazolo[3,4-d]pyrimidine-3-carboxylic acid (10 mg) and 2-(4-amino-3-(furan-3-yl)phenyl)-N,N-dimethylacetamide (10 mg) obtained in (Step 2).

Example 53 Synthesis of (R)-1-(1-acryloylpiperidin-3-yl)-4-amino-N-(7-(2-(dimethylamino)-2-oxoethyl)benzo[d][1,3]dioxol-4-yl)-1H-pyrazolo[3,4-d]pyrimidine-3-carboxamide (Step 1) Synthesis of N,N-dimethyl-2-(7-nitrobenzo[d][1,3]dioxol-4-yl)acetamide To 7-nitrobenzo[d][1,3]dioxole-4-carbaldehyde (180 mg), dichloromethane (4.6 mL), carbon tetrabromide (1.06 g), and triphenylphosphine (1.55 g) were added, and the mixture was stirred at room temperature. Then, the solvent was removed with an evaporator. The residue was purified by silica gel chromatography (hexane/ethyl acetate) to obtain a yellow oil. Next, a 50% aqueous dimethylamine solution (5.0 mL) was added to the obtained oil, and the mixture was heated to 50° C. and stirred overnight. After the solution was cooled to room temperature, ethyl acetate and a saturated aqueous solution of ammonium chloride were added thereto to separate an organic layer. The organic layer was washed with water and saturated saline and then dried over anhydrous sodium sulfate, and the solvent was distilled off under reduced pressure. The residue was purified by silica gel chromatography (hexane/ethyl acetate) to obtain 120 mg of the title compound as a yellow oil.

(Step 2) Synthesis of 2-(7-aminobenzo[d][1,3]dioxol-4-yl)-N,N-dimethylacetamide

According to (Step 3) of Example 1, 100 mg of the title compound was obtained as a yellow oil by using N,N-dimethyl-2-(7-nitrobenzo[d][1,3]dioxol-4-yl) acetamide (120 mg) obtained in (Step 1) instead of 2-(2-bromo-5-methyl-4-nitrophenyl)-N,N-dimethylacetamide.

(Step 3) Synthesis of Example Compound 53

According to (Step 4) of Example 1, (R)-1-(1-acryloylpiperidin-3-yl)-4-amino-1H-pyrazolo[3,4-d]pyrimidine-3-carboxylic acid (10 mg) and 2-(7-aminobenzo[d][1,3]dioxol-4-yl)-N,N-dimethylacetamide (20 mg) obtained in (Step 2) were dissolved by adding DMSO (0.2 mL) and DIPEA (20 μL). To the solution, HATU (50 mg) was then added to obtain 6.38 mg of the title compound as a white solid.

Example 54 Synthesis of (R)-1-(1-acryloylpyrrolidin-3-yl)-4-amino-N-(2-chloro-4-(2-(dimethylamino)-2-oxoethyl)phenyl)-1H-pyrazolo[3,4-d]pyrimidine-3-carboxamide (Step 1) Synthesis of Example Compound 54

(R)-1-(1-Acryloylpyrrolidin-3-yl)-1H-pyrazolo[3,4-d]pyrimidine-3-carboxylic acid (10 mg) synthesized in Reference Example 5 was dissolved by adding 2-(4-amino-3-chlorophenyl)-N,N-dimethylacetamide (10 mg) obtained in (Step 2) of Example 6, DMF (0.2 mL), and DIPEA (20 μL). To the solution, HATU (18 mg) was then added. The mixture was stirred at room temperature for 1 hour. Then, DMSO (1 mL) was added thereto, and the mixture was purified by reverse-phase preparative HPLC purification (water/acetonitrile (0.1% formic acid)) to obtain 2.8 mg of the title compound as a white solid.

Example 55 Synthesis of (R)-1-(1-acryloylpyrrolidin-3-yl)-4-amino-N-(3-chloro-4-(2-(dimethylamino)-2-oxoethyl)-2-methoxyphenyl)-1H-pyrazolo[3,4-d]pyrimidine-3-carboxamide (Step 1) Synthesis of Example Compound 55

According to (Step 1) of Example 54, 3.33 mg of the title compound was obtained as a white solid by using (R)-1-(1-acryloylpyrrolidin-3-yl)-1H-pyrazolo[3,4-d]pyrimidine-3-carboxylic acid (5 mg) and 2-(4-amino-2-chloro-3-methoxyphenyl)-N,N-dimethylacetamide (5 mg) synthesized in (Step 3) of Example 11.

Example 56 Synthesis of (R)-1-(1-acryloylpyrrolidin-3-yl)-4-amino-N-(4-(2-(dimethylamino)-2-oxoethyl)-3-fluoro-2-methylphenyl)-1H-pyrazolo[3,4-d]pyrimidine-3-carboxamide (Step 1) Synthesis of Example Compound 56

According to (Step 1) of Example 54, 2.19 mg of the title compound was obtained as a white solid by using (R)-1-(1-acryloylpyrrolidin-3-yl)-1H-pyrazolo[3,4-d]pyrimidine-3-carboxylic acid (5 mg) and 2-(4-amino-2-fluoro-3-methylphenyl)-N,N-dimethylacetamide (5 mg) synthesized in (Step 3) of Example 12.

Example 57 Synthesis of (R)-1-(1-acryloylpyrrolidin-3-yl)-4-amino-N-(4-(2-(dimethylamino)-2-oxoethyl)-3-fluoro-2-methoxyphenyl)-1H-pyrazolo[3,4-d]pyrimidine-3-carboxamide (Step 1) Synthesis of Example Compound 57

According to (Step 1) of Example 54, 4.25 mg of the title compound was obtained as a brown solid by using (R)-1-(1-acryloylpyrrolidin-3-yl)-1H-pyrazolo[3,4-d]pyrimidine-3-carboxylic acid (5 mg) and 2-(4-amino-2-fluoro-3-methoxyphenyl)-N,N-dimethylacetamide (5 mg) synthesized in (Step 3) of Example 14.

Example 58 Synthesis of (R)-4-(1-(1-acryloylpyrrolidin-3-yl)-4-amino-1H-pyrazolo[3,4-d]pyrimidine-3-carboxamido) naphthalen-1-yl dimethylcarbamate (Step 1) Synthesis of 4-nitronaphthalen-1-yl dimethylcarbamate According to (Step 1) of Example 29, the title compound was obtained as a yellow solid by using 4-nitronaphthol instead of 2-chloro-4-nitrophenol.

(Step 2) Synthesis of 4-aminonaphthalen-1-yl dimethylcarbamate

According to (Step 2) of Example 6, the title compound was obtained as a yellow oil by using 4-nitronaphthalen-1-yl dimethylcarbamate obtained in (Step 1) instead of 2-(3-chloro-4-nitrophenyl)-N,N-dimethylacetamide.

(Step 3) Synthesis of Example Compound 58

According to (Step 1) of Example 54, 3.59 mg of the title compound was obtained as a white solid by using (R)-1-(1-acryloylpyrrolidin-3-yl)-1H-pyrazolo[3,4-d]pyrimidine-3-carboxylic acid (7 mg) and 4-aminonaphthalen-1-yl dimethylcarbamate (7 mg) synthesized in (Step 2) of Example 58.

Example 59 Synthesis of (R)-1-(1-acryloylpyrrolidin-3-yl)-4-amino-N-(4-(2-(dimethylamino)-2-oxoethyl)-2,3-dimethylphenyl)-1H-pyrazolo[3,4-d]pyrimidine-3-carboxamide (Step 1) Synthesis of Example Compound 59

According to (Step 1) of Example 54, 1.23 mg of the title compound was obtained as a white solid by using (R)-1-(1-acryloylpyrrolidin-3-yl)-1H-pyrazolo[3,4-d]pyrimidine-3-carboxylic acid (5 mg) and 2-(4-amino-2,3-dimethylphenyl)-N,N-dimethylacetamide (5 mg) synthesized in (Step 3) of Example 13.

Example 60 Synthesis of (R)-1-(1-acryloylpyrrolidin-3-yl)-4-amino-N-(4-(2-(dimethylamino)-2-oxoethyl)-2-vinylphenyl)-H-pyrazolo[3,4-d]pyrimidine-3-carboxamide (Step 1) Synthesis of Example Compound 60

According to (Step 1) of Example 54, 2.82 mg of the title compound was obtained as a brown solid by using (R)-1-

(1-acryloylpyrrolidin-3-yl)-1H-pyrazolo[3,4-d]pyrimidine-3-carboxylic acid (5 mg) and 2-(4-amino-3-vinylphenyl)-N,N-dimethylacetamide (5 mg) synthesized in (Step 2) of Example 48.

Example 61 Synthesis of (R)-1-(1-acryloylpyrrolidin-3-yl)-4-amino-N-(4-(2-(dimethylamino)-2-oxoethyl)naphthalen-1-yl)-H-pyrazolo[3,4-d]pyrimidine-3-carboxamide (Step 1) Synthesis of Example Compound 61

According to (Step 1) of Example 54, 5.3 mg of the title compound was obtained as a yellow solid by using (R)-1-(1-acryloylpyrrolidin-3-yl)-1H-pyrazolo[3,4-d]pyrimidine-3-carboxylic acid (5 mg) and 2-(4-aminonaphthalen-1-yl)-N,N-dimethylacetamide (5 mg) synthesized in (Step 2) of Example 5.

Example 62 Synthesis of (R)-1-(1-acryloylpyrrolidin-3-yl)-4-amino-N-(2-bromo-4-(2-(dimethylamino)-2-oxoethyl)phenyl)-1H-pyrazolo[3,4-d]pyrimidine-3-carboxamide (Step 1) Synthesis of Example Compound 62

According to (Step 1) of Example 54, 0.90 mg of the title compound was obtained as a brown solid by using (R)-1-(1-acryloylpyrrolidin-3-yl)-1H-pyrazolo[3,4-d]pyrimidine-3-carboxylic acid (5 mg) and 2-(4-amino-3-bromophenyl)-N,N-dimethylacetamide (5 mg) synthesized in (Step 2) of Example 17.

Example 63 Synthesis of (R)-4-(1-(1-acryloylpyrrolidin-3-yl)-4-amino-1H-pyrazolo[3,4-d]pyrimidine-3-carboxamido)-3-methylphenyl dimethylcarbamate (Step 1) Synthesis of (R)-1-(1-acryloylpyrrolidin-3-yl)-4-amino-N-(4-hydroxy-2-methylphenyl)-1H-pyrazolo[3,4-d]pyrimidine-3-carboxamide (R)-1-(1-Acryloylpyrrolidin-3-yl)-1H-pyrazolo[3,4-d]pyrimidine-3-carboxylic acid (10 mg) synthesized in Reference Example 5 was dissolved by adding DMF (0.2 mL), 4-amino-3-methylphenol (5.8 mg), and DIPEA (20 μL). To the solution, HATU (17 mg) was then added. The mixture was stirred at room temperature for 1 hour, and then, ethyl acetate and water were added thereto to separate an organic layer. The organic layer was dried over anhydrous sodium sulfate, and the solvent was distilled off under reduced pressure. The residue was purified by silica gel chromatography (chloroform/methanol) to obtain 13 mg of the title compound as a colorless oil.

(Step 2) Synthesis of Example Compound 63

To (R)-1-(1-acryloylpyrrolidin-3-yl)-4-amino-N-(4-hydroxy-2-methylphenyl)-1H-pyrazolo[3,4-d]pyrimidine-3-carboxamide (13 mg) obtained in (Step 1), potassium carbonate (10 mg) and acetonitrile (250 μL) were added to prepare a suspension. Then, N,N-dimethylcarbamoyl chloride (8 mg) was added thereto. The mixture was stirred at 60° C. for 3 hours, and then, chloroform and water were added thereto to separate an organic layer. The organic layer was dried over anhydrous sodium sulfate, and the solvent was distilled off under reduced pressure. The residue was purified by reverse-phase preparative HPLC purification (water/acetonitrile (0.1% formic acid)) to obtain 6.10 mg of the title compound as a white solid.

Example 64 Synthesis of (R)-4-(1-(1-acryloylpyrrolidin-3-yl)-4-amino-1H-pyrazolo[3,4-d]pyrimidine-3-carboxamido)-2,3-dimethylphenyl dimethylcarbamate (Step 1) Synthesis of (R)-1-(1-acryloylpyrrolidin-3-yl)-4-amino-N-(4-hydroxy-2,3-dimethylphenyl)-H-pyrazolo[3,4-d]pyrimidine-3-carboxamide According to (Step 1) of Example 63, 10 mg of the title compound was obtained as a white solid by using 4-amino-2,3-dimethylphenol instead of 4-amino-3-methylphenol.

(Step 2) Synthesis of Example Compound 64

According to (Step 2) of Example 63, 6.70 mg of the title compound was obtained as a white solid by using (R)-1-(1-acryloylpyrrolidin-3-yl)-4-amino-N-(4-hydroxy-2,3-dimethylphenyl)-1H-pyrazolo[3,4-d]pyrimidine-3-carboxamide (10 mg) obtained in (Step 1) instead of (R)-1-(1-acryloylpyrrolidin-3-yl)-4-amino-N-(4-hydroxy-2-methylphenyl)-H-pyrazolo[3,4-d]pyrimidine-3-carboxamide.

Example 65 Synthesis of (R)-1-(1-acryloylpyrrolidin-3-yl)-4-amino-N-(2-chloro-4-(2-(dimethylamino)-2-oxoethyl)-3-fluorophenyl)-1H-pyrazolo[3,4-d]pyrimidine-3-carboxamide (Step 1) Synthesis of Example Compound 65

(R)-1-(1-Acryloylpyrrolidin-3-yl)-1H-pyrazolo[3,4-d]pyrimidine-3-carboxylic acid (5.0 mg) obtained in Reference Example 5 and 2-(4-amino-3-chloro-2-fluorophenyl)-N,N-dimethylacetamide (10 mg) obtained in (Step 3) of Example 50 were dissolved by adding DMSO (0.1 mL) and DIPEA (5 AL). To the solution, HATU (25 mg) was then added. The mixture was stirred at room temperature for 1 hour. Then, DMSO (1 mL) was added thereto, and the mixture was purified by reverse-phase preparative HPLC purification (water/acetonitrile (0.1% formic acid)) to obtain 3.41 mg of the title compound as a white solid.

Example 66 Synthesis of (R,E)-4-(4-amino-1-(1-(4-dimethylamino)but-2-enoyl)piperidin-3-yl)-1H-pyrazolo[3,4-d]pyrimidine-3-carboxamido)naphthalen-1-yl dimethylcarbamate (Step 1) Synthesis of (R)-tert-butyl 3-(4-amino-3-((4-(((dimethylcarbamoyl)oxy)naphthalen-1-yl)carbamoyl)-1H-pyrazolo[3,4-d]pyrimidin-1-yl)piperidine-1-carboxylate (R)-4-Amino-1-(1-(tert-butyloxycarbonyl)piperidin-3-yl)-1H-pyrazolo[3,4-d]pyrimidine-3-carboxylic acid (20 mg) synthesized in Reference Example 2 was dissolved by adding 4-aminonaphthalene-1-dimethylcarbamate (20 mg) synthesized in (Step 2) of Example 58, DMF (0.2 mL), and DIPEA (35 μL). To the solution, HATU (32 mg) was then added, and the mixture was stirred at room temperature for 1 hour. Ethyl acetate and water were added thereto to separate an organic layer. The organic layer was dried over anhydrous sodium sulfate, and the solvent was distilled off under reduced pressure. The residue was purified by silica gel chromatography (chloroform/methanol) to obtain 20 mg of the title compound as a colorless oil.

(Step 2) Synthesis of Example Compound 66

To (R)-tert-butyl 3-(4-amino-3((4-((dimethylcarbamoyl)oxy)naphthalen-1-yl)carbamoyl)-1H-pyrazolo[3,4-d]pyrimidin-1-yl) piperidine-1-carboxylate (20 mg) obtained in (Step 1), a 4 M solution of hydrochloric acid in 1,4-dioxane (0.3 mL) was added, and the mixture was stirred at room temperature for 1 hour. The organic solvent was distilled off under reduced pressure, and then, the residue was dissolved by adding trans-4-dimethylaminocrotonic acid (5 mg), DMF (0.2 mL), and DIPEA (20 μL). To the solution, HATU (15 mg) was then added, and the mixture was stirred at room temperature for 1 hour. DMSO (1.0 mL) was added to the solution, and the mixture was purified by reverse-phase preparative HPLC purification (water/acetonitrile (0.1% formic acid)) to obtain 12.7 mg of the title compound as a white solid.

Example 67 Synthesis of (R)-1-(1-acryloylpyrrolidin-3-yl)-4-amino-N-(5-chloro-4-(2-(dimethylamino)-2-oxoethyl)-2-methylphenyl)-1H-pyrazolo[3,4-d]pyrimidine-3-carboxamide (R)-1-(1-Acryloylpyrrolidin-3-yl)-1H-pyrazolo[3,4-d]pyrimidine-3-carboxylic acid (5.0 mg) obtained in Reference Example 5 and 2-(4-amino-2-chloro-5-methylphenyl)-N,N-dimethylacetamide (10 mg) obtained in (Step 4) of Example 19 were dissolved by adding DMSO (0.1 mL) and DIPEA (5 μL). To the solution, HATU (25 mg) was then added. The mixture was stirred at room temperature for 1 hour. Then, DMSO (1 mL) was added thereto, and the mixture was purified by reverse-phase preparative HPLC purification (water/acetonitrile (0.1% formic acid)) to obtain 5.08 mg of the title compound as a white solid.

Example 68 Synthesis of (R)-4-(1-(1-acryloylpyrimidin-3-yl)-4-amino-1H-pyrazolo[3,4-d]pyrimidine-3-carboxamido)-3-methylphenyl methyl(phenyl)carbamate (Step 1) Synthesis of 3-methyl-4-nitrophenyl methyl(phenyl)carbamate According to (Step 1) of Example 29, 80 mg of the title compound was obtained as a yellow solid by using 3-methyl-4-nitrophenol (50 mg) instead of 2-chloro-4-nitrophenol and using N-methyl-N-phenylcarbamoyl chloride instead of N,N-dimethylcarbamoyl chloride.

(Step 2) Synthesis of 4-amino-3-methylphenyl methyl(phenyl)carbamate

According to (Step 2) of Example 6, 50 mg of the title compound was obtained as a yellow oil by using 3-methyl-4-nitrophenyl methyl(phenyl)carbamate (80 mg) obtained in (Step 1) instead of 2-(3-chloro-4-nitrophenyl)-N,N-dimethylacetamide.

(Step 3) Synthesis of Example Compound 68

According to (Step 3) of Example 4, 3.58 mg of the title compound was obtained as a white solid by using (R)-1-(1-acryloylpiperidin-3-yl)-4-amino-1H-pyrazolo[3,4-d]pyrimidine-3-carboxylic acid (7.5 mg) and 4-amino-3-methylphenyl methyl(phenyl)carbamate (7.5 mg) obtained in (Step 2).

Example 69 Synthesis of (R)-4-(1-(1-acryloylpyrimidin-3-yl)-4-amino-1H-pyrazolo[3,4-d]pyrimidine-3-carboxamido)-3-methylphenyl pyrrolidine-1-carboxylate (Step 1) Synthesis of 3-methyl-4-nitrophenyl pyrrolidine-1-carboxylate According to (Step 1) of Example 29, 80 mg of the title compound was obtained as a yellow solid by using 3-methyl-4-nitrophenol (50 mg) instead of 2-chloro-4-nitrophenol and using 1-pyrrolidinecarboxylic acid chloride instead of N,N-dimethylcarbamoyl chloride.

(Step 2) Synthesis of 4-amino-3-methylphenyl pyrrolidine-1-carboxylate

According to (Step 2) of Example 6, 50 mg of the title compound was obtained as a yellow oil by using 3-methyl-4-nitrophenyl pyrrolidine-1-carboxylate (80 mg) obtained in (Step 1) instead of 2-(3-chloro-4-nitrophenyl)-N,N-dimethylacetamide.

(Step 3) Synthesis of Example Compound 69

According to (Step 3) of Example 4, 3.66 mg of the title compound was obtained as a white solid by using (R)-1-(1-acryloylpiperidin-3-yl)-4-amino-1H-pyrazolo[3,4-d]pyrimidine-3-carboxylic acid (7.5 mg) and 4-amino-3-methylphenyl pyrrolidine-1-carboxylate (7.5 mg) obtained in (Step 2).

Example 70 Synthesis of (R)-4-(1-(1-acryloylpyrimidin-3-yl)-4-amino-1H-pyrazolo[3,4-d]pyrimidine-3-carboxamido)-3-methylphenyl piperidine-1-carboxylate (Step 1) Synthesis of 3-methyl-4-nitrophenyl piperidine-1-carboxylate According to (Step 1) of Example 29, 70 mg of the title compound was obtained as a yellow solid by using 3-methyl-4-nitrophenol (50 mg) instead of 2-chloro-4-nitrophenol and using 1-piperidinecarboxylic acid chloride instead of N,N-dimethylcarbamoyl chloride.

(Step 2) Synthesis of 4-amino-3-methylphenyl pyrrolidine-1-carboxylate

According to (Step 2) of Example 6, 50 mg of the title compound was obtained as a yellow oil by using 3-methyl-4-nitrophenyl piperidine-1-carboxylate (70 mg) obtained in (Step 1) instead of 2-(3-chloro-4-nitrophenyl)-N,N-dimethylacetamide.

(Step 3) Synthesis of Example Compound 70

According to (Step 3) of Example 4, 4.05 mg of the title compound was obtained as a white solid by using (R)-1-(1-acryloylpiperidin-3-yl)-4-amino-1H-pyrazolo[3,4-d]pyrimidine-3-carboxylic acid (7.5 mg) and 4-amino-3-methylphenyl pyrrolidine-1-carboxylate (7.5 mg) obtained in (Step 2).

Example 71 Synthesis of (R)-1-(1-acryloylpiperidin-3-yl)-4-amino-N-(2-methyl-4-(2-oxo-2-(pyrrolidin-1-yl)ethyl)phenyl)-1H-pyrazolo[3,4-d]pyrimidine-3-carboxamide (Step 1) Synthesis of 2-(3-methyl-4-nitrophenyl)-1-(pyrrolidin-1-yl)ethanone According to (Step 1) of Example 4, 55 mg of the title compound was obtained as a yellow oil by using pyrrolidine instead of a 2.0 M solution of dimethylamine in THF.

(Step 2) Synthesis of 2-(4-amino-3-methylphenyl)-1-(pyrrolidin-1-yl)ethanone

According to (Step 2) of Example 6, 50 mg of the title compound was obtained as a yellow oil by using 2-(3-methyl-4-nitrophenyl)-1-(pyrrolidin-1-yl)ethanone (55 mg) obtained in (Step 1) instead of 2-(3-chloro-4-nitrophenyl)-N,N-dimethylacetamide.

(Step 3) Synthesis of Example Compound 71

According to (Step 3) of Example 4, 3.49 mg of the title compound was obtained as a white solid by using (R)-1-(1-acryloylpiperidin-3-yl)-4-amino-1H-pyrazolo[3,4-d]pyrimidine-3-carboxylic acid (10 mg) and 2-(4-amino-3-methylphenyl)-1-(pyrrolidin-1-yl)ethanone (10 mg) obtained in (Step 2).

Example 72 Synthesis of (R)-1-(1-acryloylpiperidin-3-yl)-4-amino-N-(4-(2-methoxy(methyl)amino-2-oxoethyl)-2-methylphenyl)-1H-pyrazolo[3,4-d]pyrimidine-3-carboxamide (Step 1) Synthesis of N-methoxy-N-methyl-2-(3-methyl-4-nitrophenyl)acetamide According to (Step 1) of Example 4, 55 mg of the title compound was obtained as a yellow oil by using N-methoxy-N-methylamine instead of a 2.0 M solution of dimethylamine in THF.

(Step 2) Synthesis of 2-(4-amino-3-methylphenyl)-N-methoxy-N-methylacetamide

According to (Step 2) of Example 6, 50 mg of the title compound was obtained as a yellow oil by using N-methoxy-N-methyl-2-(3-methyl-4-nitrophenyl) acetamide (55 mg) obtained in (Step 1) instead of 2-(3-chloro-4-nitrophenyl)-N,N-dimethylacetamide.

(Step 3) Synthesis of Example Compound 72

According to (Step 3) of Example 4, 4.43 mg of the title compound was obtained as a white solid by using (R)-1-(1-acryloylpiperidin-3-yl)-4-amino-1H-pyrazolo[3,4-d]pyrimidine-3-carboxylic acid (10 mg) and 2-(4-amino-3-methylphenyl)-N-methoxy-N-methylacetamide (10 mg) obtained in (Step 2).

Example 73 Synthesis of (R)-1-(1-acryloylpiperidin-3-yl)-4-amino-N-(4-(2-(3-hydroxyazetidin-1-yl)-2-oxoethyl)-2-methylphenyl)-1H-pyrazolo[3,4-d]pyrimidine-3-carboxamide (Step 1) Synthesis of 1-(3-hydroxyazetidin-1-yl)-2-(3-methyl-4-nitrophenyl)ethanone According to (Step 1) of Example 4, 55 mg of the title compound was obtained as a yellow oil by using 3-hydroxyazetidine instead of a 2.0 M solution of dimethylamine in THF.

(Step 2) Synthesis of 2-(4-amino-3-methylphenyl)-1-(3-hydroxyazetidin-1-yl)ethanone According to (Step 2) of Example 6, 50 mg of the title compound was obtained as a yellow oil by using 1-(3-hydroxyazetidin-1-yl)-2-(3-methyl-4-nitrophenyl)ethanone (55 mg) obtained in (Step 1) instead of 2-(3-chloro-4-nitrophenyl)-N,N-dimethylacetamide.

(Step 3) Synthesis of Example Compound 73

According to (Step 3) of Example 4, 8.14 mg of the title compound was obtained as a brown solid by using (R)-1-(1-acryloylpiperidin-3-yl)-4-amino-1H-pyrazolo[3,4-d]pyrimidine-3-carboxylic acid (10 mg) and 2-(4-amino-3-methylphenyl)-1-(3-hydroxyazetidin-1-yl)ethanone (10 mg) obtained in (Step 2).

Example 74 Synthesis of (R)-1-(1-acryloylpiperidin-3-yl)-4-amino-N-(4-(3,3-dimethylureido)-2-methylphenyl)-1H-pyrazolo[3,4-d]pyrimidine-3-carboxamide (Step 1) Synthesis of 1,1-dimethyl-3-(3-methyl-4-nitrophenyl)urea 3-Methyl-4-nitroaniline (100 mg) was dissolved by adding DMF (3.3 mL) and DIPEA (170 µL). To the solution, dichloromethylene methyliminium chloride (125 mg) was then added. The mixture was stirred at 50° C. for 3 hours, and then, ethyl acetate and water were added thereto to separate an organic layer. The organic layer was dried over anhydrous sodium sulfate, and the solvent was distilled off under reduced pressure. The residue was purified by silica gel chromatography (chloroform/methanol) to obtain 140 mg of the title compound as a colorless oil.

(Step 2) Synthesis of 3-(4-amino-3-methylphenyl)-1,1-dimethylurea

According to (Step 2) of Example 6, 120 mg of the title compound was obtained as a yellow oil by using 1,1-dimethyl-3-(3-methyl-4-nitrophenyl)urea (140 mg) obtained in (Step 1) instead of 2-(3-chloro-4-nitrophenyl)-N,N-dimethylacetamide.

(Step 3) Synthesis of Example Compound 74

According to (Step 3) of Example 4, 6.50 mg of the title compound was obtained as a brown solid by using (R)-1-(1-acryloylpiperidin-3-yl)-4-amino-H-pyrazolo[3,4-d]pyrimidine-3-carboxylic acid (10 mg) and 3-(4-amino-3-methylphenyl)-1,1-dimethylurea (10 mg) obtained in (Step 2).

Example 75 Synthesis of (R)-1-(1-acryloylpiperidin-3-yl)-4-amino-N-(2-methyl-4-(pyrrolidine-1-carboxamido)phenyl)-1H-pyrazolo[3,4-d]pyrimidine-3-carboxamide (Step 1) Synthesis of N-(3-methyl-4-nitrophenyl) pyrrolidine-1-carboxamide 3-Methyl-4-nitroaniline (30 mg) was dissolved by adding DMF (2.0 mL) and sodium hydride (60%) (12 mg). To the solution, 1-pyrrolidinecarboxylic acid chloride (25 µL) was then added. The mixture was stirred at room temperature for 30 minutes, and then, ethyl acetate and water were added thereto to separate an organic layer. The organic layer was dried over anhydrous sodium sulfate, and the solvent was distilled off under reduced pressure. The residue was purified by silica gel chromatography (chloroform/methanol) to obtain 30 mg of the title compound as a colorless oil.

(Step 2) Synthesis of N-(4-amino-3-methylphenyl) pyrrolidine-1-carboxamide

According to (Step 2) of Example 6, 25 mg of the title compound was obtained as a yellow oil by using N-(3-methyl-4-nitrophenyl) pyrrolidine-1-carboxamide (30 mg) obtained in (Step 1) instead of 2-(3-chloro-4-nitrophenyl)-N,N-dimethylacetamide.

(Step 3) Synthesis of Example Compound 75

According to (Step 3) of Example 4, 6.53 mg of the title compound was obtained as a white solid by using (R)-1-(1-acryloylpiperidin-3-yl)-4-amino-1H-pyrazolo[3,4-d]pyrimidine-3-carboxylic acid (10 mg) and N-(4-amino-3-methylphenyl)pyrrolidine-1-carboxamide (10 mg) obtained in (Step 2).

Example 76 Synthesis of 1-((3R)-1-acryloyl-5-fluoropiperidin-3-yl)-4-amino-N-(2-chloro-4-(2-(dimethylamino)-2-oxoethyl)phenyl)-1H-pyrazolo[3,4-d]pyrimidine-3-carboxamide (Step 1) Synthesis of (2S,4R)-methyl 1-benzyl-4-(benzyloxy)pyrrolidine-2-carboxylate To diethyl ether (400 mL), (2S,4R)-methyl 4-(benzyloxy)pyrrolidine-2-carboxylate hydrochloride (4.57 g) was added, and then triethylamine (2.98 g) was added under ice cooling. The mixture was stirred under ice cooling for 30 minutes. Then, benzyl bromide (5.04 g) and triethylamine (2.98 g) were added thereto, and the mixture was stirred overnight at room temperature. The obtained suspension was filtered, and then, the filtrate was washed with water and saturated saline, then dried over anhydrous sodium sulfate, and filtered. After concentration, the obtained residue was purified by silica gel chromatography (hexane/ethyl acetate) to obtain 4.57 g of the title compound as a colorless oil.

(Step 2) Synthesis of ((2S,4R)-methyl 1-benzyl-4-(benzyloxy)pyrrolidin-2-yl)methanol Lithium aluminum hydride (1.99 g) was suspended in THF (100 mL). To the suspension, a solution of (2S,4R)-methyl 1-benzyl-4-(benzyloxy)pyrrolidine-2-carboxylate (11.4 g) in THF (65 mL) was added under ice cooling. The mixture was kept been stirred under ice cooling for 1 hour, and then, sodium sulfate decahydrate (20 g) was added thereto. The mixture was stirred at room temperature for 3 hours. Then, anhydrous sodium sulfate decahydrate (20 g) was added thereto, and the mixture was stirred overnight at room temperature. Anhydrous sodium sulfate (20 g) was further added thereto, and the mixture was stirred for 30 minutes, then filtered through celite, and concentrated to obtain a residue in a yellow oil form. This residue was purified by silica gel chromatography (hexane/ethyl acetate) to obtain 9.16 g of the title compound as a colorless oil.

(Step 3) Synthesis of (3R)-1-benzyl-3-(benzyloxy)-5-fluoropiperidine

To a solution of ((2S,4R)-methyl 1-benzyl-4-(benzyloxy)pyrrolidin-2-yl)methanol (9.16 g) in THR, bis(2-methoxyethyl)aminosulfur trifluoride (6.95 g) was added under ice cooling, and then, the mixture was kept been stirred for 1 hour. Then, the mixture was stirred at room temperature for 1.5 hours. A saturated aqueous solution of sodium bicarbonate was added thereto, followed by extraction with ethyl acetate. Then, the extract was washed with saturated saline, dried using anhydrous sodium sulfate, filtered, and concentrated. The obtained residue was purified by silica gel chromatography (hexane/ethyl acetate) to obtain 6.08 g of the title compound as a colorless oil.

(Step 4) Synthesis of (5R)-tert-butyl-3-fluoro-5-hydroxypiperidine-1-carboxylate (3R)-1-Benzyl-3-(benzyloxy)-5-fluoropiperidine (6.08 g) and di-tert-butyl dicarbonate (4.88 g) were dissolved in ethanol (120 mL). To the solution, palladium hydroxide-active carbon (900 mg) was then added, and the mixture was stirred for 2 days in a hydrogen atmosphere. The suspension was filtered through celite and then concentrated, and the residue was suspended and washed using hexane to obtain 3.98 g of the title compound as a colorless solid.

(Step 5) Synthesis of (5S)-tert-butyl-3-fluoro-5-((4-nitrobenzoyl)oxy)piperidine-1-carboxylate (5R)-tert-Butyl-3-fluoro-5-hydroxypiperidine-1-carboxylate (1.0 g), 4-nitrobenzoic acid (1.14 g), and triphenylphosphine (1.79 g) were dissolved in toluene (100 mL). To the solution, bis(2-methoxyethyl) azodicarboxylate (1.60 g) was then added under ice cooling. The solution was stirred at room temperature for 3 days, then washed with a saturated aqueous solution of sodium bicarbonate and saturated saline, then dried over anhydrous sodium sulfate, filtered, and then concentrated. The obtained residue was purified by silica gel chromatography (hexane/ethyl acetate) to obtain 1.26 g of the title compound as a colorless solid.

(Step 6) Synthesis of (5S)-tert-butyl-3-fluoro-5-hydroxypiperidine-1-carboxylate (5S)-tert-Butyl-3-fluoro-5-((4-nitrobenzoyl)oxy)piperidine-1-carboxylate (1.26 g) was dissolved in a mixed solution of THF (7 mL) and methanol (7 mL). To the solution, a 5 N aqueous sodium hydroxide solution (1.4 mL) was added. The mixture was stirred at room temperature for 1.5 hours, and then, the organic solvent was removed under reduced pressure. The residue was diluted with diethyl ether, then washed with water, a saturated aqueous solution of sodium bicarbonate, and saturated saline, dried over anhydrous sodium sulfate, filtered, and concentrated to obtain the title compound (0.69 g) as a colorless solid.

(Step 7) Synthesis of (3R)-tert-butyl-3-(4-amino-3-iodo-1H-pyrazolo[3,4-d]pyrimidin-1-yl)-5-fluoropiperidine-1-carboxylate The title compound (0.33 g) was obtained as a light brown compound by using (5)-tert-butyl-3-fluoro-5-hydroxypiperidine-1-carboxylate (0.69 g) instead of (S)—N-Boc-3-piperidinol in (Step 1) and (Step 2) of Reference Example 1.

(Step 8) Synthesis of 4-amino-1-((3R)-1-(tert-butoxycarbonyl)-5-fluoropiperidin-3-yl)-1H-pyrazolo[3,4-d]pyrimidine-3-carboxylic acid (3R)-tert-Butyl-3-(4-amino-3-iodo-1H-pyrazolo[3,4-d]pyrimidin-1-yl)-5-fluoropiperidine-1-carboxylate (0.300 g), triethylamine (0.32 g), and a 1,1'-bis(diphenylphosphino)ferrocene-palladium(II) dichloride-dichloromethane complex (0.052 g) were added to methanol (5 mL), and the mixture was stirred at 100° C. for 1 hour at 4.5 atm in carbon monoxide, and then concentrated. The obtained residue was purified by silica gel chromatography (hexane/ethyl acetate). The obtained solid was dissolved in methanol (5 mL). To the solution, a 5 N aqueous sodium hydroxide solution (0.64 mL) was added, and then, the mixture was stirred at room temperature for 4 hours. Then, a 5 N aqueous hydrochloric acid solution (0.65 mL) was added thereto, followed by extraction with chloroform. Then, the extract was dried over anhydrous sodium sulfate, filtered, and concentrated to obtain the title compound (0.21 g) as a colorless solid.

(Step 9) Synthesis of Example Compound 76

4-Amino-1-((3R)-1-(tert-butoxycarbonyl)-5-fluoropiperidin-3-yl)-1H-pyrazolo[3,4-d]pyrimidine-3-carboxylic acid (35 mg), 2-(4-amino-3-chlorophenyl)-N,N-dimethylacetamide (23 mg) obtained in (Step 2) of Example 6, and diisopropylethylamine (23 mg) were dissolved in DMF (1 mL). To the solution, HATU (52 mg) was added, and the mixture was stirred for 2 days. After concentration, the residue was purified by silica gel chromatography and then purified by reverse-phase preparative HPLC purification (water/acetonitrile (0.1% formic acid)). The obtained colorless oil was dissolved in methanol (2 mL). To the solution, a solution of 4 N hydrochloric acid in dioxane (2 mL) was added, and the mixture was stirred at room temperature for 2 hours. After concentration, the obtained yellow solid and diisopropylethylamine (0.039 g) were dissolved in chloroform (5 mL). To the solution, a chloroform solution containing acryloyl chloride (5 mg) was added under ice cooling, and the mixture was stirred for 10 minutes. The solution was purified by silica gel chromatography, concentrated, and then suspended in hexane/ethyl acetate, and the suspension was filtered and dried under reduced pressure to obtain the title compound (25 mg) as a colorless solid.

Example 77 Synthesis of 1-((3R)-1-acryloyl-5-fluoropiperidin-3-yl)-4-amino-N-(4-(2-(dimethylamino)-2-oxoethyl)-2,3-dimethylphenyl)-1H-pyrazolo[3,4-d]pyrimidine-3-carboxamide According to (Step 9) of Example 76, the title compound (21 mg) was obtained as a colorless solid by using 2-(4-amino-2,3-dimethylphenyl)-N,N-dimethylacetamide (22 mg) synthesized in (Step 3) of Example 13 instead of 2-(4-amino-3-chlorophenyl)-N,N-dimethylacetamide.

Example 78 Synthesis of 1-((3R,5S)-1-acryloyl-5-methylpyrrolidin-3-yl)-4-amino-N-(2-chloro-4-(2-dimethylamino)-2-oxoethyl)phenyl)-1H-pyrazolo[3,4-d]pyrimidine-3-carboxamide (Step 1) Synthesis of (2S,4R)-tert-butyl 4-(3-iodo-4-((triphenylphosphoranylidene)amino)-1H-pyrazolo[3,4-d]pyrimidin-1-yl)-2-methylpyrrolidine-1-carboxylate tert-Butyl (2S,4S)-4-hydroxy-2-methyl-pyrrolidine-1-carboxylate (0.30 g), triphenylphosphine, and 3-iodo-1H-pyrazolo[3,4-d]pyrimidin-4-amine were dissolved in THF (7 mL). To the solution, diisopropyl azodicarboxylate (0.443 mL) was added under ice cooling. The solution was stirred at room temperature for 2 hours, and then, THF (10 mL) was further added thereto. After overnight stirring, triphenylphosphine (0.117 g) and diisopropyl azodicarboxylate (0.089 mL) were further added thereto, and the mixture was further stirred for 1 hour. After concentration of the solution, the residue was suspended in ethyl acetate, and the resulting insoluble matter was removed. Then, the filtrate was concentrated, and the residue was purified by silica gel chromatography (hexane/ethyl acetate) to obtain the title compound (0.387 g) as a colorless amorphous.

(Step 2) Synthesis of (2S,4R)-tert-butyl 4-(3-iodo-1H-pyrazolo[3,4-d]pyrimidin-1-yl)-2-methylpyrrolidine-1-carboxylate (2S,4R)-tert-Butyl 4-(3-iodo-4-((triphenylphosphoranylidene)amino)-1H-pyrazolo[3,4-d]pyrimidin-1-yl)-2-methylpyrrolidine-1-carboxylate (0.37 g) synthesized in (Step 1) was dissolved in trifluoroacetic acid (5 mL), and the solution was stirred overnight. After concentration, chloroform and water were added to the residue, and then, the mixture was rendered basic using 5 N sodium hydroxide, followed by extraction with chloroform/methanol. The obtained organic layer was dried over anhydrous sodium sulfate, filtered, and concentrated. The obtained colorless solid was dissolved in chloroform (5 mL). To the solution, di-tert-butyl dicarbonate (0.126 g) was added, and the mixture was stirred at room temperature for 2 hours. After concentration, the residue was purified by silica gel chromatography (chloroform/methanol) to obtain the title compound (0.23 g) as a colorless solid.

(Step 3) Synthesis of 4-amino-1-((3R,5S)-1-(tert-butoxycarbonyl)-5-methylpyrrolidin-3-yl)-1H-pyrazolo[3,4-d]pyrimidine-3-carboxylic acid According to (Step 8) of Example 76, the title compound (0.138 g) was obtained as a brown solid by using (2S,4R)-tert-butyl 4-(3-iodo-1H-pyrazolo[3,4-d]pyrimidin-1-yl)-2-methylpyrrolidine-1-carboxylate (0.23 g) obtained in (Step 2) instead of (3R)-tert-butyl-3-(4-amino-3-iodo-1H-pyrazolo[3,4-d]pyrimidin-1-yl)-5-fluoropiperidine-1-carboxylate.

(Step 4) Synthesis of Example Compound 78

According to (Step 9) of Example 76, the title compound (23 mg) was obtained as a colorless solid by using 4-amino-1-((3R,5S)-1-(tert-butoxycarbonyl)-5-methylpyrrolidin-3-yl)-1H-pyrazolo[3,4-d]pyrimidine-3-carboxylic acid (35 mg) and 2-(4-amino-3-chlorophenyl)-N,N-dimethylacetamide (24 mg) obtained in (Step 2) of Example 6 instead of 4-amino-1-((3R)-1-(tert-butoxycarbonyl)-5-fluoropiperidin-3-yl)-1H-pyrazolo[3,4-d]pyrimidine-3-carboxylic acid.

Example 79 Synthesis of 1-((3R,5S)-1-acryloyl-5-methylpyrrolidin-3-yl)-4-amino-N-(4-(2-dimethylamino)-2-oxoethyl)-2,3-dimethylphenyl)-1H-pyrazolo[3,4-d]pyrimidine-3-carboxamide According to (Step 9) of Example 76, the title compound (36 mg) was obtained as a colorless solid by using 4-amino-1-((3R,5S)-1-(tert-butoxycarbonyl)-5-methylpyrrolidin-3-yl)-1H-pyrazolo[3,4-d]pyrimidine-3-carboxylic acid (35 mg) and 2-(4-amino-2,3-dimethylphenyl)-N,N-dimethylacetamide (24 mg) synthesized in (Step 3) of Example 13 instead of 4-amino-1-((3R)-1-(tert-butoxycarbonyl)-5-fluoropiperidin-3-yl)-1H-pyrazolo[3,4-d]pyrimidine-3-carboxylic acid.

Comparative Example Compound 1 Synthesis of (R)-1-(1-acryloylpiperidin-3-yl)-4-amino-N-(5-fluorobenzo[d]oxazol-2-yl)-H-pyrazolo[3,4-d]pyrimidine-3-carboxamide The title compound was obtained as a white solid by synthesis according to the method of the pamphlet of International Publication No. WO 2015/022926.

Hereinafter, a list of Example compounds 1 to 79 and Comparative Example compound 1 is shown below.

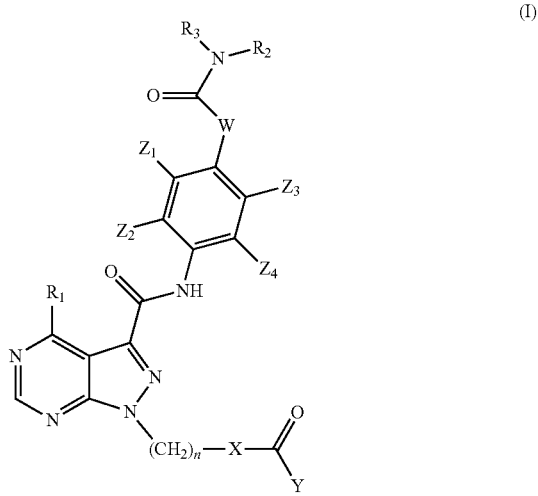

(I)

TABLE 1

| # | W (R3,R2,N) | Z1,Z2,Z3,Z4 ring | R1 / (CH2)n-X-C(O)-Y | NMR | mass |
|---|---|---|---|---|---|
| 1 | H3C\N/CH3, CH2 | Br, CH3 substituents; NH | NH2; piperidine-N-acryloyl | 1H-NMR (DMSO-D6) δ: 1.53-1.67 (m, 1.0H), 1.93-2.03 (m, 1.0H), 2.15-2.52 (m, 5.0H), 2.85 (s, 3.0H), 3.03 (s, 3.0H), 3.14-3.89 (m, 2.0H), 3.78 (s, 2.0H), 4.00-4.87 (m, 3.0H), 5.58-5.71 (m, 1.0H), 6.00-6.17 (m, 1.0H), 6.68-6.92 (m, 1.0H), 7.20 (s, 1.0H), 7.68-7.76 (m, 1.0H), 8.15 (s, 1.0H), 8.27 (s, 1.0H), 8.48 (s, 1.0H), 10.02-10.22 (m, 1.0H). | 569.2 |
| 2 | H3C\N/CH3, CH2 | H3C, Cl substituents; NH | NH2; piperidine-N-acryloyl | 1H NMR (400 MHz. CDCl3) Shift 1.63-1.85 (m, 1H), 1.95-2.10 (m, 1H), 2.16-2.41 (m, 5H), 3.01 (s, 3H), 3.05 (s, 3H), 3.18-3.78 (m, 3H), 3.95-4.30 (m, 1H), 4.41-5.02 (m, 2H), 5.61-5.78 (m, 1H), 6.29 (dd, J = 15.85, 7.07 Hz, 1H), 6.40-6.72 (m, 2H), 7.23 (s, 1H), 8.21-8.43 (m, 2H), 8.80 (br. d, J = 8.00 Hz, 1H), 9.43 (s, 1H) | 525.3 |

TABLE 1-continued

| | R3\N\R2 (W) | | Z1,Z2,Z3,Z4 benzene with NH | R1 pyrazolopyrimidine-(CH2)n-X-C(O)-Y | NMR | mass |
|---|---|---|---|---|---|---|
| 3 | H3C\N\CH3 | CH2 | 4-position, with CH3 and Cl, NH | NH2 pyrazolopyrimidine, piperidine-acryloyl | 1H NMR (400 MHz, CDCl3) Shift 1.15-1.48 (m, 1H), 1.64-1.87 (m, 1H), 1.98-2.18 (m, 1H), 2.26-2.34 (m, 2H), 2.37 (s, 3H), 3.02 (s, 3H), 3.08 (s, 3H), 3.22-3.56 (m, 1H), 3.73 (s, 2H), 3.96-4.63 (m, 1H), 4.78-5.04 (m, 1H), 5.60-5.84 (m, 1H), 6.23-6.73 (m, 3H), 7.00-7.18 (m, 1H), 8.10-8.44 (m, 2H), 8.82 (br. d, J = 11.00 Hz, 1H), 9.63 (s, 1H) | 525.3 |
| 4 | H3C\N\CH3 | CH2 | benzene with CH3, NH | NH2 pyrazolopyrimidine, piperidine-acryloyl | 1H NMR (400 MHz, DMSO) Shift 1.58 (br. s., 1H), 1.95 (br. s., 1H), 2.12-2.25 (m, 4H), 2.29 (br. s., 1H), 2.81 (d, J = 3.42 Hz, 3H), 2.99 (d, J = 4.10 Hz, 3H), 3.63 (br. s., 2H), 4.09 (br. s., 1H), 4.50 (br. s., 1H), 4.70 (br. s., 1H), 5.68 (br. s., 1H), 6.00-6.12 (m, 1H), 6.82 (br. s., 1H), 7.03-7.14 (m, 2H), 7.37 (br. s., 1H), 8.06 (br. s., 1H), 8.24 (br. s., 1H), 8.53 (br. s., 1H), 10.01 (br. s.,1H) | 491.3 |
| 5 | H3C\N\CH3 | CH2 | naphthalene with NH | NH2 pyrazolopyrimidine, piperidine-acryloyl | 1H NMR (400 MHz, DMSO-d6) Shift 1.59 (br. s., 1H), 1.96 (br. s., 1H), 2.21 (br. s., 1H), 2.38 (br. s., 1H), 2.50 (s, 1H), 2.85 (s, 3H), 3.02 (s., 3H), 3.83 (br. s., 1H), 4.06 (br. s., 2H), 4.15 (s, 3H), 4.26 (br. s., 1H), 4.77 (br. s., 1H), 5.58-5.70 (m, 1H), 6.09 (d, J = 16.40 Hz, 1H), 6.61-6.94 (m, 1H), 7.35 (d, J = 7.52 Hz, 1H), 7.54 (d, J = 8.88 Hz, 3H), 7.83-7.99 (m, 2H), 8.04 (br. s., 1H), 8.25 (s. 1H), 8.50 (br. s., 1H), 10.42-10.80 (m, 1H) | 527.3 |
| 6 | H3C\N\CH3 | CH2 | benzene with Cl, NH | NH2 pyrazolopyrimidine, piperidine-acryloyl | 1H NMR (400 MHz, DMSO-d6) Shift 1.53-1.70 (m, 1H), 1.92-2.03 (m, 1H), 2.14-2.37 (m, 2H), 2.84 (s, 3H), 3.03 (s, 3H), 3.18-3.40 (m, 1H), 3.68-3.80 (m, 1H), 3.74 (s, 2H), 4.02-4.57 (m, 2H), 4.69-4.81 (m, 1H), 5.56-5.71 (m, 1H), 6.03-6.14 (m, 1H), 6.66-6.93 (m, 1H), 7.22-7.27 (m, 1H), 7.38-7.46 (m, 1H), 7.74-7.82 (m, 1H), 8.19 (br s, 1H), 8.28 (s, 1H), 8.42 (br s, 1H), 10.13 (br s, 1H) | 511.2 |

TABLE 1-continued

| | W | | | NMR | mass |
|---|---|---|---|---|---|
| 7 | H₃C-N-CH₃ | CH2 | (phenyl with OCH3, NH) | (pyrazolopyrimidine with NH2, piperidine acrylamide) | 1H NMR (400 MHz, DMSO) Shift 1.60 (br. s., 1H), 1.95 (br. s., 1H), 2.18 (br. s., 1H), 2.27 (d, J = 14.35 Hz, 1H), 2.81 (s, 3H), 2.99 (s, 3H), 3.66 (s, 2H), 3.79 (br. s., 1H), 3.87 (s, 3H), 3.99 (d, J = 7.52 Hz, 1H), 4.13-4.48 (m, 1H), 4.73 (br. s., 1H), 5.48-5.69 (m, 1H), 5.98-6.10 (m, 1H), 6.57-6.87 (m, 2H), 6.97 (s, 1H), 8.01 (d, J = 8.20 Hz, 1H), 8.15 (br. s., 1H), 8.26 (s, 1H), 8.48 (br. s., 1H), 9.61 (br. s., 1H) | 507.3 |
| 8 | H₃C-N-CH₃ | CH2 | (phenyl with Cl, NH) | (pyrazolopyrimidine with NH2, piperidine acrylamide) | 1H NMR (400 MHz, DMSO-d6) Shift 2.15 (br. s., 1H), 2.37-2.55 (m, 1H), 2.73 (br. s., 1H), 3.40 (s, 3H), 3.62 (s, 3H), 4.32 (s, 3H), 4.64 (br. s., 2H), 4.70-5.16 (m, 2H), 5.18-5.44 (m, 1H), 6.27 (br. s., 1H), 6.66 (br. s., 1H), 7.41 (br. s., 1H), 7.84 (d, J = 8.20 Hz, 1H), 8.29 (d, J = 8.88 Hz, 1H), 8.53 (br. s., 1H), 8.67-8.77 (m, 2H), 8.83 (s, 1H), 8.97 (br. s., 1H), 10.79-11.13 (m, 1H) | 510.3 |

TABLE 2

| 9 | H₃C-N-CH₃ | CH2 | (phenyl with Cl, OCH3, NH) | (pyrazolopyrimidine with NH2, piperidine acrylamide) | 1H NMR (400 MHz, DMSO-d6) Shift 1.25 (d, J = 6.15 Hz, 1H), 1.55-1.74 (m, 1H), 1.99 (s, 1H), 2.22 (m, 1H), 2.28 (br. s., 1H), 2.63-2.90 (m, 3H), 3.09 (s, 3H), 3.39-3.59 (m, 1H), 3.79 (s, 2H), 3.92 (s, 3H), 3.95-4.10 (m, 1H), 4.15-4.53 (m, 1H), 4.71-4.89 (m, 1H), 5.51-5.76 (m, 1H), 6.08 (br. s., 1H), 6.59-6.99 (m, 1H), 7.10 (s, 1H), 8.20 (s, 2H), 8.30 (s, 1H), 8.40 (br. s., 1H), 9.67 (br. s., 1H) | 541.3 |
| 10 | H₃C-N-CH₃ | CH2 | (phenyl with F, CH3, NH) | (pyrazolopyrimidine with NH2, piperidine acrylamide) | 1H NMR (400 MHz, DMSO-d6) Shift: 1.54-1.69 (m, 1H), 1.91-2.05 (m, 1H), 2.13-2.42 (m, 2H), 2.22 (s, 3H), 2.85 (s, 3H), 3.00-3.27 (m, 2H), 3.06 (s, 3H), 3.29-3.82 (m, 2H), 3.69 (s, 2H), 4.00-4.61 (m, 2H), 4.67-4.85 (m, 1H), 5.54-5.73 (m, 1H), 6.03-6.16 (m, 1H), 6.66-6.91 (m, 1H), 7.14 (d, J = 8.0 Hz, 1H), 7.34-7.41 (m, 1H), 8.16 (br s, 1H), 8.27 (s, 1H), 8.49 (br s, 1H), 10.00-10.10 (m, 1H) | 509.3 |
| 11 | H₃C-N-CH₃ | CH2 | (phenyl with Cl, OCH3, NH) | (pyrazolopyrimidine with NH2, piperidine acrylamide) | 1H NMR (400 MHz, DMSO-d6) Shift 1.62 (br. s., 1H), 2.02 (br. s., 1H), 2.21 (br. s., 1H), 2.29 (m, 1H), 2.84 (s, 3H), 3.06 (s, 3H), 3.79 (s, 2H), 3.86 (s, 3H), 4.03 (br. s., 1H), 4.19 (br. s., 1H), 4.49 (d, J = 11.62 Hz, 1H), 4.76 (br. s., 1H), 5.45-5.72 (m, 1H), 5.97-6.12 (m, 1H), 6.54-6.89 (m, 1H), 7.11 (d, J = 8.20 Hz, 1H), 7.97 (d, J = 8.20 Hz, 1H), 8.20 (br. s., 1H), 8.28 (s, 1H), 8.37 (br. s., 1H), 9.81 (br. s., 1H) | 541.3 |

TABLE 2-continued

| | | | | | | |
|---|---|---|---|---|---|---|
| 12 | H3C−N−CH3 | CH2 | [phenyl with F, CH3, NH] | [pyrazolopyrimidine with NH2, piperidine-acryloyl] | 1H NMR (400 MHz, DMSO-d6) Shift 1.59 (br. s., 1H), 1.94 (br. s., 1H), 2.12 (s, 3H), 2.18 (br. s., 1H), 2.30 (br. s., 1H), 2.83 (s, 3H), 3.05 (s, 3H), 3.10-3.25 (m, 1H), 3.70 (s, 2H), 4.05 (d, J = 15.03 Hz, 1H), 3.78 (br. s., 1H), 4.13-4.30 (m, 1H), 4.55 (d, J = 11.62 Hz, 1H), 4.74 (br. s., 1H), 5.54-5.72 (m, 1H), 6.02-6.14 (m, 1H), 6.84 (br. s., 1H), 7.05-7.12 (m, 1H), 7.20 (br. s., 1H), 8.09 (br. s., 1H), 8.25 (s, 1H), 8.48 (br. s., 1H), 10.12-10.28 (m, 1H) | 509.3 |
| 13 | H3C−N−CH3 | CH2 | [phenyl with 2×CH3, NH] | [pyrazolopyrimidine with NH2, piperidine-acryloyl] | 1H NMR (400 MHz, DMSO-d6) Shift 1.52-1.69 (m, 1H), 1.92-2.03 (m, 1H), 2.06-2.41 (m, 2H), 2.10 (s, 3H), 2.13 (s, 3H), 2.65 (s, 3H), 2.99-3.24 (m, 1H), 3.05 (s, 3H), 3.29-3.85 (m, 1H), 3.33 (s, 2H), 3.99-4.58 (m, 2H), 4.67-4.81 (m, 1H), 5.58-5.73 (m, 1H), 6.05-6.15 (m, 1H), 6.71-6.96 (m, 1H), 6.95 (d, J = 8.0 Hz, 1H), 7.10-7.15 (m, 1H), 8.09 (br s, 1H), 8.26 (s, 1H), 8.60 (br s, 1H), 10.11-10.24 (m, 1H). | 505.3 |
| 14 | H3C−N−CH3 | CH2 | [phenyl with F, OCH3, NH] | [pyrazolopyrimidine with NH2, piperidine-acryloyl] | 1H NMR (400 MHz, DMSO-d6) Shift 1.62 (br. s., 1H), 2.02 (br. s., 1H), 2.21 (br. s., 1H), 2.27 (br. s., 1H), 2.83 (s, 3H), 3.05 (s, 3H), 3.71 (s, 2H), 3.78 (m., 1H), 3.94 (s., 3H), 4.04 (d, J = 19.82 Hz, 2H), 4.17 (br. s., 1H), 4.45 (br. s., 1H), 4.52-4.56 (m, 1H), 4.52-4.57 (m, 1H), 4.71-4.87 (m, 1H), 5.38-5.77 (m, 1H), 5.98-6.11 (m, 1H), 6.51-6.90 (m, 1H), 6.98 (t, J = 7.86 Hz, 1H), 7.77 (d, J = 8.20 Hz, 1H), 8.18 (br, s., 1H), 8.27 (s, 1H), 8.40 (br. s., 1H), 9.80 (br. s., 1H) | 525.3 |
| 15 | H3C−N−CH3 | CH2 | [phenyl with OCHF2, NH] | [pyrazolopyrimidine with NH2, piperidine-acryloyl] | 1H NMR (400 MHz, DMSO) Shift 1.60 (br. s., 1H), 1.96 (br. s, 1H), 2.19 (br. s., 1H), 2.26 (br. s., 1H), 2.82 (s, 3H), 3.01 (s, 3H), 3.72 (s, 2H), 3.95-4.18 (m, 1H), 4.19-4.54 (m, 1H), 4.77 (br. s., 1H), 5.52-5.70 (m, 1H), 6.01-6.12 (m, 1H), 6.81 (d, J = 10.25 Hz, 1H), 7.12-7.21 (m, 3H), 7.87 (d, J = 8.20 Hz, 1H), 8.16 (br. s., 1H), 8.27 (s, 1H), 8.39 (br. s., 1H), 9.87 (br. s., 1H) | 543.3 |
| 16 | H3C−N−CH3 | CH2 | [phenyl with OCH2F, NH] | [pyrazolopyrimidine with NH2, piperidine-acryloyl] | 1H NMR (400 MHz, DMSO) Shift 1.60 (br. s., 1H), 1.96 (s, 1H), 2.19 (br. s., 2H), 2.82 (s, 3H), 2.98-3.03 (m, 3H), 3.63-3.75 (m, 2H), 3.80 (br. s., 1H), 4.00 (d, J = 7.52 Hz, 1H), 4.12-4.52 (m, 1H), 4.70-4.88 (m, 1H), 5.49-5.73 (m, 1H), 5.83 (br. s., 1H), 5.94-6.12 (m, 2H), 6.59-6.91 (m, 1H), 7.01 (d, J = 8.20 Hz, 1H), 7.16 (s, 1H), 7.97 (br. s., 1H), 8.17 (br. s., 1H), 8.27 (s, 1H), 8.44 (br. s., 1H), 9.73 (d, J = 15.72 Hz, 1H) | 525.3 |

TABLE 3

| | | | | | | |
|---|---|---|---|---|---|---|
| 17 | H3C−N−CH3 | CH2 | [phenyl with Br, NH] | [pyrazolopyrimidine with NH2, piperidine-acryloyl] | 1H NMR (400 MHz, DMSO-d6) Shift 1.59 (br. s., 1H), 1.96 (br. s., 1H), 2.18 (br. s., 1H), 2.29 (br. s., 1H), 2.81 (s, 3H), 3.01 (s, 4H), 3.13 (d, J = 5.47 Hz, 1H), 3.70 (s, 3H), 4.02 (br. s., 1H), 4.15 (br. s., 1H), 4.50 (d, J = 12.98 Hz, 1H), 4.74 (br. s., 1H), 5.51-5.69 (m, 1H), 6.08 (d, J = 15.72 Hz, 1H), 6.83 (br. s., 1H), 7.26 (d, J = 8.20 Hz, 1H), 7.56 (s, 1H), 7.79 (br. s., 1H), 8.09-8.19 (m, 1H), 8.26 (s, 1H), 8.38 (br. s., 1H), 10.05 (s, 1H) | 555.2 |

TABLE 3-continued

| # | R1 | X | Aryl | Het | NMR | MS |
|---|---|---|---|---|---|---|
| 18 | H3C-N-CH3 | CH2 | 2-Cl, 4-F, 5-NH- phenyl | 4-amino-pyrazolo[3,4-d]pyrimidine with (acryloyl-piperidin-3-yl) | 1H NMR (400 MHz, DMSO-d6) Shift 1.51-1.74 (m, 1H), 1.98 (d, J = 12.10 Hz, 1H), 2.12-2.38 (m, 2H), 2.78-2.92 (m, 3H), 3.03 (s, 3H), 3.74 (s, 3H), 3.98-4.56 (m, 2H), 4.75 (br. s., 1H), 5.52-5.73 (m, 1H), 5.97-6.24 (m, 1H), 6.62-6.99 (m, 1H), 7.49 (d, J = 7.33 Hz, 1H), 7.80 (d, J = 10.63 Hz, 1H), 8.17-8.39 (m, 3H), 10.11 (s, 1H) | 529.3 |
| 19 | H3C-N-CH3 | CH2 | 2-Cl, 5-CH3, 4-NH- phenyl | 4-amino-pyrazolo[3,4-d]pyrimidine with (acryloyl-piperidin-3-yl) | 1H NMR (400 MHz, DMSO-d6) Shift 1.07-1.37 (m, 1H), 1.47-1.69 (m, 1H), 1.88-2.03 (m, 1H), 2.11-2.30 (m, 5H), 2.83 (s, 3H), 3.05 (s, 3H), 3.74 (s, 3H), 3.94-4.58 (m, 3H), 4.64-4.86 (m, 1H), 5.50-5.74 (m, 1H), 5.89-6.21 (m, 1H), 6.57-6.90 (m, 1H), 7.18 (s, 1H), 7.56 (d, J = 10.93 Hz, 1H), 8.12 (s, 1H), 8.25 (s, 1H), 8.45 (br. s., 1H), 10.05 (d, J = 38.30 Hz, 1H) | 525.3 |
| 20 | H3C-N-CH3 | CH2 | 2,5-diCl, 4-NH- phenyl | 4-amino-pyrazolo[3,4-d]pyrimidine with (acryloyl-piperidin-3-yl) | No data | 545.2 |
| 21 | H3C-N-CH3 | O | 4-NH-phenyl | 4-amino-pyrazolo[3,4-d]pyrimidine with (acryloyl-piperidin-3-yl) | No data | 479.3 |
| 22 | H3C-N-CH3 | CH2 | 2-cyclopropyl, 4-NH-phenyl | 4-amino-pyrazolo[3,4-d]pyrimidine with (acryloyl-piperidin-3-yl) | 1H-NMR (DMSO-D6) δ: 0.56-0.71 (m, 2.0H), 0.91-1.05 (m, 2.0H), 1.54-1.71 (m, 1.0H), 1.90-2.06 (m, 2.0H), 2.16-2.34 (m, 2.0H), 2.82 (s, 3.0H), 3.00 (s, 3.0H), 3.14-3.84 (m, 2.0H), 3.65 (s, 2.0H), 4.00-4.91 (m, 3.0H), 5.56-5.71 (m, 1.0H), 5.96-6.18 (m, 1.0H), 6.62-6.91 (m, 1.0H), 7.00 (s, 1.0H), 7.06-7.12 (m, 1.0H), 7.74-7.81 (m, 1.0H), 8.21 (s, 1.0H), 8.28 (s, 1.0H), 8.57 (s, 1.0H), 9.98-10.11 (m, 1.0H). | 517.3 |
| 23 | H3C-N-CH3 | CH2 | 2-CN, 4-NH- phenyl | 4-amino-pyrazolo[3,4-d]pyrimidine with (acryloyl-piperidin-3-yl) | 1H-NMR (DMSO-D6) δ: 1.49-1.69 (m, 1.0H), 1.86-2.03 (m, 1.0H), 2.16-2.53 (m, 2.0H), 2.84-3.85 (m, 2.0H), 2.84 (s, 3.0H), 3.04 (s, 3.0H), 3.80 (s, 2.0H), 4.04-4.87 (m, 3.0H), 5.60-5.78 (m, 1.0H), 6.01-6.20 (m, 1.0H), 6.73-6.92 (m, 1.0H), 7.54-7.64 (m, 2.0H), 7.72 (s, 1.0H), 8.18 (s, 1.0H), 8.29 (s, 1.0H), 8.37 (s, 1.0H), 10.79 (s, 1.0H). | 502.3 |
| 24 | H3C-N-CH3 | CH2 | 2-CN, 5-CH3, 4-NH-phenyl | 4-amino-pyrazolo[3,4-d]pyrimidine with (acryloyl-piperidin-3-yl) | 1H-NMR (DMSO-D6) δ: 1.58-1.67 (m, 1.0H), 1.93-2.04 (m, 1.0H), 2.12-2.46 (m, 5.0H), 2.85 (s, 3.0H), 2.96-3.81 (m, 2.0H), 3.09 (s, 3.0H), 3.89 (s, 2.0H), 4.06-4.80 (m, 3.0H), 5.56-5.74 (m, 1.0H), 6.04-6.16 (m, 1.0H), 6.67-6.94 (m, 1.0H), 7.36 (s, 1.0H), 7.85-7.91 (m, 1.0H), 8.16 (s, 1.0H), 8.27 (s, 1.0H), 8.46 (s, 1.0H), 10.15-10.38 (m, 1.0H). | 516.3 |

US 9,920,060 B2

TABLE 3-continued

| 25 | 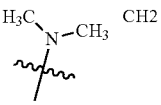 | CH2 | 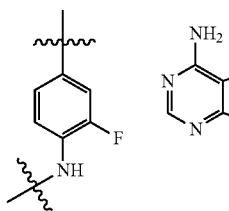 | 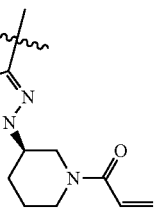 | 1H-NMR (DMSO-D6) δ: 1.56-1.63 (m, 1.0H), 1.92-1.96 (m, 1.0H), 2.14-2.36 (m, 2.0H), 2.82 (s, 3.0H), 2.88-3.75 (m, 2.0H), 3.02 (s, 3.0H), 3.72 (s, 2.0H), 4.00-4.80 (m, 3.0H), 5.54-5.74 (m, 1.0H), 6.01-6.14 (m, 1.0H), 6.70-6.88 (m, 1.0H), 7.07 (dd, J = 8.2, 1.3 Hz, 1.0H), 7.16 (dd, J = 11.7, 1.3 Hz, 1.0H), 7.53-7.60 (m, 1.0H), 8.12 (s, 1.0H), 8.26 (s, 1.0H), 8.43 (s, 1.0H), 10.20-10.15 (m, 1.0H). | 495.3 |

TABLE 4

| 26 | 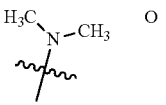 | O | 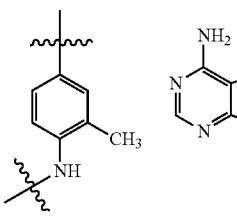 | 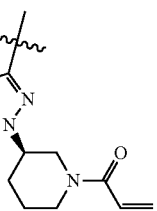 | 1H NMR (400 MHz, DMSO-d6) Shift 0.03 (br. s., 1H), 1.57 (br. s., 1H), 1.96 (br. s., 1H), 2.22 (br. s., 3H), 2.26-2.29 (m, 1H), 2.88 (br. s., 3H), 3.01 (br. s., 3H), 3.78 (br. s., 1H), 4.03 (br. s., 1H), 4.14 (br. s., 1H), 4.21 (br. s., 1H), 4.50 (br. s., 1H), 4.73 (br. s., 1H), 5.52-5.73 (m, 1H), 5.58 (br. s., 1H), 5.68 (br. s., 1H), 5.97-6.15 (m, 1H), 6.06 (s, 1H), 6.10 (s, 1H), 6.64-6.89 (m, 1H), 6.69 (br. s., 1H), 6.83 (br. s., 1H), 6.96 (br. s., 1H), 7.03 (br. s., 1H), 7.40 (br. s., 1H), 8.06 (br. s., 1H), 8.24 (br. s., 1H), 8.51 (br. s., 1H), 9.98-10.14 (m, 1H), 10.01 (br. s., 1H), 10.09 (br. s., 1H) | 493.3 |
| 27 | 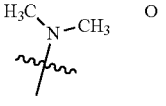 | O | 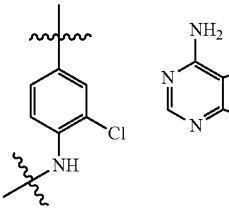 | 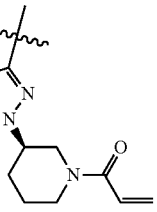 | 1H NMR (400 MHz, DMSO-d6) Shift 1.59 (br. s., 1H), 1.94 (br. s., 1H), 2.18 (br. s., 1H), 2.29 (br. s., 1H), 2.89 (s, 3H), 3.02 (s, 3H), 3.74 (br. s., 1H), 4.04 (br. s., 1H), 4.54 (br. s., 1H), 4.74 (br. s., 1H), 5.53-5.70 (m, 1H), 6.08 (d, J = 14.35 Hz, 1H), 6.62-6.88 (m, 1H), 7.17 (dd, J = 8.54, 2.39 Hz, 1H), 7.42 (d, J = 2.73 Hz, 1H), 7.79 (d, J = 8.88 Hz, 1H), 8.13 (br. s., 1H), 8.26 (s, 1H), 8.38 (br. s., 1H), 10.16 (br. s., 1H) | 513.2 |
| 28 | 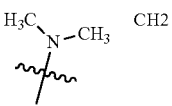 | CH2 | 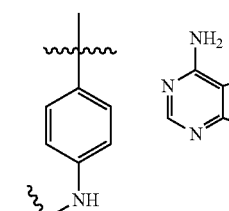 | 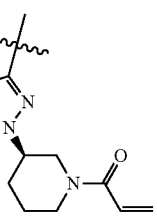 | 1H NMR (400 MHz, DMSO-d6) Shift 1.59 (br. s., 1H), 1.90 (br. s., 1H), 2.15 (br. s., 1H), 2.29 (br. s., 1H), 2.81 (d, J = 4.10 Hz, 3H), 2.99 (d, J = 4.10 Hz, 4H), 3.64 (br. s., 2H), 3.82 (br. s., 1H), 3.96-4.14 (m, 1H), 4.14-4.59 (m, 1H), 4.63-4.86 (m, 1H), 5.53-5.79 (m, 1H), 6.09 (br. s., 1H), 6.65-6.92 (m, 1H), 7.21 (br. s., 2H), 7.71 (br. s., 2H), 8.10 (br. s., 1H), 8.22 (d, J = 15.03 Hz, 1H), 8.49 (br. s., 1H), 10.09-10.38 (m, 1H) | 477.3 |
| 29 | 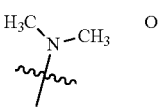 | O | 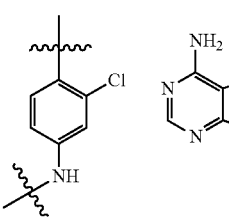 | 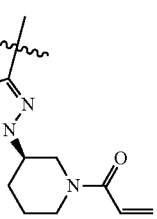 | 1H NMR (400 MHz, DMSO-d6) Shift 1.57 (br. s., 1H), 1.90 (br. s., 1H), 2.15 (br. s., 1H), 2.29 (br. s., 1H), 2.90 (br. s., 3H), 3.05 (br. s., 4H), 3.79 (br. s., 1H), 4.06 (br. s., 1H), 4.22 (br. s., 1H), 4.53 (br. s., 1H), 4.70 (br. s., 1H), 5.55-5.71 (m, 1H), 6.09 (br. s., 1H), 6.85 (br. s., 1H), 7.31 (br. s., 1H), 7.78 (d, J = 6.83 Hz, 1H), 8.04 (br. s., 1H), 8.14 (br. s., 1H), 8.25 (br. s., 1H), 8.37 (br. s., 1H), 8.43 (br. s., 1H), 10.32-10.67 (m, 1H) | 513.2 |
| 30 | 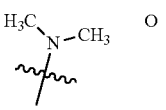 | O | 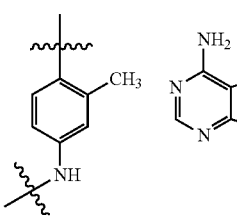 | 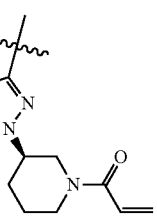 | 1H NMR (400 MHz, DMSO-d6) Shift 1.58 (br. s., 1H), 1.90 (br. s., 1H), 2.12 (br. s., 4H), 2.28 (br. s., 1H), 2.89 (br. s., 3H), 3.05 (br. s., 3H), 3.75-3.91 (m, 1H), 3.97-4.26 (m, 2H), 4.42-4.58 (m, 1H), 4.63-4.85 (m, 1H), 5.51-5.78 (m, 1H), 6.09 (br. s., 1H), 6.63-6.93 (m, 1H), 7.05 (br. s., 1H), 7.61 (br. s., 1H), 7.69 (br. s., 1H), 8.11 (br. s., 1H), 8.24 (br. s., 1H), 8.36 (br. s., 1H), 8.47 (br. s., 1H), 10.03-10.46 (m, 1H) | 493.3 |

TABLE 4-continued

| | | | | | | |
|---|---|---|---|---|---|---|
| 31 | H₃C−N−CH₃ | O | (4-NH-2-F-phenyl) | (4-amino-pyrazolopyrimidine-piperidine-acryloyl) | 1H NMR (400 MHz, DMSO-d6) Shift 1.58 (br. s., 1H), 1.91 (br. s., 1H), 2.16 (br. s., 1H), 2.30 (br. s., 1H), 2.89 (br. s., 4H), 3.02 (br. s., 3H), 3.72 (br. s., 1H), 4.07 (br. s., 1H), 4.25 (br. s., 1H), 4.55 (br. s., 1H), 4.73 (br. s., 1H), 5.56-5.71 (m, 1H), 6.11 (br. s., 1H), 6.66-6.88 (m, 1H), 7.01 (d, J = 6.15 Hz, 1H), 7.20 (d, J = 8.88 Hz, 1H), 7.60 (br. s., 1H), 8.10 (br. s., 1H), 8.25 (br. s., 1H), 8.43 (br. s., 1H), 10.26 (br. s., 1H) | 497.3 |
| 32 | H₃C−N−CH₃ | O | (4-NH-2,3-diMe-phenyl) | (4-amino-pyrazolopyrimidine-piperidine-acryloyl) | 1H NMR (400 MHz, DMSO-d6) Shift 1.57 (br. s., 1H), 1.94 (br. s., 1H), 2.05 (br. s., 3H), 2.12 (br. s., 4H), 2.30 (br. s., 1H), 2.89 (br. s., 3H), 3.06 (br. s., 3H), 3.76 (br. s., 1H), 4.02 (br. s., 1H), 4.18 (br. s., 1H), 4.53 (br. s., 1H), 4.74 (br. s., 1H), 5.51-5.70 (m, 1H), 6.07 (br. s., 1H), 6.63-6.86 (m, 1H), 6.91 (d, J = 7.52 Hz, 1H), 7.19 (br. s., 1H), 8.05 (br. s., 1H), 8.24 (br. s., 1H), 8.54 (br. s., 1H), 10.08-10.25 (m, 1H) | 507.3 |
| 33 | H₃C−N−CH₃ | O | (4-NH-naphthyl) | (4-amino-pyrazolopyrimidine-piperidine-acryloyl) | 1H NMR (400 MHz, DMSO-d6) Shift 1.60 (br. s., 1H), 1.96 (br. s., 1H), 2.21 (br. s., 1H), 2.96 (br. s., 3H), 3.14 (s, 3H), 3.76-3.91 (m, 1H), 3.97-4.39 (m, 2H), 4.49-4.64 (m, 1H), 4.75 (br. s., 1H), 5.50-5.80 (m, 1H), 6.10 (d, J = 16.40 Hz, 1H), 6.60-6.95 (m, 1H), 7.32 (d, J = 7.52 Hz, 1H), 7.60 (br. s., 4H), 7.93 (br. s., 3H), 8.05 (br. s., 1H), 8.26 (br. s., 1H), 8.36 (br. s., 1H), 8.47 (br. s., 1H), 10.57-10.83 (m, 1H) | 529.3 |

TABLE 5

| | | | | | | |
|---|---|---|---|---|---|---|
| 34 | H₃C−N−CH₃ | O | (4-NH-3-F-phenyl) | (4-amino-pyrazolopyrimidine-piperidine-acryloyl) | 1H NMR (400 MHz, DMSO-d6) Shift 1.57 (br. s., 1H), 1.90 (br. s., 1H), 2.15 (br. s., 1H), 2.29 (br. s., 1H), 2.89 (s, 3H), 3.03 (s, 4H), 3.81 (br. s., 1H), 4.05 (d, J = 12.98 Hz, 1H), 4.12-4.27 (m, 1H), 4.54 (d, J = 10.93 Hz, 1H), 4.70 (br. s., 1H), 5.55-5.71 (m, 1H), 6.10 (d, J = 14.35 Hz, 1H), 6.64-6.88 (m, 1H), 7.27 (t, J = 8.54 Hz, 1H), 7.62 (d, J = 8.88 Hz, 1H), 7.85 (d, J = 12.30 Hz, 1H), 8.14 (br. s., 1H), 8.25 (s, 1H), 8.40 (d, J = 16.40 Hz, 1H), 10.35-10.59 (m, 1H) | 497.3 |
| 35 | H₃C−N−CH₃ | O | (4-NH-2,3-diF-phenyl) | (4-amino-pyrazolopyrimidine-piperidine-acryloyl) | 1H NMR (400 MHz, DMSO-d6) Shift 1.58 (br. s., 1H), 1.92 (br. s., 1H), 2.17 (br. s., 1H), 2.30 (br. s., 1H), 2.50 (s, 2H), 2.91 (s, 4H), 3.05 (s, 4H), 3.71 (br. s., 1H), 4.05 (br. s., 1H), 4.22-4.64 (m, 2H), 4.71 (br. s., 1H), 5.64 (d, J = 17.77 Hz, 1H), 6.09 (d, J = 17.77 Hz, 1H), 6.64-6.91 (m, 1H), 7.14-7.21 (m, 1H), 7.40 (br. s., 1H), 8.11 (br. s., 1H), 8.25 (s, 1H), 8.41 (s, 1H), 10.33-10.67 (m, 1H) | 515.3 |
| 36 | H₃C−N−CH₃ | O | (4-NH-2-OMe-phenyl) | (4-amino-pyrazolopyrimidine-piperidine-acryloyl) | 1H NMR (400 MHz, DMSO) Shift 1.21 (br. s., 1H), 1.58 (m, 1H), 1.96 (br. s., 1H), 2.12-2.35 (m, 2H), 2.89 (s, 3H), 3.02 (s, 3H), 3.79 (br. s., 1H), 3.84-3.90 (m, 3H), 3.99 (d, J = 11.62 Hz, 1H), 4.45 (d, J = 12.30 Hz, 0.5H), 4.19 (d, J = 12.98 Hz, 0.5H), 4.76 (br. s., 1H), 5.65 (d, J = 10.25 Hz, 1H), 5.99-6.10 (m, 1H), 6.58-6.88 (m, 2H), 6.92 (d, J = 2.73 Hz, 1H), 8.01 (d, J = 8.88 Hz, 1H), 8.15 (br. s., 1H), 8.22-8.28 (m, 1H), 8.46 (br. s., 1H), 9.62 (br. s., 1H) | 509.3 |

TABLE 5-continued

| # | R1 | X | Ar | Het | 1H NMR | MS |
|---|---|---|---|---|---|---|
| 37 | H3C-N-CH3 | O | quinolin-8-ylamino (5-position) | 4-amino-pyrazolo[3,4-d]pyrimidine with acryloyl-piperidinyl | 1H NMR (400 MHz, DMSO-d6) Shift 1.66 (br. s., 1H), 1.97-2.17 (m, 1H), 2.25 (br. s., 1H), 2.28-2.38 (m, 1H), 2.94 (s, 3H), 3.12-3.22 (m, 5H), 3.76-4.17 (m, 2H), 4.20-4.51 (m, 1H), 4.80 (br. s., 1H), 5.51-5.61 (m, 1H), 6.04 (d, J = 15.03 Hz, 1H), 6.61-6.88 (m, 1H), 7.44 (d, J = 8.88 Hz, 1H), 7.72 (dd, J = 8.54, 4.44 Hz, 1H), 8.24 (s, 1H), 8.29 (s, 1H), 8.37 (d, J = 8.20 Hz, 1H), 8.50 (br. s., 1H), 8.72 (d, J = 8.88 Hz, 1H), 9.05 (d, J = 3.42 Hz, 1H), 11.34 (br. s., 1H) | 530.3 |
| 38 | H3C-N-CH3 | O | 2,5-dimethyl-4-aminophenyl | 4-amino-pyrazolo[3,4-d]pyrimidine with acryloyl-piperidinyl | 1H NMR (400 MHz, DMSO-d6) Shift 1.57 (br. s., 1H), 1.94 (br. s., 1H), 2.08 (s, 3H), 2.18 (s, 4H), 2.29 (br. s., 1H), 2.89 (s, 3H), 3.05 (s, 3H), 3.77 (br. s., 1H), 3.97-4.35 (m, 2H), 4.52 (d, J = 10.93 Hz, 1H), 4.71 (br. s., 1H), 5.52-5.70 (m, 1H), 6.00-6.12 (m, 1H), 6.60-6.88 (m, 1H), 6.96 (s, 1H), 7.30 (br. s., 1H), 8.06 (br. s., 1H), 8.24 (s, 1H), 8.52 (br. s., 1H), 9.91-10.09 (m, 1H) | 507.3 |
| 39 | H3C-N-CH3 | CH2 | 2,5-dimethyl-4-aminophenyl | 4-amino-pyrazolo[3,4-d]pyrimidine with acryloyl-piperidinyl | 1H NMR (400 MHz, DMSO-d6) Shift 1.58 (br. s., 1H), 1.96 (br. s., 1H), 2.13 (s, 3H), 2.16 (s, 2H), 2.23 (s, 1H), 2.29 (br. s., 1H), 2.83 (s, 3H), 3.02 (s, 3H), 3.61 (s, 2H), 3.77 (br. s., 1H), 3.97-4.36 (m, 2H), 4.49 (br. s., 1H), 4.77 (br. s., 1H), 5.50-5.70 (m, 1H), 5.99-6.12 (m, 1H), 6.83 (s, 1H), 6.94 (s, 1H), 7.23 (br. s., 1H), 8.10 (br. s., 1H), 8.24 (s, 1H), 8.57 (br. s., 1H), 9.83-10.02 (m, 1H) | 505.3 |
| 40 | H3C-N-CH3 | CH2 | 3-methoxy-4-aminophenyl | 4-amino-pyrazolo[3,4-d]pyrimidine with acryloyl-piperidinyl | 1H NMR (400 MHz, DMSO-d6) Shift 1.57 (br. s., 1H), 1.87 (d, J = 19.13 Hz, 1H), 2.15 (br. s., 1H), 2.29 (br. s., 1H), 2.80 (s, 3H), 2.98 (s, 3H), 3.76 (s, 3H), 3.84 (br. s., 1H), 3.99-4.30 (m, 3H), 4.51 (br. s., 1H), 4.70 (br. s., 1H), 5.56-5.71 (m, 1H), 6.10 (d, J = 13.67 Hz, 1H), 6.82 (d, J = 8.88 Hz, 1H), 7.02-7.07 (m, J = 8.20 Hz, 1H), 7.36-7.42 (m, J = 8.20 Hz, 1H), 7.47 (br. s., 1H), 8.08-8.19 (m, 2H), 8.25 (s, 1H), 8.49 (br. s., 1H), 10.06-10.30 (m, 1H) | 507.3 |
| 41 | H3C-N-CH3 | CH2 | quinolin-8-ylamino (5-position) | 4-amino-pyrazolo[3,4-d]pyrimidine with acryloyl-piperidinyl | 1H NMR (400 MHz, DMSO-d6) Shift 1.66 (br. s., 1H), 2.00-2.17 (m, 1H), 2.25 (br. s., 1H), 2.29-2.44 (m, 1H), 2.83 (s, 3H), 3.09-3.17 (m, 3H), 3.33-3.55 (m, 2H), 4.14 (s, 3H), 4.21-4.51 (m, 1H), 4.81 (br. s., 1H), 5.51-5.62 (m, 1H), 6.04 (d, J = 16.40 Hz, 1H), 6.82 (d, J = 10.93 Hz, 1H), 7.45 (d, J = 8.20 Hz, 1H), 7.66 (dd, J = 8.88, 4.10 Hz, 1H), 8.24 (s, 1H), 8.29 (s, 1H), 8.43 (d, J = 8.88 Hz, 1H), 8.54 (br. s., 1H), 8.66 (d, J = 8.20 Hz, 1H), 8.99 (d, J = 4.10 Hz, 1H), 11.46 (br. s., 1H) | 528.3 |

TABLE 6

| # | R1 | X | Ar | Het | 1H NMR | MS |
|---|---|---|---|---|---|---|
| 42 | H3C-N-CH3 | CH2 | 2-fluoro-4-aminophenyl | 4-amino-pyrazolo[3,4-d]pyrimidine with acryloyl-piperidinyl | 1H NMR (400 MHz, DMSO-d6) Shift 1.56 (br. s., 1H), 1.84 (br. s., 1H), 2.14 (br. s., 1H), 2.29 (br. s., 1H), 2.81 (s, 3H), 3.02 (s, 3H), 3.66 (s, 2H), 3.82 (br. s., 1H), 4.09 (br. s., 2H), 4.44-4.56 (m, 1H), 4.60-4.85 (m, 1H), 5.49-5.75 (m, 1H), 6.10 (d, J = 13.67 Hz, 1H), 6.60-6.95 (m, 1H), 7.22 (t, J = 8.20 Hz, 1H), 7.55 (d, J = 8.20 Hz, 1H), 7.69 (d, J = 11.62 Hz, 1H), 8.11 (s, 1H), 8.25 (s, 1H), 8.40 (br. s., 1H), 10.26-10.57 (m, 1H) | 495.3 |

TABLE 6-continued

| # | R1 | X | Ar | Het | 1H NMR | MS |
|---|----|----|----|----|--------|-----|
| 43 | H3C-N-CH3 | O | 3,5-difluoro-4-NH-phenyl | 4-amino-pyrazolopyrimidine-piperidine-acryloyl | 1H NMR (400 MHz, DMSO-d6) Shift 1.58 (br. s., 1H), 1.91 (br. s., 1H), 2.16 (br. s., 1H), 2.21-2.44 (m, 1H), 2.92 (s, 3H), 3.06 (s, 3H), 3.79 (br. s., 1H), 4.07 (d, J = 13.67 Hz, 1H), 4.24 (br. s., 1H), 4.57 (d, J = 12.98 Hz, 1H), 4.71 (br. s., 1H), 5.58-5.71 (m, 1H), 6.10 (d, J = 15.03 Hz, 1H), 6.78-6.89 (m, 1H), 7.75 (d, J = 9.57 Hz, 2H), 8.18 (br. s., 1H), 8.26 (br. s., 2H), 10.53-10.72 (m, 1H) | 515.3 |
| 44 | H3C-N-CH3 | O | 3,5-dimethyl-4-NH-phenyl | 4-amino-pyrazolopyrimidine-piperidine-acryloyl | 1H NMR (400 MHz, DMSO-d6) Shift 1.57 (br. s., 1H), 1.95 (br. s., 1H), 2.15 (s, 7H), 2.30 (br. s., 1H), 2.88 (s, 3H), 3.01 (s, 3H), 3.78 (m., 2H), 4.04 m., 2H), 4.17 (m., 2H), 4.51 (m, 1H), 4.71 (br. s., 1H), 5.66 (br. s., 1H), 6.08 (d, J = 15.72 Hz, 1H), 6.64-6.85 (m, 1H), 6.87 (s, 2H), 8.02 (br. s., 1H), 8.21 (d, J = 17.08 Hz, 2H), 8.55 (br. s., 1H), 9.94-10.15 (m, 1H) | 507.3 |
| 45 | H3C-N-CH3 | O | 3,5-dichloro-4-NH-phenyl | 4-amino-pyrazolopyrimidine-piperidine-acryloyl | 1H NMR (400 MHz, DMSO-d6) Shift 1.58 (br. s., 1H), 1.89 (d, J = 10.93 Hz, 1H), 2.16 (br. s., 1H), 2.22-2.43 (m, 1H), 2.92 (s, 3H), 3.09 (s, 3H), 3.77 (br. s., 1H), 4.08 (br. s., 1H), 4.24 (br, 1H), 4.54 (br. s., 1H), 4.70 (br. s., 1H), 5.54-5.71 (m, 1H), 6.04-6.14 (m, 1H), 6.59-6.96 (m, 1H), 8.05 (s, 2H), 8.16 (br. s., 1H), 8.26 (br. s., 2H), 10.64 (br. s., 1H) | 547.2 |
| 46 | H3C-N-CH3 | O | 3,5-dimethyl-4-NH-phenyl | 4-amino-pyrazolopyrimidine-piperidine-acryloyl | 1H NMR (400 MHz, DMSO-d6) Shift 1.57 (br. s., 1H), 1.87 (d, J = 18.45 Hz, 1H), 2.09 (s, 7H), 2.19-2.41 (m, 1H), 2.90 (s, 3H), 3.08 (s, 3H), 3.76-3.89 (m, 1H), 4.06 (d, J = 4.78 Hz, 3H), 4.17 (br. s., 1H), 4.43-4.61 (m, 1H), 4.64-4.87 (m, 1H), 5.68 (d, J = 10.25 Hz, 1H), 6.11 (d, J = 15.03 Hz, 1H), 6.63-6.95 (m, 1H), 7.52 (s, 2H), 8.12 (br. s., 1H), 8.25 (s, 1H), 8.48 (br. s., 1H), 10.04-10.27 (m, 1H) | 507.3 |
| 47 | H3C-N-CH3 | CH2 | 3-(N,N-dimethylamino)-4-NH-phenyl | 4-amino-pyrazolopyrimidine-piperidine-acryloyl | 1H NMR (400 MHz, DMSO-d6) Shift 1.56-1.81 (m, 1H), 2.08 (br. s., 1H), 2.24 (d, J = 4.78 Hz, 2H), 2.69 (s, 6H), 2.84 (s, 3H), 3.02 (s, 3H), 3.67 (s, 2H), 3.95 (br. s., 2H), 4.08 (br. s., 2H), 4.31-4.50 (m, 1H), 4.71-4.96 (m, 1H), 5.40-5.75 (m, 1H), 5.89-6.15 (m, 1H), 6.47-6.93 (m, 1H), 7.00 (d, J = 8.20 Hz, 1H), 7.17 (s, 1H), 8.12-8.24 (m, 3H), 8.30 (s, 1H), 8.52 (br. s., 1H), 10.08 (br. s., 1H) | 520.3 |
| 48 | H3C-N-CH3 | CH2 | 3-vinyl-4-NH-phenyl | 4-amino-pyrazolopyrimidine-piperidine-acryloyl | 1H NMR (400 MHz, DMSO-d6) Shift 1.58 (br. s., 1H), 1.93 (br. s., 1H), 2.17 (br. s., 1H), 2.29 (br. s., 2H), 2.50 (s, 1H), 2.82 (s, 3H), 3.02 (s, 4H), 3.70 (s, 4H), 4.07 (q, J = 5.01 Hz, 2H), 4.12-4.31 (m, 1H), 4.46-4.81 (m, 2H), 5.31 (d, J = 11.62 Hz, 1H), 5.53-5.67 (m, 1H), 5.75 (d, J = 17.08 Hz, 1H), 6.07 (br. s., 1H), 6.80 (dd, J = 17.43, 11.28 Hz, 2H), 7.16 (d, J = 6.15 Hz, 1H), 7.33 (d, J = 8.20 Hz, 1H), 7.50 (s, 1H), 8.04 | 503.3 |
| 49 | H3C-N-CH3 | CH2 | 3-ethyl-4-NH-phenyl | 4-amino-pyrazolopyrimidine-piperidine-acryloyl | 1H NMR (400 MHz, DMSO-d6) Shift 1.11 (t, J = 7.52 Hz, 3H), 1.58 (br. s., 1H), 1.94 (br. s., 1H), 2.17 (br. s., 1H), 2.29 (br. s., 1H), 2.59 (q, J = 7.52 Hz, 2H), 2.81 (s, 3H), 2.99 (s, 3H), 3.66 (s, 2H), 3.74-4.11 (m, 1H), 4.14-4.57 (m, 1H), 4.72 (br. s., 1H), 5.50-5.75 (m, 1H), 5.99-6.12 (m, 1H), 6.84 (br. s., 1H), 7.06 (d, J = 8.20 Hz, 1H), 7.13 (s, 1H), 7.35 (br. s., 1H), 7.98-8.12 (m, 1H), 8.24 (s, 1H), 8.52 (br. s., 1H), 9.86-10.07 (m, 1H) | 505.3 |

TABLE 7

| # | R1 | R2 | Ar | Het | 1H NMR | MS |
|---|---|---|---|---|---|---|
| 50 | H3C-N-CH3 | CH2 | 4-F, 3-Cl, NH-phenyl | 4-amino-pyrazolopyrimidine-piperidine-acryloyl | 1H NMR (400 MHz, DMSO-d6) Shift 1.15-1.36 (m, 1H), 1.45-1.69 (m, 1H), 1.86-2.04 (m, 1H), 2.15-2.37 (m, 2H), 2.81 (s, 3H), 3.05 (s, 3H), 3.78 (s, 2H), 3.94-4.61 (m, 3H), 4.64-4.88 (m, 1H), 5.54-5.75 (m, 1H), 5.97-6.17 (m, 1H), 6.60-6.93 (m, 1H), 7.26 (t, J = 7.93 Hz, 1H), 7.60 (d, J = 8.25 Hz, 1H), 8.07-8.46 (m, 3H), 10.24 (s, 1H) | 529.3 |
| 51 | H3C-N-CH3 | CH2 | furan-phenyl-NH | 4-amino-pyrazolopyrimidine-piperidine-acryloyl | 1H NMR (400 MHz, DMSO-d6) Shift 1.60 (br. s., 1H), 1.96 (br. s., 1H), 2.15-2.32 (m, 2H), 2.82 (s, 3H), 3.02 (s, 3H), 3.73 (s, 3H), 4.07 (br. s., 2H), 4.17 (br. s., 1H), 4.23-4.62 (m, 1H), 4.74 (br. s., 1H), 5.49-5.70 (m, 1H), 5.99-6.12 (m, 1H), 6.64 (br. s., 1H), 6.65-6.83 (m, 1H), 6.88 (d, J = 2.73 Hz, 1H), 7.22 (d, J = 8.20 Hz, 1H), 7.60 (s, 1H), 7.84 (s, 1H), 7.89 (br. s., 1H), 8.08-8.17 (m, 2H), 8.26 (s, 1H), 8.42 (br. s., 1H), 10.32 (d, J = 12.98 Hz, 1H) | 543.3 |
| 52 | H3C-N-CH3 | CH2 | furan-phenyl-NH | 4-amino-pyrazolopyrimidine-piperidine-acryloyl | 1H NMR (400 MHz, DMSO-d6) Shift 1.57 (br. s., 1H), 1.94 (d, J = 14.35 Hz, 1H), 2.08-2.28 (m, 2H), 2.82 (s, 3H), 3.02 (s, 3H), 3.71 (s, 2H), 4.05 (br. s., 1H), 4.50 (d, J = 11.62 Hz, 1H), 4.71 (br. s., 1H), 5.51-5.69 (m, 1H), 6.08 (d, J = 17.08 Hz, 1H), 6.82 (s, 2H), 7.20 (d, J = 8.20 Hz, 1H), 7.36 (s, 1H), 7.80 (br. s., 2H), 8.00 (s, 1H), 8.11 (br. s., 1H), 8.25 (s, 1H), 8.40 (br. s., 1H), 9.92 (br. s., 1H) | 543.3 |
| 53 | H3C-N-CH3 | CH2 | benzodioxole-NH | 4-amino-pyrazolopyrimidine-piperidine-acryloyl | 1H NMR (400 MHz, DMSO-d6) Shift 1.08-1.35 (m, 1H), 1.49-1.71 (m, 1H), 1.86-2.02 (m, 1H), 2.08-2.38 (m, 2H), 2.81 (s, 3H), 3.01 (s, 3H), 3.60 (s, 2H), 3.68-4.61 (m, 3H), 4.64-4.90 (m, 1H), 5.58-5.81 (m, 1H), 6.01 (s, 2H), 6.09 (s, 1H), 6.68 (d, J = 8.20 Hz, 1H), 6.71-6.89 (m, 1H), 6.97 (d, J = 7.52 Hz, 1H), 8.02-8.15 (m, 1H), 8.24 (s, 1H), 8.46 (br. s., 1H), 10.10 (br. s., 1H) | 521.3 |
| 54 | H3C-N-CH3 | CH2 | 3-Cl, NH-phenyl | 4-amino-pyrazolopyrimidine-pyrrolidine-acryloyl | 1H NMR (400 MHz, DMSO-d6) Shift 2.37-2.43 (m, 1H), 2.81 (s, 3H), 2.99 (s, 3H), 3.56-3.65 (m, 1H), 3.69 (s, 2H), 3.73-3.85 (m, 1H), 3.86-4.01 (m, 2H), 4.02-4.16 (m, 1H), 5.44-5.59 (m, 1H), 5.60-5.72 (m, 1H), 6.07-6.19 (m, 1H), 6.50-6.70 (m, 1H), 7.16-7.26 (m, 1H), 7.36-7.44 (m, 1H), 7.82-7.95 (m, 1H), 8.09-8.20 (m, 1H), 8.23-8.28 (m, 1H), 8.30-8.43 (m, 1H), 9.88-10.10 (m, 1H) | 497.3 |
| 55 | H3C-N-CH3 | CH2 | 4-Cl, 3-OCH3, NH-phenyl | 4-amino-pyrazolopyrimidine-pyrrolidine-acryloyl | 1H NMR (400 MHz, DMSO-d6) Shift 2.83 (s, 3H), 3.05 (s, 3H), 3.59-3.81 (m, 7H), 3.81-3.99 (m, 3H), 4.00-4.18 (m, 1H), 5.48-5.76 (m, 2H), 6.09-6.24 (m, 1H), 6.48-6.74 (m, 1H), 7.05-7.12 (m, 1H), 7.95-8.07 (m, 1H), 8.15-8.25 (m, 1H), 8.25-8.33 (m, 1H), 8.33-8.44 (m, 1H), 9.70-9.78 (m, 1H) | 527.3 |
| 56 | H3C-N-CH3 | CH2 | 4-F, 3-CH3, NH-phenyl | 4-amino-pyrazolopyrimidine-pyrrolidine-acryloyl | 1H NMR (400 MHz, DMSO-d6) Shift 2.09 (s, 3H), 2.41 (br. s., 1H), 2.83 (s, 3H), 3.04 (s, 3H), 3.61 (br. s., 1H), 3.69 (s, 2H), 3.74-3.87 (m, 1H), 3.91 (br. s., 1H), 3.98-4.17 (m, 2H), 5.42-5.59 (m, 1H), 5.66 (dd, J = 17.08, 10.25 Hz, 1H), 6.14 (d, J = 16.40 Hz, 1H), 6.52-6.68 (m, 1H), 7.05-7.12 (m, 1H), 7.23 (t, J = 7.86 Hz, 1H), 8.14 (br. s., 1H), 8.27 (s, 1H), 8.53 (br. s., 1H), 10.18 (d, J = 15.72 Hz, 1H) | 495.3 |

TABLE 7-continued

| # | | | | | NMR | MS |
|---|---|---|---|---|---|---|
| 57 | H3C−N−CH3 | CH2 | [aryl with F, OCH3, NH] | [pyrazolopyrimidine with NH2, acryloyl pyrrolidine] | 1H NMR (400 MHz, DMSO-d6) Shift 2.39 (br. s., 1H), 2.82 (s, 3H), 3.04 (s, 3H), 3.70 (s, 2H), 3.75-3.96 (m, 6H), 4.02-4.14 (m, 1H), 5.45-5.73 (m, 2H), 6.16 (dd, J = 17.08, 8.20 Hz, 1H), 6.53-6.71 (m, 1H), 6.97 (t, J = 8.20 Hz, 1H), 7.82 (d, J = 4.78 Hz, 1H), 8.21 (br. s., 1H), 8.29 (s, 1H), 8.42 (br. s., 1H), 9.74 (br. s., 1H) | 511.2 |
| 58 | H3C−N−CH3 | O | [naphthyl with NH] | [pyrazolopyrimidine with NH2, acryloyl pyrrolidine] | 1H NMR (400 MHz, DMSO-d6) Shift 2.50-2.67 (m, 2H), 2.96 (s, 3H), 3.14 (s, 3H), 3.63 (br. s., 1H), 3.80 (d, J = 5.47 Hz, 1H), 3.86-4.04 (m, 2H), 4.04-4.20 (m, 2H), 5.51-5.71 (m, 2H), 6.11-6.19 (m, 1H), 6.56-6.70 (m, 1H), 7.33 (d, J = 8.20 Hz, 1H), 7.57-7.66 (m, 3H), 7.91 (dd, J = 6.15, 2.73 Hz, 2H), 8.07 (br. s., 1H), 8.24-8.31 (m, 1H), 8.48 (br. s., 1H), 10.68 (d, J = 6.83 Hz, 1H) | 515.3 |

TABLE 8

| # | | | | | NMR | MS |
|---|---|---|---|---|---|---|
| 59 | H3C−N−CH3 | CH2 | [aryl with 2×CH3, NH] | [pyrazolopyrimidine with NH2, acryloyl pyrrolidine] | 1H NMR (400 MHz, DMSO-d6) Shift 2.11 (s, 3H), 2.12 (s, 3H), 2.35-2.70 (m, 2H), 2.86 (s, 3H), 3.05 (s, 3H), 3.47-4.25 (m, 4H), 3.71 (s, 2H), 5.48-5.61 (m, 1H), 5.62-5.75 (m, 1H), 6.11-6.19 (m, 1H), 6.52-6.72 (m, 1H), 6.96 (d, J = 8.2 Hz, 1H), 7.12-7.22 (m, 1H), 8.08 (br. s., 1H), 8.27 (s., 1H), 8.59 (br. s., 1H), 10.10-10.30 (m, 1H) | 491.5 |
| 60 | H3C−N−CH3 | CH2 | [aryl with vinyl, NH] | [pyrazolopyrimidine with NH2, acryloyl pyrrolidine] | 1H NMR (400 MHz, DMSO-d6) Shift 2.81 (s, 3H), 3.01 (s, 3H), 3.61 (br. s., 2H), 3.70 (s, 2H), 3.75-3.96 (m, 2H), 4.00-4.24 (m, 2H), 5.24-5.80 (m, 3H), 6.13 (d, J = 15.03 Hz, 1H), 6.50-6.67 (m, 1H), 6.78 (dd, J = 17.77, 10.93 Hz, 1H), 7.16 (d, J = 8.20 Hz, 1H), 7.37 (d, J = 8.20 Hz, 1H), 7.49 (s, 1H), 8.08 (br. s., 1H), 8.25 (s, 1H), 8.50 (br. s., 1H), 10.20 (d, J = 11.62 Hz, 1H) | 489.3 |
| 61 | H3C−N−CH3 | CH2 | [naphthyl with NH] | [pyrazolopyrimidine with NH2, acryloyl pyrrolidine] | 1H NMR (400 MHz, DMSO-d6) Shift 2.49-2.64 (m, 2H), 2.85 (s, 3H), 3.07 (s, 3H), 3.61 (br. s., 1H), 3.79 (m, 1H), 3.85-4.02 (m, 2H), 4.03-4.11 (m, 2H), 4.15 (s, 2H), 5.49-5.69 (m, 2H), 6.14 (dd, J = 16.74, 2.39 Hz, 1H), 6.55-6.69 (m, 1H), 7.35 (d, J = 7.52 Hz, 1H), 7.49-7.64 (m, 3H), 7.87-7.99 (m, 2H), 8.01-8.15 (m, 1H), 8.26 (s, 1H), 8.50 (br. s., 1H), 10.62 (d, J = 6.83 Hz, 1H) | 513.3 |
| 62 | H3C−N−CH3 | CH2 | [aryl with Br, NH] | [pyrazolopyrimidine with NH2, acryloyl pyrrolidine] | 1HNMR (400 MHz, DMSO-d6) Shift 2.81 (s, 3H), 3.00 (s, 3H), 3.61 (br. s., 1H), 3.69 (s, 2H), 3.81 (d, J = 8.88 Hz, 1H), 3.90 (br. s., 1H), 3.97 (d, J = 8.20 Hz, 1H), 4.03-4.17 (m, 2H), 5.56-5.70 (m, 2H), 6.06-6.22 (m, 1H), 6.53-6.69 (m, 1H), 7.25 (d, J = 8.20 Hz, 1H), 7.50-7.58 (m, 1H), 7.93 (dd, J = 8.20, 4.10 Hz, 1H), 8.17 (br. s., 1H), 8.27 (s, 1H), 8.34 (br. s., 1H), 9.87-10.05 (m, 1H) | 541.2 |

TABLE 8-continued

| 63 | H₃C-N-CH₃ | O | 3-methyl-4-NH-phenyl | 4-amino-pyrazolo[3,4-d]pyrimidine-pyrrolidine-acryloyl | 1H NMR (400 MHz, DMSO-d6) Shift 2.16-2.23 (m, 3H), 2.31-2.42 (m, 1H), 2.88 (s, 3H), 3.01 (s, 3H), 3.58 (br. s., 1H), 3.66-3.94 (m, 2H), 3.99-4.15 (m, 2H), 5.41-5.69 (m, 2H), 6.09-6.16 (m, 1H), 6.52-6.67 (m, 1H), 6.96 (dd, J = 8.54, 2.39 Hz, 1H), 7.03 (br. s., 1H), 7.44 (dd, J = 8.88, 5.47 Hz, 1H), 8.08 (br. s., 1H), 8.25 (s, 1H), 8.51 (br. s., 1H), 10.01 (d, J = 12.98 Hz, 1H) | 479.3 |
| 64 | H₃C-N-CH₃ | O | 2,3-dimethyl-4-NH-phenyl (CH₂) | 4-amino-pyrazolo[3,4-d]pyrimidine-pyrrolidine-acryloyl | 1H NMR (400 MHz, DMSO-d6) Shift 2.05 (s, 3H), 2.10 (s, 3H), 2.52 (dd, J = 13.67, 6.15 Hz, 1H), 2.85-2.95 (m, 3H), 3.06 (s, 3H), 3.49-3.63 (m, 1H), 3.70-3.95 (m, 2H), 3.99-4.16 (m, 2H), 5.45-5.69 (m, 2H), 6.08-6.16 (m, 1H), 6.52-6.67 (m, 1H), 6.91 (d, J = 8.88 Hz, 1H), 7.21 (dd, J = 8.54, 4.44 Hz, 1H), 8.06 (br. s., 1H), 8.24 (s, 1H), 8.53 (br. s., 1H), 10.15 (d, J = 13.67 Hz, 1H) | 493.3 |
| 65 | H₃C-N-CH₃ | CH₂ | 3-F, 2-Cl, 4-NH-phenyl | 4-amino-pyrazolo[3,4-d]pyrimidine-pyrrolidine-acryloyl | 1H NMR (400 MHz, DMSO-d6) Shift 1.10-1.29 (m, 1H), 2.82 (s, 3H), 3.02 (s, 3H), 3.73-3.88 (m, 3H), 3.88-4.24 (m, 3H), 5.43-5.76 (m, 2H), 6.14 (dd, J = 16.50, 6.35 Hz, 1H), 6.47-6.72 (m, 1H), 7.26 (t, J = 7.93 Hz, 1H), 7.70 (t, J = 9.20 Hz, 1H), 8.09-8.37 (m, 3H), 8.46 (s, 1H), 10.02-10.31 (m, 1H) | 515.3 |
| 66 | H₃C-N-CH₃ | O | naphthyl-NH | 4-amino-pyrazolo[3,4-d]pyrimidine-piperidine-dimethylaminobutenoyl | 1H NMR (400 MHz, DMSO-d6) Shift 1.56-1.72 (m, 1H), 1.94-2.09 (m, 1H), 2.26 (br. s., 1H), 2.53-2.62 (m, 8H), 2.99 (s, 3H), 3.24 (s., 3H), 3.80-3.97 (m, 1H), 3.97-4.12 (m, 1H), 4.17-4.69 (m, 1H), 4.71-4.94 (m, 1H), 6.51-6.69 (m, 1H), 6.71-6.99 (m, 1H), 7.31-7.43 (m, 1H), 7.65 (br. s., 4H), 7.92-8.01 (m, 2H), 8.04-8.17 (m, 1H), 8.25-8.38 (m, 1H), 8.44-8.58 (m, 1H), 10.65-10.79 (m, 1H) | 586.4 |
| 67 | H₃C-N-CH₃ | CH₂ | 2-Cl, 5-methyl, 4-NH-phenyl | 4-amino-pyrazolo[3,4-d]pyrimidine-pyrrolidine-acryloyl | 1H NMR (400 MHz, DMSO-d6) Shift 1.16-1.27 (m, 1H), 2.18 (s, 3H), 2.82 (s, 3H), 3.04 (s, 3H), 3.40-3.65 (m, 4H), 3.68-3.96 (m, 4H), 4.00-4.36 (m, 2H), 5.46-5.74 (m, 2H), 6.13 (dd, J = 16.40, 5.47 Hz, 1H), 6.49-6.82 (m, 1H), 7.17 (s, 1H), 7.61 (d, J = 6.15 Hz, 1H), 8.11 (br. s., 1H), 8.26 (s, 1H), 8.44 (br. s., 1H), 9.99 (d, J = 12.30 Hz, 1H) | 511.2 |

TABLE 9

| 68 | phenyl-N(CH₃)- | O | 3-methyl-4-NH-phenyl | 4-amino-pyrazolo[3,4-d]pyrimidine-piperidine-acryloyl | 1H NMR (400 MHz, DMSO-d6) Shift 1.57 (br. s., 1H), 1.93 (br. s., 1H), 2.12-2.26 (m, 4H), 2.29 (br. s., 1H), 3.77 (br. s., 1H), 3.96-4.18 (m, 1H), 4.18-4.57 (m, 1H), 4.71 (br. s., 1H), 5.52-5.70 (m, 1H), 6.01-6.12 (m, 1H), 6.62-6.88 (m, 1H), 7.00 (br. s., 1H), 7.08 (br. s., 1H), 7.25 (br. s., 1H), 7.37-7.50 (m, 5H), 8.07 (br. s., 1H), 8.24 (br. s., 1H), 8.50 (br. s., 1H), 9.97-10.14 (m, 1H) | 555.3 |

TABLE 9-continued

| # | R1 | X | Ar | Het | 1H NMR | MS |
|---|---|---|---|---|---|---|
| 69 | pyrrolidine | O | 2-methyl-4-aminophenyl-NH | 4-amino-pyrazolo[3,4-d]pyrimidine-piperidine-acryloyl | 1H NMR (400 MHz, DMSO-d6) Shift 1.58 (br. s., 1H), 1.86 (br. s., 6H), 2.12-2.26 (m, 4H), 2.30 (br. s., 1H), 3.77 (br. s., 1H), 3.97-4.17 (m, 1H), 4.20-4.57 (m, 1H), 4.71 (br. s., 1H), 5.53-5.70 (m, 1H), 6.00-6.13 (m, 1H), 6.62-6.90 (m, 1H), 6.98 (br. s., 1H), 7.05 (br. s., 1H), 7.41 (br. s., 1H), 8.06 (br. s., 1H), 8.24 (br. s., 1H), 8.52 (br. s., 1H), 9.96-10.19 (m, 1H) | 519.3 |
| 70 | piperidine | O | 2-methyl-4-aminophenyl-NH | 4-amino-pyrazolo[3,4-d]pyrimidine-piperidine-acryloyl | 1H NMR (400 MHz, DMSO-d6) Shift 1.54 (d, J = 12.30 Hz, 8H), 1.95 (br. s., 1H), 2.17 (br. s., 1H), 2.22 (br. s., 3H), 2.30 (br. s., 1H), 3.52 (br. s., 4H), 3.77 (br. s., 1H), 3.97-4.17 (m, 1H), 4.19-4.56 (m, 1H), 4.73 (br. s., 1H), 5.52-5.70 (m, 1H), 6.01-6.12 (m, 1H), 6.59-6.89 (m, 1H), 6.97 (br. s., 1H), 7.04 (br. s., 1H), 7.40 (br. s., 1H), 8.07 (br. s., 1H), 8.24 (br. s., 1H), 8.52 (br. s., 1H), 9.95-10.13 (m, 1H) | 533.3 |
| 71 | pyrrolidine | CH2 | 2-methyl-4-aminophenyl-NH | 4-amino-pyrazolo[3,4-d]pyrimidine-piperidine-acryloyl | 1H NMR (400 MHz, DMSO-d6) Shift 1.20 (br. s., 1H), 1.58 (br. s., 1H), 1.74 (d, J = 5.47 Hz, 2H), 1.80-1.90 (m, 2H), 1.95 (br. s., 1H), 2.21 (br. s., 5H), 2.30 (br. s., 1H), 3.57 (br. s., 3H), 3.79 (br. s., 1H), 3.97-4.14 (m, 2H), 4.15-4.57 (m, 1H), 4.70 (br. s., 1H), 5.51-5.70 (m, 1H), 6.00-6.12 (m, 1H), 6.60-6.92 (m, 1H), 7.07 (br. s., 1H), 7.13 (br. s., 1H), 7.36 (br. s., 1H), 8.07 (br. s., 1H), 8.24 (br. s., 1H), 8.53 (br. s., 1H), 9.89-10.06 (m, 1H) | 517.3 |
| 72 | H3CO-N(CH3)- | CH2 | 2-methyl-4-aminophenyl-NH | 4-amino-pyrazolo[3,4-d]pyrimidine-piperidine-acryloyl | 1H NMR (400 MHz, DMSO-d6) Shift 1.58 (br. s., 1H), 1.95 (br. s., 1H), 2.13-2.26 (m, 4H), 2.29 (br. s., 1H), 3.09 (s, 3H), 3.61-3.73 (m, 6H), 3.79 (br. s., 1H), 3.96-4.28 (m, 2H), 4.53 (br. s., 1H), 4.70 (br. s., 1H), 5.50-5.70 (m, 1H), 6.00-6.12 (m, 1H), 6.61-6.89 (m, 1H), 7.05-7.16 (m, 2H), 7.38 (br. s., 1H), 8.06 (br. s., 1H), 8.24 (s, 1H), 8.53 (br. s., 1H), 9.88-10.06 (m, 1H) | 507.3 |
| 73 | 3-hydroxyazetidine | CH2 | 2-methyl-4-aminophenyl-NH | 4-amino-pyrazolo[3,4-d]pyrimidine-piperidine-acryloyl | 1H NMR (400 MHz, DMSO-d6) Shift 1.53-1.68 (m, 1H), 1.82-2.02 (m, 1H), 2.22 (s, 6H), 3.52-3.60 (m, 2H), 3.66-4.27 (m, 7H), 4.34 (s, 3H), 4.65-4.82 (m, 1H), 5.68 (br. s., 2H), 5.97-6.14 (m, 1H), 6.57-6.90 (m, 1H), 6.98-7.17 (m, 2H), 7.30-7.44 (m, 1H), 8.10 (s, 1H), 8.24 (s, 1H), 8.40-8.62 (m, 1H), 9.88-10.10 (m, 1H) | 519.3 |
| 74 | N(CH3)2 | NH | 2-methyl-4-aminophenyl-NH | 4-amino-pyrazolo[3,4-d]pyrimidine-piperidine-acryloyl | 1H NMR (400 MHz, DMSO-d6) Shift 1.58 (br. s., 1H), 1.95 (br. s., 1H), 2.17 (br. s., 4H), 2.29 (br. s., 1H), 2.90 (d, J = 4.10 Hz, 6H), 3.07 (br. s., 1H), 3.78 (br. s., 1H), 3.97-4.15 (m, 1H), 4.16-4.56 (m, 1H), 4.75 (br. s., 1H), 5.50-5.73 (m, 1H), 6.01-6.12 (m, 1H), 6.84 (br. s., 1H), 7.21-7.40 (m, 3H), 8.05 (br. s., 1H), 8.21-8.30 (m, 3H), 8.57 (br. s., 1H), 9.81-9.98 (m, 1H) | 492.3 |
| 75 | pyrrolidine | NH | 2-methyl-4-aminophenyl-NH | 4-amino-pyrazolo[3,4-d]pyrimidine-piperidine-acryloyl | 1H NMR (400 MHz, DMSO) Shift 1.56 (br. s., 1H), 1.82 (br. s., 4H), 1.93 (br. s., 1H), 2.17 (br. s., 4H), 2.29 (br. s., 1H), 3.78 (br. s., 1H), 3.92-4.14 (m, 1H), 4.49 (br. s., 1H), 4.72 (br. s., 1H), 5.51-5.70 (m, 1H), 6.00-6.12 (m, 1H), 6.60-6.88 (m, 1H), 7.25 (br. s., 1H), 7.34 (br. s., 1H), 7.40 (br. s., 1H), 8.00-8.12 (m, 2H), 8.21-8.32 (m, 1H), 8.57 (br. s., 1H), 9.82-9.98 (m, 1H) | 518.3 |

TABLE 9-continued

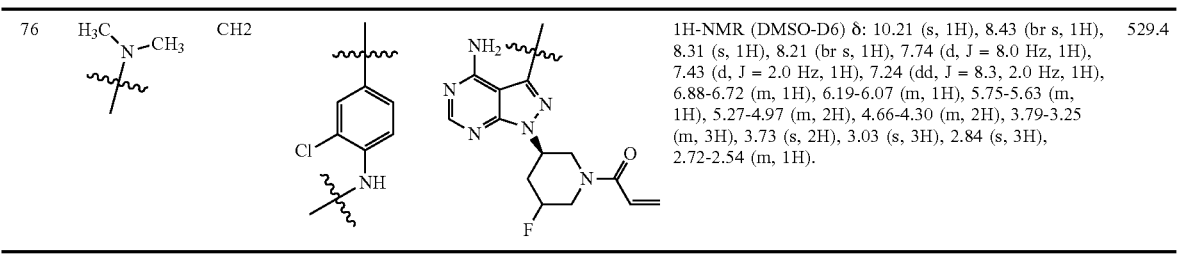

| 76 | H₃C−N−CH₃ | CH2 | (aryl with Cl, NH) | (pyrazolopyrimidine with piperidine-F, acryloyl) | 1H-NMR (DMSO-D6) δ: 10.21 (s, 1H), 8.43 (br s, 1H), 8.31 (s, 1H), 8.21 (br s, 1H), 7.74 (d, J = 8.0 Hz, 1H), 7.43 (d, J = 2.0 Hz, 1H), 7.24 (dd, J = 8.3, 2.0 Hz, 1H), 6.88-6.72 (m, 1H), 6.19-6.07 (m, 1H), 5.75-5.63 (m, 1H), 5.27-4.97 (m, 2H), 4.66-4.30 (m, 2H), 3.79-3.25 (m, 3H), 3.73 (s, 2H), 3.03 (s, 3H), 2.84 (s, 3H), 2.72-2.54 (m, 1H). | 529.4 |

TABLE 10

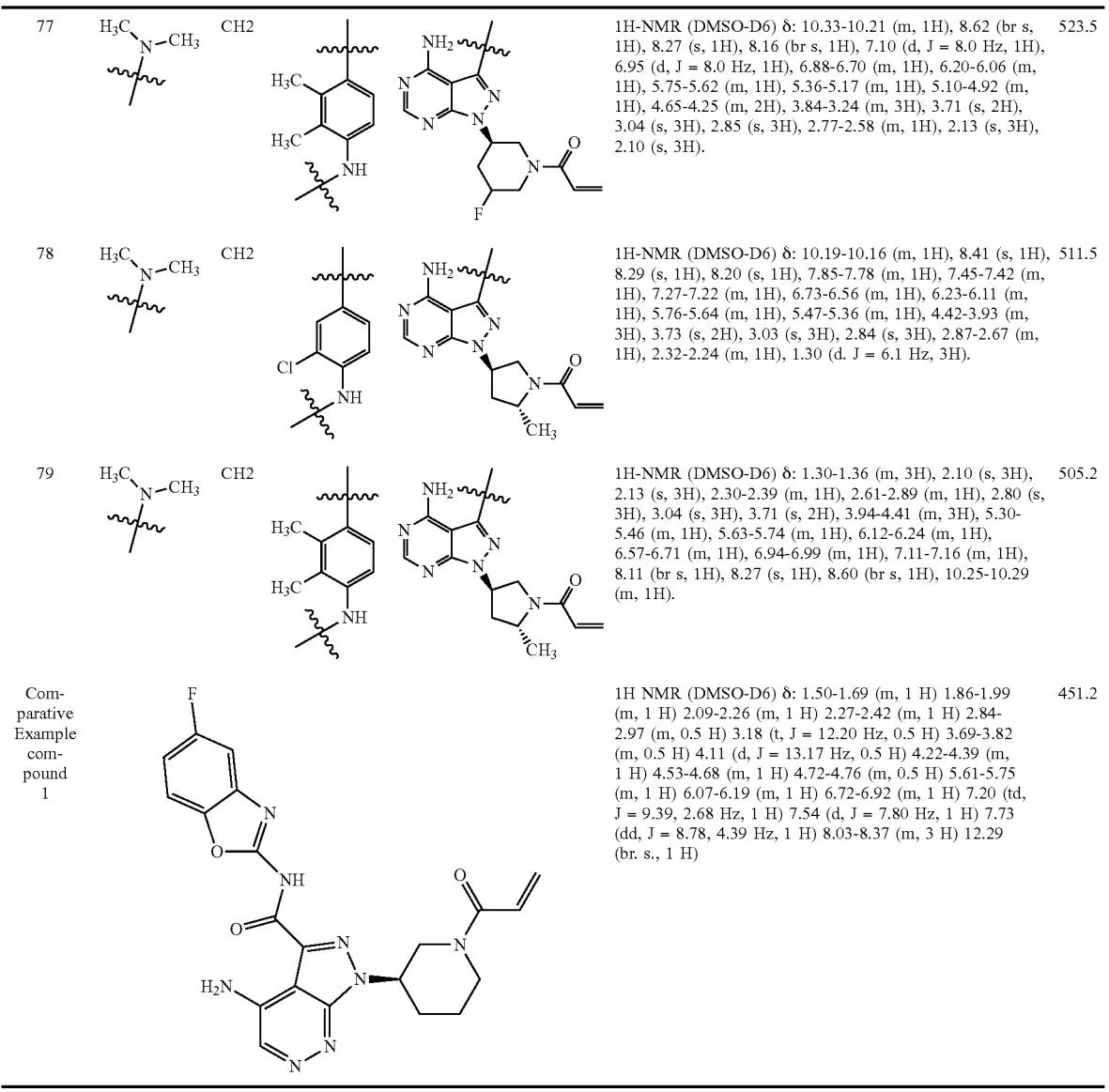

| 77 | H₃C−N−CH₃ | CH2 | (dimethyl aryl, NH) | (pyrazolopyrimidine with piperidine-F, acryloyl) | 1H-NMR (DMSO-D6) δ: 10.33-10.21 (m, 1H), 8.62 (br s, 1H), 8.27 (s, 1H), 8.16 (br s, 1H), 7.10 (d, J = 8.0 Hz, 1H), 6.95 (d, J = 8.0 Hz, 1H), 6.88-6.70 (m, 1H), 6.20-6.06 (m, 1H), 5.75-5.62 (m, 1H), 5.36-5.17 (m, 1H), 5.10-4.92 (m, 1H), 4.65-4.25 (m, 2H), 3.84-3.24 (m, 3H), 3.71 (s, 2H), 3.04 (s, 3H), 2.85 (s, 3H), 2.77-2.58 (m, 1H), 2.13 (s, 3H), 2.10 (s, 3H). | 523.5 |
| 78 | H₃C−N−CH₃ | CH2 | (aryl with Cl, NH) | (pyrazolopyrimidine with pyrrolidine-CH₃, acryloyl) | 1H-NMR (DMSO-D6) δ: 10.19-10.16 (m, 1H), 8.41 (s, 1H), 8.29 (s, 1H), 8.20 (s, 1H), 7.85-7.78 (m, 1H), 7.45-7.42 (m, 1H), 7.27-7.22 (m, 1H), 6.73-6.56 (m, 1H), 6.23-6.11 (m, 1H), 5.76-5.64 (m, 1H), 5.47-5.36 (m, 1H), 4.42-3.93 (m, 3H), 3.73 (s, 2H), 3.03 (s, 3H), 2.84 (s, 3H), 2.87-2.67 (m, 1H), 2.32-2.24 (m, 1H), 1.30 (d. J = 6.1 Hz, 3H). | 511.5 |
| 79 | H₃C−N−CH₃ | CH2 | (dimethyl aryl, NH) | (pyrazolopyrimidine with pyrrolidine-CH₃, acryloyl) | 1H-NMR (DMSO-D6) δ: 1.30-1.36 (m, 3H), 2.10 (s, 3H), 2.13 (s, 3H), 2.30-2.39 (m, 1H), 2.61-2.89 (m, 1H), 2.80 (s, 3H), 3.04 (s, 3H), 3.71 (s, 2H), 3.94-4.41 (m, 3H), 5.30-5.46 (m, 1H), 5.63-5.74 (m, 1H), 6.12-6.24 (m, 1H), 6.57-6.71 (m, 1H), 6.94-6.99 (m, 1H), 7.11-7.16 (m, 1H), 8.11 (br s, 1H), 8.27 (s, 1H), 8.60 (br s, 1H), 10.25-10.29 (m, 1H). | 505.2 |
| Comparative Example compound 1 | (fluorobenzoxazole-NH-C(O)-pyrazolopyridazine-NH₂ with piperidine-acryloyl) | | | | 1H NMR (DMSO-D6) δ: 1.50-1.69 (m, 1 H) 1.86-1.99 (m, 1 H) 2.09-2.26 (m, 1 H) 2.27-2.42 (m, 1 H) 2.84-2.97 (m, 0.5 H) 3.18 (t, J = 12.20 Hz, 0.5 H) 3.69-3.82 (m, 0.5 H) 4.11 (d, J = 13.17 Hz, 0.5 H) 4.22-4.39 (m, 1 H) 4.53-4.68 (m, 1 H) 4.72-4.76 (m, 0.5 H) 5.61-5.75 (m, 1 H) 6.07-6.19 (m, 1 H) 6.72-6.92 (m, 1 H) 7.20 (td, J = 9.39, 2.68 Hz, 1 H) 7.54 (d, J = 7.80 Hz, 1 H) 7.73 (dd, J = 8.78, 4.39 Hz, 1 H) 8.03-8.37 (m, 3 H) 12.29 (br. s., 1 H) | 451.2 |

Test Example 1 Measurement of Inhibitory Effect on HER2-Phosphorylating Activity (In Vitro)

For setting the conditions for the method for measuring the in vitro inhibitory activity of a compound against HER2-phosphorylating activity, ProfilerPro Peptide 22 from PerkinElmer Inc. was used as a substrate on the basis of the report (PLoS One, 6 (7), e21487, 2011) on HER2 kinase reaction using, as a substrate, a peptide having the same sequence (5-FAM-EEPLYWSFPAKKK-CONH2) as that of ProfilerPro Peptide 22. The purified recombinant human HER2 protein used in the test was purchased from Carna Biosciences, Inc. Also, staurosporine (Eur. J. Biochem., 234, p. 317-322, 1995; and Nat. Biotechnol., 26 (1), p. 127-132, 2008), which is a multikinase inhibitor having Her2 inhibitory activity, was purchased from Enzo Life Sciences, Inc. (item No.: ALX-380-014) and used as a positive control in this test.

For the inhibitory activity measurement of each compound, the compound of the present invention or staurosporine was first serially diluted with dimethyl sulfoxide (DMSO). Next, the HER2 protein, the substrate peptide (final concentration: 0.5 uM), manganese chloride (final concentration: 10 mM), ATP (final concentration: 6 uM), and the solution of the compound of the present invention in DMSO (final concentration of DMSO: 5%) were added into a buffer solution for kinase reaction (15 mM Tris (pH 7.5), 2 mM dithiothreitol, and 0.01% Tween 20), and the mixture was incubated at 25° C. for 40 minutes for kinase reaction. The reaction was terminated by adding EDTA (final concentration: 30 mM) thereto. Finally, the unphosphorylated substrate peptide (S) and the phosphorylated peptide (P) were separated and detected by microcapillary electrophoresis using LabChip® EZ Reader II (PerkinElmer Inc.). The amount of phosphorylation reaction was determined from the respective peak heights of S and P. The compound concentration which can suppress the phosphorylation reaction by 50% was defined as an IC50 value (nM).

The results are shown in the table below.

TABLE 11

| Example No. | HER2 inhibitory activity IC50 value (nM) |
| --- | --- |
| 1 | 10 |
| 2 | 8.3 |
| 3 | 7.1 |
| 4 | 12 |
| 5 | 11 |
| 6 | 4.0 |
| 7 | 7.1 |
| 8 | 9.2 |
| 9 | 10 |
| 10 | 13 |
| 11 | 7.5 |
| 12 | 7.5 |
| 13 | 13 |
| 14 | 4.6 |
| 15 | 8.6 |
| 16 | 10 |
| 17 | 5.9 |
| 18 | 4.4 |
| 19 | 10 |
| 20 | 13 |
| 21 | 26 |
| 22 | 48 |
| 23 | 20 |
| 24 | 38 |
| 25 | 21 |
| 26 | 7.0 |
| 27 | 3.9 |
| 28 | 46 |
| 29 | 6.5 |
| 30 | 8.7 |
| 31 | 13 |
| 32 | 9.3 |
| 33 | 6.0 |
| 34 | 11 |
| 35 | 16 |
| 36 | 5.4 |
| 37 | 11 |
| 38 | 10 |
| 39 | 22 |
| 40 | 23 |
| 41 | 18 |
| 42 | 18 |
| 43 | 14 |
| 44 | 46 |
| 45 | 28 |
| 46 | 44 |
| 47 | 52 |
| 48 | 8.5 |
| 49 | 20 |
| 50 | 2.9 |
| 51 | 17 |
| 52 | 13 |
| 53 | 14 |
| 54 | 31 |
| 55 | 49 |
| 56 | 22 |
| 57 | 31 |
| 58 | 11 |
| 59 | 45 |
| 60 | 20 |
| 61 | 13 |
| 62 | 59 |
| 63 | 38 |
| 64 | 49 |
| 65 | 20 |
| 66 | 19 |
| 67 | 72 |
| 68 | 7.7 |
| 69 | 9.2 |
| 70 | 10 |
| 71 | 11 |
| 72 | 11 |
| 73 | 74 |
| 74 | 17 |
| 75 | 16 |
| 76 | 5.0 |
| 77 | 13 |
| 78 | 14 |
| 79 | 17 |
| Staurosporine | 63 |

The results of this test demonstrated that the compound of the present invention has HER2 inhibitory activity in vitro.

Test Example 2 Measurement Test (In Vitro) of Cytostatic Activity Against HER2-Expressing Cell Line (NCI-N87) and EGFR-Expressing Cell Line (A431) and Comparison of Selectivity Thereof HER2-overexpressing human stomach cancer cell line NCI-N87 cells were suspended in RPMI1640 medium (manufactured by Life Technologies Corp.) containing 10% fetal bovine serum. Meanwhile, EGFR-overexpressing highly activated human epithelioid cancer cell line A431 cells were suspended in DMEM, high glucose medium (manufactured by Life Technologies Corp.) containing 10% fetal bovine serum. Subsequently, each cell suspension was inoculated to each well of a 384-well flat-bottom microplate and cultured at 37° C. for 1 day in an incubator containing 5% carbon dioxide. The compound of the present invention or Comparative Example compound 1 was dissolved in DMSO, and the test compound was diluted into a concentration of 500 times the final concentration using DMSO. The solution of the test compound in DMSO was diluted with the medium used in the suspension of each cell line, and this solution was added at a final concentration of DMSO of 0.2% to each well of the cell culture plate, followed by further culture at 37° C. for 3 days in an incubator containing 5% carbon dioxide. The number of cells after the 3-day culture in the presence of the compound was counted using CellTiter-Glo (manufactured by Promega Corp.) on the basis of the protocol recommended by Promega Corp. The rate of inhibition of growth was calculated according to the expression given below to determine the concentration at which the test compound inhibited the cell growth by 50% (IC50 (nM)).

The results are shown in the table below.

Rate of growth inhibition (%)=(C−T)/(C)×100

T: Luminescence intensity of a well supplemented with the test compound
C: Luminescence intensity of a well not supplemented with the test compound

TABLE 12

| Example No. | NCI-N87 cell growth inhibitory activity IC50 value (nM) | A431 cell growth inhibitory activity IC50 value (nM) |
|---|---|---|
| 1 | 19 | 2319 |
| 2 | 45 | 2666 |
| 3 | 27 | 3373 |
| 4 | 12 | 2607 |
| 5 | 6 | 1233 |
| 6 | 7 | 1289 |
| 7 | 12 | 2805 |
| 8 | 8 | 956 |
| 9 | 13 | 2446 |
| 10 | 6 | 1414 |
| 11 | 4 | 961 |
| 12 | 3 | 340 |
| 13 | 5 | 1211 |
| 14 | 4 | 486 |
| 15 | 20 | 2270 |
| 16 | 27 | 3456 |
| 17 | 5 | 910 |
| 18 | 12 | 1058 |
| 19 | 12 | 1261 |
| 26 | 5 | 984 |
| 27 | 5 | 1508 |
| 29 | 46 | 2223 |
| 30 | 23 | 2349 |
| 32 | 7 | 1921 |
| 33 | 3 | 263 |
| 34 | 32 | 2206 |
| 36 | 8 | 2607 |
| 38 | 8 | 1040 |
| 39 | 12 | 1799 |
| 48 | 4 | 314 |
| 50 | 4 | 277 |
| 53 | 11 | 1669 |
| 56 | 31 | 2513 |
| 57 | 44 | 3389 |
| 58 | 8 | 681 |
| 60 | 50 | 5255 |
| 61 | 10 | 1099 |
| 66 | 50 | 6040 |
| 71 | 26 | 2115 |
| 72 | 5 | 1172 |
| 74 | 18 | 8075 |
| 76 | 8 | 2074 |
| 77 | 19 | 2455 |
| 78 | 41 | 5450 |
| 79 | 21 | 6942 |
| Comparative Example compound 1 | 2380 | |

The test results demonstrated that as for the rate of in vitro inhibition of cell growth, the cytostatic activity of the compound of the present invention against the HER2-overexpressing cell line NCI-N87 was 47 or more times that of Comparative Example compound 1; thus the compound of the present invention not only inhibits HER2 kinase but has excellent cytostatic activity against the cells.

In addition, the results also demonstrated that the compound of the present invention also has excellent HER2 kinase inhibition selectivity over EGFR kinase.

Test Example 3 Measurement Test (In Vitro) of Cytostatic Activity Against HER2-Expressing Cell Line (SK-BR-3)

HER2-overexpressing human breast cancer cell line SK-BR-3 cells were suspended in McCoy's 5a medium (manufactured by Life Technologies Corp.) containing 10l fetal bovine serum. The cell suspension was inoculated to each well of a 384-well flat-bottom microplate and cultured at 37° C. for 1 day in an incubator containing 5% carbon dioxide. The compound of the present invention was dissolved in DMSO, and the test compound was diluted into 500 times as high concentration as the final concentration using DMSO. The solution of the test compound in DMSO was diluted with the medium used in the suspension of each cell line, and this solution was added at a final concentration of DMSO of 0.2% to each well of the cell culture plate, followed by further culture at 37° C. for 3 days in an incubator containing 5% carbon dioxide. The number of cells after the 3-day culture in the presence of the compound was counted using CellTiter-Glo (manufactured by Promega Corp.) on the basis of the protocol recommended by Promega Corp. The rate of inhibition of growth was calculated according to the expression given below to determine the concentration at which the test compound inhibited the cell growth by 50% (IC50 (nM)).

TABLE 13

| Example No. | SK-BR-3 cell growth inhibitory activity IC50 value (nM) |
|---|---|
| 1 | 20 |
| 2 | 30 |
| 3 | 9 |
| 4 | 16 |
| 5 | 11 |
| 6 | 14 |
| 7 | 31 |
| 10 | 21 |
| 11 | 12 |
| 13 | 9 |
| 14 | 10 |
| 15 | 30 |
| 16 | 40 |
| 17 | 13 |
| 19 | 24 |
| 26 | 8 |
| 27 | 9 |
| 29 | 44 |
| 30 | 39 |
| 32 | 14 |
| 33 | 9 |
| 36 | 12 |
| 38 | 12 |
| 39 | 24 |
| 53 | 18 |
| 58 | 11 |
| 60 | 39 |
| 61 | 15 |
| 66 | 29 |
| 71 | 19 |
| 72 | 16 |
| 76 | 8 |
| 77 | 12 |
| 78 | 38 |
| 79 | 13 |
| Comparative Example compound 1 | 1133 |

The results of this test demonstrated that the compound of the present invention also has excellent cytostatic activity against the HER2-overexpressing human breast cancer cell line.

The invention claimed is:
1. A compound of the following formula (I) or a salt thereof:

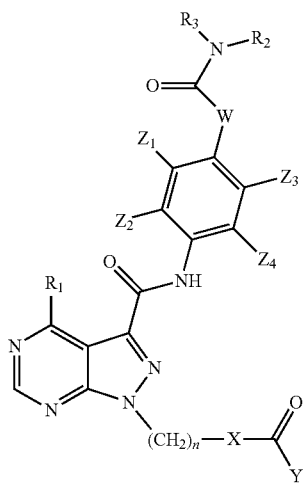

wherein X represents an optionally substituted 4- to 10-membered nitrogen-containing saturated heterocyclic group;
Y represents —C($R_4$)=C($R_5$)($R_6$);
$Z_1$, $Z_2$, $Z_3$, and $Z_4$ are the same as or different from each other and each represent a hydrogen atom, a halogen atom, a cyano group, a C2-C6 alkenyl group, an optionally substituted C1-C6 alkoxy group, an optionally substituted C1-C6 alkyl group, an optionally substituted amino group, an optionally substituted C3-C7 cycloalkyl group, a C6-C14 aromatic hydrocarbon group, or a 4- to 14-membered unsaturated heterocyclic group, or $Z_1$ and $Z_2$, or $Z_3$ and $Z_4$ optionally form, together with the respective carbon atoms bonded thereto, a benzene ring or a 5- to 7-membered saturated or unsaturated heterocyclic ring;
W represents —CH$_2$—, an oxygen atom, or —NH—;
n represents an integer of from 0 to 2;
$R_1$ represents an optionally substituted amino group;
$R_2$ and $R_3$ are the same as or different from each other and each represent a hydrogen atom, an optionally substituted C1-C6 alkoxy group, an optionally substituted C1-C6 alkyl group, or an optionally substituted C6-C14 aromatic hydrocarbon group, or $R_2$ and $R_3$ optionally form, together with the nitrogen atom bonded thereto, an optionally substituted 4- to 8-membered nitrogen-containing saturated heterocyclic group; and
$R_4$, $R_5$, and $R_6$ are the same as or different from each other and each represent a hydrogen atom or an optionally substituted C1-C6 alkyl group.

2. The compound according to claim 1 or a salt thereof, wherein
in the formula (I),
X is a 4- to 10-membered nitrogen-containing saturated heterocyclic group optionally having a halogen atom, a hydroxyl group, a cyano group, a C1-C6 alkyl group, or an amino group as a substituent;
$Z_1$, $Z_2$, $Z_3$, and $Z_4$ are the same as or different from each other and each are a hydrogen atom, a halogen atom, a cyano group, a C2-C6 alkenyl group, an optionally substituted C1-C6 alkoxy group, an optionally substituted C1-C6 alkyl group, an optionally substituted amino group, an optionally substituted C3-C7 cycloalkyl group, or a 4- to 14-membered unsaturated heterocyclic group, or $Z_1$ and $Z_2$, or $Z_3$ and $Z_4$ optionally form, together with the respective carbon atoms bonded thereto, a benzene ring or a 5- to 7-membered saturated or unsaturated heterocyclic ring;
n is 0; and
$R_1$ is an amino group.

3. The compound according to claim 1 or a salt thereof, wherein
in the formula (I),
X is a 4- to 8-membered nitrogen-containing saturated heterocyclic group optionally having a halogen atom or a C1-C6 alkyl group as a substituent;
Y is —C($R_4$)=C($R_5$)($R_6$);
$Z_1$, $Z_2$, $Z_3$, and $Z_4$ are the same as or different from each other and each are a hydrogen atom, a halogen atom, a cyano group, a C2-C6 alkenyl group, an optionally halogen atom-substituted C1-C6 alkoxy group, a C1-C6 alkyl group, an optionally C1-C6 alkyl group-substituted amino group, a C3-C7 cycloalkyl group, or a monocyclic 4- to 6-membered unsaturated heterocyclic group having one oxygen atom, or $Z_1$ and $Z_2$, or $Z_3$ and $Z_4$ optionally form, together with the respective carbon atoms bonded thereto, a benzene ring or a 5- to 7-membered saturated or unsaturated heterocyclic ring;
W is —CH$_2$—, an oxygen atom, or —NH—;
n is 0;
$R_1$ is an amino group;
$R_2$ and $R_3$ are the same as or different from each other and each are a hydrogen atom, a C1-C6 alkoxy group, a C1-C6 alkyl group, or a C6-C14 aromatic hydrocarbon group, or $R_2$ and $R_3$ optionally form, together with the nitrogen atom bonded thereto, an optionally hydroxyl group-substituted 4- to 8-membered nitrogen-containing saturated heterocyclic group; and
$R_4$, $R_5$, and $R_6$ are the same as or different from each other and each are a hydrogen atom or an optionally di(C1-C6 alkyl)amino group-substituted C1-C6 alkyl group.

4. The compound according to claim 1 or a salt thereof, wherein
in the formula (I),
X is a pyrrolidinyl group optionally having a C1-C6 alkyl group as a substituent, or a piperidinyl group optionally having a halogen atom as a substituent;
Y is —C($R_4$)=C($R_5$)($R_6$); and
$R_4$, $R_5$, and $R_6$ are the same as or different from each other and each are a hydrogen atom or a dimethylaminomethyl group.

5. The compound according to claim 1 or a salt thereof, wherein
in the formula (I),
X is a pyrrolidinyl group, a methylpyrrolidinyl group, a piperidinyl group, or a fluoropiperidinyl group;
Y is

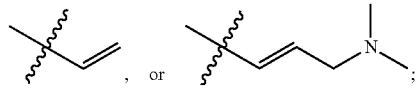

and
$R_2$ and $R_3$ are the same as or different from each other and each are a hydrogen atom, a methoxy group, a methyl group, or a phenyl group, or $R_2$ and $R_3$ optionally form, together with the nitrogen atom bonded thereto, an azetidinyl group optionally having a hydroxyl group as a substituent, a pyrrolidinyl group, or a piperidinyl group.

6. The compound according to claim 1 or a salt thereof, wherein
in the formula (I),
X is a pyrrolidinyl group, a methylpyrrolidinyl group, a piperidinyl group, or a fluoropiperidinyl group;
Y is

$Z_1$, $Z_2$, $Z_3$, and $Z_4$ are the same as or different from each other and each are a hydrogen atom, a fluorine atom, a chlorine atom, a bromine atom, a cyano group, a vinyl group, a methoxy group, a fluoromethoxy group, a difluoromethoxy group, a methyl group, an ethyl group, a dimethylamino group, a cyclopropyl group, or a furyl group, or $Z_1$ and $Z_2$ or $Z_3$ and $Z_4$ optionally form, together with the respective carbon atoms bonded thereto, a benzene ring, a pyridine ring, or a dioxolane ring;
W is —CH$_2$—, an oxygen atom, or —NH—;
n is 0;
$R_1$ is an amino group; and
$R_2$ and $R_3$ are the same as or different from each other and each are a methoxy group, a methyl group, or a phenyl group, or $R_2$ and $R_3$ optionally form, together with the nitrogen atom bonded thereto, a hydroxyazetidinyl group, a pyrrolidinyl group, or a piperidinyl group.

7. The compound according to claim 1 or a salt thereof, wherein the compound is selected from the group consisting of the following (1) to (20):
(1) (R)-1-(1-acryloylpiperidin-3-yl)-4-amino-N-(5-bromo-4-(2-(dimethylamino)-2-oxoethyl)-2-methylphenyl)-1H-pyrazolo[3,4-d]pyrimidine-3-carboxamide,
(2) (R)-1-(1-acryloylpiperidin-3-yl)-4-amino-N-(2-chloro-4-(2-(dimethylamino)-2-oxoethyl)-5-methylphenyl)-1H-pyrazolo[3,4-d]pyrimidine-3-carboxamide,
(3) (R)-1-(1-acryloylpiperidin-3-yl)-4-amino-N-(2-chloro-4-(2-(dimethylamino)-2-oxoethyl)-3-methylphenyl)-1H-pyrazolo[3,4-d]pyrimidine-3-carboxamide,
(4) (R)-1-(1-acryloylpiperidin-3-yl)-4-amino-N-(4-(2-(dimethylamino)-2-oxoethyl)-2-methylphenyl)-1H-pyrazolo[3,4-d]pyrimidine-3-carboxamide,
(5) (R)-1-(1-acryloylpiperidin-3-yl)-4-amino-N-(4-(2-(dimethylamino)-2-oxoethyl)naphthalen-1-yl)-1H-pyrazolo[3,4-d]pyrimidine-3-carboxamide,
(6) (R)-1-(1-acryloylpiperidin-3-yl)-4-amino-N-(2-chloro-4-(2-(dimethylamino)-2-oxoethyl)phenyl)-1H-pyrazolo[3,4-d]pyrimidine-3-carboxamide,
(7) (R)-1-(1-acryloylpiperidin-3-yl)-4-amino-N-(4-(2-(dimethylamino)-2-oxoethyl)-2-methoxyphenyl)-1H-pyrazolo[3,4-d]pyrimidine-3-carboxamide,
(8) (R)-1-(1-acryloylpiperidin-3-yl)-4-amino-N-(3-chloro-4-(2-(dimethylamino)-2-oxoethyl)phenyl)-1H-pyrazolo[3,4-d]pyrimidine-3-carboxamide,
(9) (R)-1-(1-acryloylpiperidin-3-yl)-4-amino-N-(5-chloro-4-(2-(dimethylamino)-2-oxoethyl)-2-methoxyphenyl)-1H-pyrazolo[3,4-d]pyrimidine-3-carboxamide,
(10) (R)-1-(1-acryloylpiperidin-3-yl)-4-amino-N-(4-(2-(dimethylamino)-2-oxoethyl)-5-fluoro-2-methylphenyl)-1H-pyrazolo[3,4-d]pyrimidine-3-carboxamide,
(11) (R)-1-(1-acryloylpiperidin-3-yl)-4-amino-N-(3-chloro-4-(2-(dimethylamino)-2-oxoethyl)-2-methoxyphenyl)-1H-pyrazolo[3,4-d]pyrimidine-3-carboxamide,
(12) (R)-1-(1-acryloylpiperidin-3-yl)-4-amino-N-(4-(2-(dimethylamino)-2-oxoethyl)-3-fluoro-2-methylphenyl)-1H-pyrazolo[3,4-d]pyrimidine-3-carboxamide,
(13) (R)-1-(1-acryloylpiperidin-3-yl)-4-amino-N-(4-(2-(dimethylamino)-2-oxoethyl)-2,3-dimethylphenyl)-1H-pyrazolo[3,4-d]pyrimidine-3-carboxamide,
(14) (R)-1-(1-acryloylpiperidin-3-yl)-4-amino-N-(4-(2-(dimethylamino)-2-oxoethyl)-3-fluoro-2-methoxyphenyl)-1H-pyrazolo[3,4-d]pyrimidine-3-carboxamide,
(15) (R)-1-(1-acryloylpiperidin-3-yl)-4-amino-N-(2-(difluoromethoxy)-4-(2-(dimethylamino)-2-oxoethyl)phenyl)-1H-pyrazolo[3,4-d]pyrimidine-3-carboxamide,
(16) (R)-1-(1-acryloylpiperidin-3-yl)-4-amino-N-(4-(2-(dim ethyl amino)-2-oxoethyl)-2-(fluoromethoxy)phenyl)-1H-pyrazolo[3,4-d]pyrimidine-3-carboxamide,
(17) (R)-1-(1-acryloylpiperidin-3-yl)-4-amino-N-(2-bromo-4-(2-(dimethylamino)-2-oxoethyl)phenyl)-1H-pyrazolo[3,4-d]pyrimidine-3-carboxamide,
(18) (R)-1-(1-acryloylpiperidin-3-yl)-4-amino-N-(2-chloro-4-(2-(dimethylamino)-2-oxoethyl)-5-fluorophenyl)-1H-pyrazolo[3,4-d]pyrimidine-3-carboxamide,
(19) (R)-1-(1-acryloylpiperidin-3-yl)-4-amino-N-(5-chloro-4-(2-(dimethylamino)-2-oxoethyl)-2-methylphenyl)-1H-pyrazolo[3,4-d]pyrimidine-3-carboxamide, and
(20) (R)-1-(1-acryloylpiperidin-3-yl)-4-amino-N-(2,5-dichloro-4-(2-(dimethylamino)-2-oxoethyl)phenyl)-1H-pyrazol o[3,4-d]pyrimidine-3-carboxamide.

8. A pharmaceutical composition comprising the compound according to claim 1 or a salt thereof, and a pharmaceutically acceptable carrier.

* * * * *